United States Patent
Zangi et al.

(10) Patent No.: US 11,299,749 B2
(45) Date of Patent: Apr. 12, 2022

(54) CELL-SPECIFIC EXPRESSION OF MODRNA

(71) Applicant: ICAHN SCHOOL OF MEDICINE AT MOUNT SINAI, New York, NY (US)

(72) Inventors: Lior Zangi, New York, NY (US); Ajit Magadum, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 405 days.

(21) Appl. No.: 16/354,814

(22) Filed: Mar. 15, 2019

(65) Prior Publication Data

US 2019/0203226 A1 Jul. 4, 2019

Related U.S. Application Data

(63) Continuation of application No. PCT/US2017/052035, filed on Sep. 18, 2017.

(60) Provisional application No. 62/395,701, filed on Sep. 16, 2016.

(51) Int. Cl.

| C12N 15/85 | (2006.01) |
| C12N 15/113 | (2010.01) |
| C12N 15/67 | (2006.01) |
| A61P 9/10 | (2006.01) |
| A61K 31/7084 | (2006.01) |
| C12N 5/077 | (2010.01) |
| C12N 5/071 | (2010.01) |

(52) U.S. Cl.
CPC .......... *C12N 15/85* (2013.01); *A61K 31/7084* (2013.01); *A61P 9/10* (2018.01); *C12N 5/0657* (2013.01); *C12N 5/0676* (2013.01); *C12N 15/113* (2013.01); *C12N 15/67* (2013.01)

(58) Field of Classification Search
None
See application file for complete search history.

(56) References Cited

U.S. PATENT DOCUMENTS

| 2009/0005336 A1 | 1/2009 | Wang |
| 2015/0133521 A1 | 5/2015 | Bloch et al. |
| 2015/0315541 A1* | 11/2015 | Bancel ................. C12N 9/0069 435/366 |

FOREIGN PATENT DOCUMENTS

| WO | 2012012739 A3 | 1/2012 |
| WO | 2015141827 A1 | 9/2015 |
| WO | 2016040395 | 3/2016 |

OTHER PUBLICATIONS

Wroblewska et al. Nature Biotechnology 33, pp. 839-843 (Year: 2015).*
Wroblewska et al. Nature Biotechnology 33, supplementary text and Figures 1-28 and Table 1-6 and notes 1-3 pp. 1-53 (Year: 2015).*
Extended European Search Report for European Patent Application No. 17851710.8 dated Feb. 14, 2020.
Xie, Z., et al., "Multi-Input RNAi-Based Logic Circuit for Identification of Specific Cancer Cells", Science, vol. 333, pp. 1307-1311 (2011).
Saito, H., et al., "Synthetic translational regulation by an L7Ae-kink-turn RNP switch", Nature Chemical Biology, vol. 6, pp. 71-78 (2010).
Kamrud et al. "Analysis of Venezuelan Equine Encephalitis Replicon Particles Packaged in Different Coats," PLoS ONE, vol. 3(7), pp. 1-8, 2008.
Montgomery et al. "Therapeutic Inhibition of miR-208a Improves Cardiac Function and Survival During Heart Failure," Circulation, vol. 124(14), pp. 1537-1547, 2011.
Stapleton et al. "Feedback Control of Protein Expression in Mammalian Cells by Tunable Synthetic Translational Inhibition," ACS Publications, vol. 1(3), pp. 83-88, 2012.
Lennox et al. "Improved Performance of Anti-miRNA Oligonucleotides Using a Novel Non-Nucleotide Modifier," Molecular Therapy—Nucleic Acids, vol. 2:e117, pp. 1-19, 2013.
Eding et al. "The Efficacy of Cardiac Anti-miR-208a Therapy Is Stress Dependent," Molecular Therapy, vol. 25(3), pp. 694-704, 2017.
International Search Report and Written Opinion of the International Searching Authority for PCT/US2017/052035, dated Jan. 18, 2018, 16 pages.

* cited by examiner

*Primary Examiner* — Brian Whiteman
(74) *Attorney, Agent, or Firm* — Heslin Rothenberg Farley & Mesiti P.C.

(57) ABSTRACT

Disclosed is an expression regulatory system for cell-specific transcription (expression) of a protein of interest, for example a cell cycle inducer that reactivates proliferation in adult or neonatal cardiomyocytes or insulin-producing beta cells. The expression regulatory system comprises a first nucleic acid that encodes a microRNA recognition element that specifically binds a target cell miR, and a translation suppressor protein; and a second nucleic acid that comprises a suppressor protein interaction motif that binds the translation suppressor protein, and a gene that encodes a protein of interest. When a cell of interest is co-transfected with the first and second nucleic acids of the system, the protein of interest expressed in a cell-specific fashion.

18 Claims, 59 Drawing Sheets

Specification includes a Sequence Listing.

| Step | Temp | Time | # of cycles |
|---|---|---|---|
| Initial denature | 95°C | 5 min | 1 |
| Denaturation | 98°C | 20 sec | 25 |
| Primer anneal | 65°C | 15 sec | |
| Extension | 72°C | 30 sec/kb ORF insert | |
| Final extension | 72°C | 5 min | 1 |

FIGURE 2 cont.

SEQUENCE LISTING

<160> NUMBER OF SEQ ID NOS: 55

<210> SEQ ID NO 1
<211> LENGTH: 536
<212> TYPE: DNA
<213> ORGANISM: Artificial Sequence
<220> FEATURE:
<223> OTHER INFORMATION: synthetic oligonucleotide

<400> SEQUENCE: 1

| | | | | | |
|---|---|---|---|---|---|
| ttggaccctc | gtacagaagc | taatacgact | cactataggg | aaataagaga | gaaaagaaga | 60 |
| gtaagaagaa | atataagagc | caccatgtac | gtgagatttg | aggttcctga | ggacatgcag | 120 |
| aacgaagctc | tgagtctgct | ggagaaggtt | agggagagcg | taaggtaaa | gaaaggtacc | 180 |
| aacgagacga | caaaggctgt | ggagagggga | ctggcaaagc | tcgtttacat | cgcagaggat | 240 |
| gttgacccgc | ctgagatcgt | tgctcatctg | cccctcctct | gcgaggagaa | gaatgtgccg | 300 |
| tacatttacg | ttaaaagcaa | gaacgacctt | ggaagggctg | tgggcattga | ggtgccatgc | 360 |
| gcttcggcag | cgataatcaa | cgagggagag | ctgagaaagg | agcttggaag | ccttgtggag | 420 |
| aagattaaag | gccttcagaa | gtaagctgcc | ttctgcgggg | cttgccttct | ggccatgccc | 480 |
| ttcttctctc | ccttgcacct | gtacctcttg | gtctttgaat | aaagcctgag | taggaa | 536 |

<210> SEQ ID NO 2
<211> LENGTH: 620
<212> TYPE: DNA
<213> ORGANISM: Artificial Sequence
<220> FEATURE:
<223> OTHER INFORMATION: synthetic oligonucleotide

<400> SEQUENCE: 2

| | | | | | |
|---|---|---|---|---|---|
| ttggaccctc | gtacagaagc | taatacgact | cactataggg | aaataagaga | gaaaagaaga | 60 |
| gtaagaagaa | atataagagc | caccatgtac | gtgagatttg | aggttcctga | ggacatgcag | 120 |
| aacgaagctc | tgagtctgct | ggagaaggtt | agggagagcg | taaggtaaa | gaaaggtacc | 180 |
| aacgagacga | caaaggctgt | ggagagggga | ctggcaaagc | tcgtttacat | cgcagaggat | 240 |
| gttgacccgc | ctgagatcgt | tgctcatctg | cccctcctct | gcgaggagaa | gaatgtgccg | 300 |
| tacatttacg | ttaaaagcaa | gaacgacctt | ggaagggctg | tgggcattga | ggtgccatgc | 360 |
| gcttcggcag | cgataatcaa | cgagggagag | ctgagaaagg | agcttggaag | ccttgtggag | 420 |
| aagattaaag | gccttcagaa | gtaatacata | cttctttaca | ttccatacat | acttctttac | 480 |
| attccataca | tacttcttta | cattccatac | atacttcttt | acattccagc | tgccttctgc | 540 |
| ggggcttgcc | ttctggccat | gcccttcttc | tctcccttgc | acctgtacct | cttggtcttt | 600 |
| gaataaagcc | tgagtaggaa | | | | | 620 |

<210> SEQ ID NO 3
<211> LENGTH: 624
<212> TYPE: DNA
<213> ORGANISM: Artificial Sequence
<220> FEATURE:
<223> OTHER INFORMATION: synthetic oligonucleotide

<400> SEQUENCE: 3

| | | | | | |
|---|---|---|---|---|---|
| ttggaccctc | gtacagaagc | taatacgact | cactataggg | aaataagaga | gaaaagaaga | 60 |
| gtaagaagaa | atataagagc | caccatgtac | gtgagatttg | aggttcctga | ggacatgcag | 120 |
| aacgaagctc | tgagtctgct | ggagaaggtt | agggagagcg | taaggtaaa | gaaaggtacc | 180 |
| aacgagacga | caaaggctgt | ggagagggga | ctggcaaagc | tcgtttacat | cgcagaggat | 240 |

```
gttgacccgc ctgagatcgt tgctcatctg cccctcctct gcgaggagaa gaatgtgccg      300
tacatttacg ttaaaagcaa gaacgacctt ggaagggctg tgggcattga ggtgccatgc      360
gcttcggcag cgataatcaa cgagggagag ctgagaaagg agcttggaag ccttgtggag      420
aagattaaag gccttcagaa gtaaacaagc tttttgctcg tcttatacaa gcttttgct      480 cgtcttatac aagcttttg ctcgtcttat acaagctttt tgctcgtctt atgctgcctt      540
ctgcggggct tgccttctgg ccatgccctt cttctctccc ttgcacctgt acctcttggt      600
ctttgaataa agcctgagta ggaa                                            624

<210> SEQ ID NO 4
<211> LENGTH: 708
<212> TYPE: DNA
<213> ORGANISM: Artificial Sequence
<220> FEATURE:
<223> OTHER INFORMATION: synthetic oligonucleotide

<400> SEQUENCE: 4
ttggaccctc gtacagaagc taatacgact cactataggg aaataagaga gaaagaaga       60 gtaagaagaa atataagagc caccatgtac gtgagatttg aggttcctga ggacatgcag     120
aacgaagctc tgagtctgct ggagaaggtt agggagagcg gtaaggtaaa gaaaggtacc     180
aacgagacga caaaggctgt ggagagggga ctggcaaagc tcgtttacat cgcagaggat     240
gttgacccgc ctgagatcgt tgctcatctg cccctcctct gcgaggagaa gaatgtgccg     300
tacatttacg ttaaaagcaa gaacgacctt ggaagggctg tgggcattga ggtgccatgc     360
gcttcggcag cgataatcaa cgagggagag ctgagaaagg agcttggaag ccttgtggag     420
aagattaaag gccttcagaa gtaatacata cttctttaca ttccatacat acttctttac     480
attccataca tacttcttta cattccatac atacttcttt acattccaac aagcttttg      540 ctcgtcttat acaagcttt tgctcgtctt atacaagctt tttgctcgtc ttatacaagc     600
tttttgctcg tcttatgctg ccttctgcgg ggcttgcctt ctggccatgc ccttcttctc     660
tcccttgcac ctgtacctct tggtctttga ataaagcctg agtaggaa                  708

<210> SEQ ID NO 5
<211> LENGTH: 832
<212> TYPE: DNA
<213> ORGANISM: Artificial Sequence
<220> FEATURE:
<223> OTHER INFORMATION: synthetic oligonucleotide

<400> SEQUENCE: 5
ttggaccctc gtacagaagc taatacgact cactataggg aaaggtgggc gtgatccgaa       60
aggtgacccg gatctggggc gtgatccgaa aggtgacccg gaaagccacc atgggctcgg     120
tgtccaacca gcagtttgca ggtggctgcg ccaaggcagc ggagaaggcg ccagaggagg     180
cgccgcctga cgcggcccga gcggcagacg agccgcagct gctgcacggg gccggcatct     240
gtaagtggtt caacgtgcgc atggggttcg gcttcctgtc tatgaccgcc cgcgctgggg     300
tcgcgctcga ccccccggtg gacgtctttg tgcaccagag caagctgcac atggaagggt     360
tccgaagcct caaggagggt gaggcggtgg agttcacctt taagaagtct gccaagggtc     420
tggaatccat ccgtgtcact ggccctggtg gtgtgttctg tattgggagt gagcggcggc     480
caaaagggaa gaacatgcag aagcgaagat ccaaaggaga caggtgctac aactgcggtg     540
ggctagacca tcatgccaag gaatgcaagc tgccaccccca gcccaagaag tgccactttt     600
```

| gccaaagcat caaccatatg gtggcctcgt gtccactgaa ggcccagcag ggccccagtt | 660 |
| ctcagggaaa gcctgcctac ttccggagg aagaggaaga gatccacagc cctgccctgc | 720 |
| tcccagaagc ccagaattga gctgccttct gcggggcttg ccttctggcc atgcccttct | 780 |
| tctctcccctt gcacctgtac ctcttggtct ttgaataaag cctgagtagg aa | 832 |

```
<210> SEQ ID NO 6
<211> LENGTH: 1798
<212> TYPE: DNA
<213> ORGANISM: Artificial Sequence
<220> FEATURE:
<223> OTHER INFORMATION: synthetic oligonucleotide

<400> SEQUENCE: 6
```

| ttggaccctc gtacagaagc taatacgact cactataggg aaaggtgggc gtgatccgaa | 60 |
| aggtgacccg gatctggggc gtgatccgaa aggtgacccg gaaagccacc atgccgaagc | 120 |
| cacacagtga agcagggact gccttcattc agacccagca gctccatgca gccatggctg | 180 |
| acaccttcct ggaacacatg tgccgcctgg acattgactc tgcccccatc acggcccgca | 240 |
| acactggcat catttgtacc attgggcctg cttcccgatc tgtggagatg ctgaaggaga | 300 |
| tgattaagtc tggaatgaat gtggctcggc tgaatttctc tcatggaacc catgagtacc | 360 |
| atgcagagac catcaagaat gtccgtgaag ccacagaaag ctttgcatct gatcccattc | 420 |
| tctaccgtcc tgttgcggtg gctctggata caaagggacc tgagatccgg actggactca | 480 |
| tcaagggcag cggcaccgct gaggtggagc tgaagaaggg agccactctg aagatcaccc | 540 |
| tggacaacgc ttacatggag aagtgtgacg agaacatcct gtggctggac tacaagaaca | 600 |
| tctgcaaggt ggtggaggtg ggcagcaaga tctacgtgga cgatgggctc atctcactgc | 660 |
| aggtgaagga gaaaggcgct gacttcctgg tgacggaggt ggagaatggt ggctccttgg | 720 |
| gcagcaagaa gggcgtgaac ctgccgggcg ctgctgtgga tctccccgct gtgtcggaaa | 780 |
| aggacatcca ggacctgaag tttggggtgg agcaggatgt ggacatggtg tttgcatctt | 840 |
| tcatccgcaa ggcagccgac gtgcatgaag tcaggaaggt gctgggagag aagggcaaga | 900 |
| acatcaagat catcagcaaa atcgagaacc atgaaggcgt ccgcaggttt gatgagatct | 960 |
| tggaggccag tgatgggatc atggtggctc gtggtgacct gggcattgag attcctgcag | 1020 |
| agaaggtctt cctggctcag aagatgatga tcgggcgatg caaccgagct gggaagcctg | 1080 |
| tcatctgtgc cacacagatg ctggagagca tgatcaagaa gccacgcccc acccgtgctg | 1140 |
| aaggcagtga tgtggccaat gcagtcctgg atggagcaga ctgcatcatg ctgtctggag | 1200 |
| aaacagccaa gggggactac cctctggagg ctgttcgcat gcagcacctg attgcccgag | 1260 |
| aggcagaggc tgccatctac cacttgcagc tattcgagga actccgccgc ctggcgccca | 1320 |
| ttaccagcga ccccacagaa gctgccgccg tgggtgccgt ggaggcctcc ttcaagtgct | 1380 |
| gcagtggggc cattatcgtg ctcaccaagt ctggcaggag tgctcaccaa gtggccaggt | 1440 |
| accgccctcg ggctcctatc attgccgtga ctcgaaatcc ccagactgct cgccaggccc | 1500 |
| atctgtaccg tggcatcttc cctgtgctgt gtaaggatgc cgtgctgaat gcctgggctg | 1560 |
| aggatgtcga cctccgtgta aacttggcca tggatgttgg caaggcccga ggcttcttca | 1620 |
| agaagggaga tgtggtcatt gtgctgaccg ggtggcgccc tggctctgga ttcaccaaca | 1680 |
| ccatgcgtgt agtgcctgta ccttgagctg ccttctgcgg ggcttgcctt ctggccatgc | 1740 |
| ccttcttctc tcccttgcac ctgtacctct tggtctttga ataaagcctg agtaggaa | 1798 |

<210> SEQ ID NO 7
<211> LENGTH: 975
<212> TYPE: DNA
<213> ORGANISM: Artificial Sequence
<220> FEATURE:
<223> OTHER INFORMATION: synthetic oligonucleotide

<400> SEQUENCE: 7

```
ttggaccctc gtacagaagc taatacgact cactataggg aaaggtgggc gtgatccgaa        60
aggtgacccg gatctggggc gtgatccgaa aggtgacccg gaaagccacc atggtgagca       120
agggcgagga gctgttcacc ggggtggtgc ccatcctggt cgagctggac ggcgacgtaa       180
acggccacaa gttcagcgtg tccggcgagg gcgagggcga tgccacctac ggcaagctga       240
ccctgaagtt catctgcacc accggcaagc tgcccgtgcc ctggcccacc ctcgtgacca       300
ccctgaccta cggcgtgcag tgcttcagcc gctaccccga ccacatgaag cagcacgact       360
tcttcaagtc cgccatgccc gaaggctacg tccaggagcg caccatcttc ttcaaggacg       420
acggcaacta caagacccgc gccgaggtga agttcgaggg cgacaccctg gtgaaccgca       480
tcgagctgaa gggcatcgac ttcaaggagg acggcaacat cctggggcac aagctggagt       540
acaactacaa cagccacaac gtctatatca tggccgacaa gcagaagaac ggcatcaagg       600
tgaacttcaa gatccgccac aacatcgagg acggcagcgt gcagctcgcc gaccactacc       660
agcagaacac ccccatcggc gacggccccg tgctgctgcc cgacaaccac tacctgagca       720
cccagtccgc cctgagcaaa gaccccaacg agaagcgcga tcacatggtc ctgctggagt       780
tcgtgaccgc cgccgggatc actctcggca tggacgagct gtacaaggga gatccaaaaa       840
agaagagaaa ggtaggcgat ccaaaaaaga gagaaaggt aggtgatcca aaaaagaaga       900
gaaaggtata agctgccttc tgcggggctt gccttctggc catgcccttc ttctctccct       960
tgcacctgta cctct                                                         975
```

<210> SEQ ID NO 8
<211> LENGTH: 1021
<212> TYPE: DNA
<213> ORGANISM: Artificial Sequence
<220> FEATURE:
<223> OTHER INFORMATION: synthetic oligonucleotide

<400> SEQUENCE: 8

```
ttggaccctc gtacagaagc taatacgact cactataggg aaaggtgggc gtgatccgaa        60
aggtgacccg gatctggggc gtgatccgaa aggtgacccg gaaagccacc atggattcat       120
acctgctgat gtggggactg ctcacgttca tcatggtgcc tggctgccag gcagagctct       180
gtgacgatga cccgccagag atcccacacg ccacattcaa agccatggcc tacaaggaag       240
gaaccatgtt gaactgtgaa tgcaagagag gtttccgcag aataaaaagc gggtcactct       300
atatgctctg tacaggaaac tctagccact cgtcctggga caaccaatgt caatgcacaa       360
gctctgccac tcggaacaca acgaaacaag tgacacctca acctgaagaa cagaaagaaa       420
ggaaaaccac agaaatgcaa agtccaatgc agccagtgga ccaagcgagc cttccaggtc       480
actgcaggga acctccacca tgggaaaatg aagccacaga gagaatttat catttcgtgg       540
tggggcagat ggtttattat cagtgcgtcc agggatacag ggctctacac agaggtcctg       600
ctgagagcgt ctgcaaaatg acccacgga agacaaggtg acccagccc agctcatat       660
gcacaggtga atggagacc agtcagtttc caggtgaaga gaagcctcag gcaagccccg       720
aaggccgtcc tgagagtgag acttcctgcc tcgtcacaac aacagatttt caaatacaga       780
```

```
cagaaatggc tgcaaccatg gagacgtcca tatttacaac agatctccag gtagcagtgg      840
ccggctgtgt tttcctgctg atcagcgtcc tcctcctgag tgggctcacc tggcagcgga      900
gacagaggaa gagtagaaga acaatctagg ctgccttctg cggggcttgc cttctggcca      960
tgccttcttt ctctcccttg cacctgtacc tcttggtctt tgaataaagc ctgagtagga     1020
a                                                                      1021

<210> SEQ ID NO 9
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 9
ttggaccctc gtacagaagc taatacg                                           27

<210> SEQ ID NO 10
<211> LENGTH: 150
<212> TYPE: DNA
<213> ORGANISM: Artificial Sequence
<220> FEATURE:
<223> OTHER INFORMATION: synthetic oligonucleotide

<400> SEQUENCE: 10
tttttttttt tttttttttt tttttttttt tttttttttt tttttttttt tttttttttt       60
tttttttttt tttttttttt tttttttttt tttttttttt tttttttttt tttttttttt      120
tcttcctact caggctttat tcaaagacca                                        150

<210> SEQ ID NO 11
<211> LENGTH: 20
<212> TYPE: DNA
<213> ORGANISM: Mus musculus

<400> SEQUENCE: 11
gtctggagaa acagccaagg                                                   20

<210> SEQ ID NO 12
<211> LENGTH: 20
<212> TYPE: DNA
<213> ORGANISM: mus musculus

<400> SEQUENCE: 12
cggagttcct cgaatagctg                                                   20

<210> SEQ ID NO 13
<211> LENGTH: 20
<212> TYPE: DNA
<213> ORGANISM: mus musculus

<400> SEQUENCE: 13
ctgagacaga ggaggccaac                                                   20

<210> SEQ ID NO 14
<211> LENGTH: 20
<212> TYPE: DNA
<213> ORGANISM: Mus musculus

<400> SEQUENCE: 14
ttccgctctg tcttctggat                                                   20
```

```
<210> SEQ ID NO 15
<211> LENGTH: 20
<212> TYPE: DNA
<213> ORGANISM: Mus musculus

<400> SEQUENCE: 15
cagaacacca gcctcatcaa                                               20

<210> SEQ ID NO 16
<211> LENGTH: 20
<212> TYPE: DNA
<213> ORGANISM: Mus musculus

<400> SEQUENCE: 16
cccagtacct ccgaaagtca                                               20

<210> SEQ ID NO 17
<211> LENGTH: 21
<212> TYPE: DNA
<213> ORGANISM: Mus musculus

<400> SEQUENCE: 17
ctgccagtcc gaaaatggaa c                                             21

<210> SEQ ID NO 18
<211> LENGTH: 20
<212> TYPE: DNA
<213> ORGANISM: Mus musculus

<400> SEQUENCE: 18
cttcatccac cggggctatc                                               20

<210> SEQ ID NO 19
<211> LENGTH: 20
<212> TYPE: DNA
<213> ORGANISM: Mus musculus

<400> SEQUENCE: 19
attgagacag accccaaacg                                               20

<210> SEQ ID NO 20
<211> LENGTH: 20
<212> TYPE: DNA
<213> ORGANISM: Mus musculus

<400> SEQUENCE: 20
ttctggtttt ctggcagctt                                               20

<210> SEQ ID NO 21
<211> LENGTH: 19
<212> TYPE: DNA
<213> ORGANISM: Mus musculus

<400> SEQUENCE: 21
aagctgcggc tagaggtca                                                19

<210> SEQ ID NO 22
<211> LENGTH: 20
<212> TYPE: DNA
<213> ORGANISM: Mus musculus

<400> SEQUENCE: 22
ccctcccttt gatggctgag                                               20
```

<210> SEQ ID NO 23
<211> LENGTH: 21
<212> TYPE: DNA
<213> ORGANISM: Mus musculus

<400> SEQUENCE: 23
agacacacag gtgtgaaacc a                                              21

<210> SEQ ID NO 24
<211> LENGTH: 20
<212> TYPE: DNA
<213> ORGANISM: Mus musculus

<400> SEQUENCE: 24
atgagtcctg gtgtgggtct                                                20

<210> SEQ ID NO 25
<211> LENGTH: 20
<212> TYPE: DNA
<213> ORGANISM: Mus musculus

<400> SEQUENCE: 25
aggcagctct ggagtgagag                                                20

<210> SEQ ID NO 26
<211> LENGTH: 20
<212> TYPE: DNA
<213> ORGANISM: Mus musculus

<400> SEQUENCE: 26
cctggctcgc agattgtaag                                                20

<210> SEQ ID NO 27
<211> LENGTH: 20
<212> TYPE: DNA
<213> ORGANISM: Mus musculus

<400> SEQUENCE: 27
gggtacaaga aaccacccat                                                20

<210> SEQ ID NO 28
<211> LENGTH: 20
<212> TYPE: DNA
<213> ORGANISM: Mus musculus

<400> SEQUENCE: 28
gaggctgtgt cgactgagaa                                                20

<210> SEQ ID NO 29
<211> LENGTH: 20
<212> TYPE: DNA
<213> ORGANISM: Mus musculus

<400> SEQUENCE: 29
accaggacag ccaatacaag                                                20

<210> SEQ ID NO 30
<211> LENGTH: 20
<212> TYPE: DNA
<213> ORGANISM: Mus musculus

<400> SEQUENCE: 30
cctcggtcac tcatcttcac                                                20

```
<210> SEQ ID NO 31
<211> LENGTH: 21
<212> TYPE: DNA
<213> ORGANISM: Mus musculus

<400> SEQUENCE: 31
ttcgtgttcg agagcgattt g                                         21

<210> SEQ ID NO 32
<211> LENGTH: 22
<212> TYPE: DNA
<213> ORGANISM: Mus musculus

<400> SEQUENCE: 32
accttggaac tagatttgcc ag                                        22

<210> SEQ ID NO 33
<211> LENGTH: 21
<212> TYPE: DNA
<213> ORGANISM: Mus musculus

<400> SEQUENCE: 33
tttcggcctt gccagagcgt t                                         21

<210> SEQ ID NO 34
<211> LENGTH: 20
<212> TYPE: DNA
<213> ORGANISM: Mus musculus

<400> SEQUENCE: 34
gtggagtagc gagccgagcc                                           20

<210> SEQ ID NO 35
<211> LENGTH: 20
<212> TYPE: DNA
<213> ORGANISM: Mus musculus

<400> SEQUENCE: 35
gtcacccctc acgacttcat                                           20

<210> SEQ ID NO 36
<211> LENGTH: 20
<212> TYPE: DNA
<213> ORGANISM: Mus musculus

<400> SEQUENCE: 36
ttccagttgc aatcatcgac                                           20

<210> SEQ ID NO 37
<211> LENGTH: 20
<212> TYPE: DNA
<213> ORGANISM: Mus musculus

<400> SEQUENCE: 37
aaggtgcctg tgtgtgaacc                                           20

<210> SEQ ID NO 38
<211> LENGTH: 19
<212> TYPE: DNA
<213> ORGANISM: Mus musculus
```

```
<400> SEQUENCE: 38
gtcagcccca tcatctgcg                                                19

<210> SEQ ID NO 39
<211> LENGTH: 21
<212> TYPE: DNA
<213> ORGANISM: Mus musculus

<400> SEQUENCE: 39
agtccctgcc ctttgtacac a                                             21

<210> SEQ ID NO 40
<211> LENGTH: 19
<212> TYPE: DNA
<213> ORGANISM: Mus musculus

<400> SEQUENCE: 40
cgatccgagg gcctcacta                                                19

<210> SEQ ID NO 41
<211> LENGTH: 20
<212> TYPE: DNA
<213> ORGANISM: Mus musculus

<400> SEQUENCE: 41
aaccttagtg gggtgctgtg                                               20

<210> SEQ ID NO 42
<211> LENGTH: 20
<212> TYPE: DNA
<213> ORGANISM: Mus musculus

<400> SEQUENCE: 42
aaggcacaaa ctcgcatctt                                               20

<210> SEQ ID NO 43
<211> LENGTH: 20
<212> TYPE: DNA
<213> ORGANISM: Mus musculus

<400> SEQUENCE: 43
ccagctacat cgcctacctc                                               20

<210> SEQ ID NO 44
<211> LENGTH: 20
<212> TYPE: DNA
<213> ORGANISM: Mus musculus

<400> SEQUENCE: 44
tggttttctt gtcgttgctg                                               20

<210> SEQ ID NO 45
<211> LENGTH: 20
<212> TYPE: DNA
<213> ORGANISM: Mus musculus

<400> SEQUENCE: 45
cacagtgcct gaaatcacca                                               20

<210> SEQ ID NO 46
<211> LENGTH: 20
<212> TYPE: DNA
```

<213> ORGANISM: Mus musculus

<400> SEQUENCE: 46
ctggctgtgt ttgtcaatgg                                              20

<210> SEQ ID NO 47
<211> LENGTH: 20
<212> TYPE: DNA
<213> ORGANISM: Mus musculus

<400> SEQUENCE: 47
tccagcctga acatctaccc                                              20

<210> SEQ ID NO 48
<211> LENGTH: 20
<212> TYPE: DNA
<213> ORGANISM: Mus musculus

<400> SEQUENCE: 48
ccatagtcac caaggctgct                                              20

<210> SEQ ID NO 49
<211> LENGTH: 20
<212> TYPE: DNA
<213> ORGANISM: Mus musculus

<400> SEQUENCE: 49
tggctcctac tggacctctc                                              20

<210> SEQ ID NO 50
<211> LENGTH: 20
<212> TYPE: DNA
<213> ORGANISM: Mus musculus

<400> SEQUENCE: 50
tgccttttaa gatgcagcag                                              20

<210> SEQ ID NO 51
<211> LENGTH: 20
<212> TYPE: DNA
<213> ORGANISM: Mus musculus

<400> SEQUENCE: 51
cagaacacca gcctcatcaa                                              20

<210> SEQ ID NO 52
<211> LENGTH: 20
<212> TYPE: DNA
<213> ORGANISM: Mus musculus

<400> SEQUENCE: 52
gctccttctt cagctcctca                                              20

<210> SEQ ID NO 53
<211> LENGTH: 21
<212> TYPE: DNA
<213> ORGANISM: Mus musculus

<400> SEQUENCE: 53
ctctgctgcc tcctggcttc t                                            21

<210> SEQ ID NO 54
<211> LENGTH: 21

```
<212> TYPE: DNA
<213> ORGANISM: Mus musculus

<400> SEQUENCE: 54
cgaggcggat cacaagcaat a                                              21

<210> SEQ ID NO 55
<211> LENGTH: 19
<212> TYPE: DNA
<213> ORGANISM: Mus musculus

<400> SEQUENCE: 55
tcaatgggcg ggggtcgtt                                                 19
```

CELL-SPECIFIC EXPRESSION OF MODRNA

CROSS-REFERENCE TO RELATED APPLICATIONS

This application is a continuation of PCT/US2017/052035 filed Sep. 18, 2017 and published on Mar. 22, 2018 as WO 2018/053414, which claims priority to U.S. provisional application No. 62/395,701 filed Sep. 16, 2016, the contents of which are hereby incorporated by reference into the present application.

SEQUENCE LISTING

The instant application contains a Sequence Listing, created on Aug. 9, 2021; the file, in ASCII format, is designated H2119831.txt and is 17.9 kilobytes in size. The file is hereby incorporated by reference in its entirety into the instant application.

TECHNICAL FIELD

The present disclosure relates generally to a platform for the cell-specific expression of therapeutic proteins in vitro, ex vivo and in vivo, using a cell-specific transcriptional regulatory system based on cell-specific miR override of gene expression suppression.

BACKGROUND OF THE DISCLOSURE

Chemically modified messenger RNA (modRNA) is a therapeutic strategy that enables the cellular machinery to produce genes of interest without modifying the genome. Thus, modRNA avoids several of the problems that have arisen with conventional gene therapy, including lack of genomic integration, persistence of expression, immunogenicity, difficulty in scalability and production, need for life-long monitoring for tumorigenesis and other adverse clinical outcomes, and the potential for vector escape into the systemic circulation and long-term expression elsewhere in the body.

modRNA has considerable potential as a therapy for disease. Delivery of a cell cycle inducer via modRNA, for example, would trigger growth of beta cells in individuals with diabetes or restore proliferation of cardiomyocytes following myocardial infarction or heart failure. Diabetic neuropathy may be lessened by the ability to deliver genes encoding nerve growth factor. Additionally, with the advent of genome editing technology, CRISPR/Cas9 or transcription activator-like effector nuclease (TALEN) transfection will be safer if delivered in a transient and cell-specific manner.

However, none of the available transfection reagents for modRNA offers both a high level of gene expression and the ability to target any cell of interest. For example, a common in vivo transfection reagent is in vivo-jetPEI® (Polyplus-transfection® SA, Illkirch, France), which is a polymer based reagent that complexes with modRNA to form nanoparticles. However, in vivo-jetPEI primarily targets lung tissue in vivo and significantly lowers transfection efficacy compared to naked modRNA.

Therefore, what is needed is a modRNA-based gene delivery system that achieves a high level of gene expression exclusivity in a cell of interest.

SUMMARY OF THE DISCLOSURE

The present disclosure provides an expression regulatory platform for cell-specific transcription based on the exploitation of a repressor RNA-binding protein/k-motif interaction coupled with cell-specific miR override of the repressor function to control expression of a delivered modRNA in a cell-specific fashion. RNA-binding proteins such as the archaeal protein L7Ae and eukaryotic homologs thereof such as L30e recognize a distinctive RNA motif, the kink-turn (k-turn or k-motif as referred to herein). By incorporating the k-motif into a first construct that encodes a gene of interest (GOI) and including a recognition element for a cell-specific miR in a second construct that encodes the RNA-binding protein, suppression of expression of the GOI is overridden when the two constructs are co-transfected into the appropriate cell type. The platform incorporates modified mRNA The present disclosure, therefore, relates to a method for achieving cell-specific expression of a modRNA of a gene of interest (GOI) the expression of which is desired only in the cell of interest. In one aspect, the disclosure describes an expression regulatory system for cell-specific transcription, the system comprising a first nucleic acid that encodes (1) a cell-specific microRNA (miR) recognition element, and (2) a translation suppressor protein; and a second nucleic acid that encodes (1) a suppressor protein interaction motif, for example a K-motif, downstream of its 5'UTR that binds the translation suppressor protein, and (2) a gene that encodes a protein of interest. The nucleic acids are modRNA.

By swapping out the miR recognition element, cell specificity can be modulated, making the system adaptable to other cell types.

In another aspect, the present disclosure relates to short-term expression of cardiomyocyte (CM)-specific modRNA of candidate genes, such as cell cycle inducer genes, the expression of which reactivates CM regeneration, which is important following post-myocardial infarction or in heart failure settings. The method is based on the observation that cell cycle inducer genes, for example, Lin28 and Pkm2, delivered as modRNA using the cell-specific delivery system of the disclosure following MI significantly induces CM and non-CM proliferation. Since increased non-CM proliferation can lead to enhanced cardiac scarring, it was necessary to develop a CM-specific modRNA that allows expression of genes only in cardiomyocytes.

The present disclosure describes CM-specific modRNA that allows modRNA translation exclusively in CMs. In one embodiment, CM-specific Lin28 or Pkm2 modRNA expression results in significant CM proliferation without significantly changing non-CM proliferation. In another embodiment, based on CM-specific modRNA, a novel lineage tracing adult mouse model that is based on co-expression destabilized Cre recombinase and candidate genes in Rosa26$^{tdTomato}$ using CM-specific modRNA was developed.

In one aspect, the disclosure relates to an expression regulatory system for cardiomyocyte-specific expression comprising a first nucleic acid that encodes a recognition element for microRNA (miR recognition elements serve as an anti-miR approach) that binds specifically to a target cardiomyocyte miR, and prevents the translation of a suppressor protein (L7Ae); and a second nucleic acid that comprises a gene of interest and a kink-turns motif (K-motif) that are bound by the suppressor protein (L7Ae). Binding of L7Ae to the K motif inhibits the expression of the genes that had the K motif.

In one embodiment of the translational regulatory system, the target cardiomyocyte miR is selected from the group consisting of miR1, miR29, miR126, miR133a, miR199, miR208a and miR378. In another embodiment, the target cardiomyocyte miR is selected from the group consisting of miR1, miR 208a and miR1 in combination with miR208a.

In one embodiment of the expression regulatory system, the suppressor protein is L7Ae and the protein interaction motif is K-motif. L7Ae is an RNA binding protein that represses translation of the targeted transcript. L7Ae targets a specific sequence called the k-motif or k-turn. Accordingly, the k-motif is built into the nucleic acid of the pair that encodes the GOI. Ordinarily, when the other nucleic acid of the pair that encodes L7Ae is expressed normally, L7Ae is able to bind to the k-motif, thereby repressing expression of the GOI encoded by that nucleic acid.

In an embodiment of the present system, the nucleic acid encoding L7Ae also contains a cell-specific miR recognition element. When expressed in the appropriate cell, cell-specific miR binds the miR recognition element to halt expression of L7Ae, eliminating suppression of the GOI on the other nucleic acid.

In one embodiment of the translational regulatory system, the protein of interest is a reporter protein or other gene of interest. In one embodiment of the translational regulatory system, the reporter protein or selection marker is a fluorescent protein, an antibiotic resistance marker or other gene of interest. In one embodiment of the translational regulatory system, the reporter protein or selection marker is selected from the group consisting of green fluorescence protein (GFP), inactive human CD25 (ihCD25). In one embodiment of the transcriptional/translational regulatory system of the disclosure, the protein of interest is a cell cycle inducer protein. In one embodiment of the translational regulatory system, the cell cycle inducer protein is selected from the group consisting of Lin28, Pkm2, and Cyclin D2. In one embodiment of the transcriptional regulatory system, said first nucleic acid comprises the nucleotide sequence of SEQ ID NO: 2, SEQ ID NO: 3, or SEQ ID NO: 4. In one embodiment of the transcriptional regulatory system, said second nucleic acid comprises the nucleotide sequence of SEQ ID NO: 5, SEQ ID NO: 6, SEQ ID NO: 7 or SEQ ID NO: 8.

In one aspect, the disclosure relates to a composition comprising first and second modified RNAs (modRNAs), wherein said first modRNA is an expression product of the first nucleic acid of claim 1, 2 or 3 and the second modRNA is an expression product of the second nucleic acid.

In one aspect, the disclosure relates to a method for expressing a protein in cardiomyocytes (CMs), the method comprising contacting said CMs with a modRNA encoding an miR recognition element specific for a cardiomyocyte miR target, wherein the modRNA comprises the nucleotide sequence of SEQ ID NO: 2, SEQ ID NO: 3, or SEQ ID NO: 3.

In one aspect, the disclosure relates to a vector comprising first and second nucleic acids as described herein.

In one aspect, the disclosure relates to a transcriptional/translational regulatory kit comprising the first and second nucleic acids as described herein or a vector comprising first and second nucleic acids as described herein.

In one aspect, the disclosure relates to a method for inducing/reactivating proliferation of cardiomyocytes following myocardial infarction (MI), the method comprising contacting said cardiomyocytes or a portion of said myocytes with a first modRNA that encodes a cardiomyocyte-specific miR and a second modRNA that encodes a cell cycle inducer gene.

In one aspect, the disclosure relates to the disclosed method, wherein the cell cycle inducer gene is selected from the group consisting of Lin28, Pkm2 and Cyclin D2.

DETAILED DESCRIPTION OF THE DISCLOSURE

Figure 1:
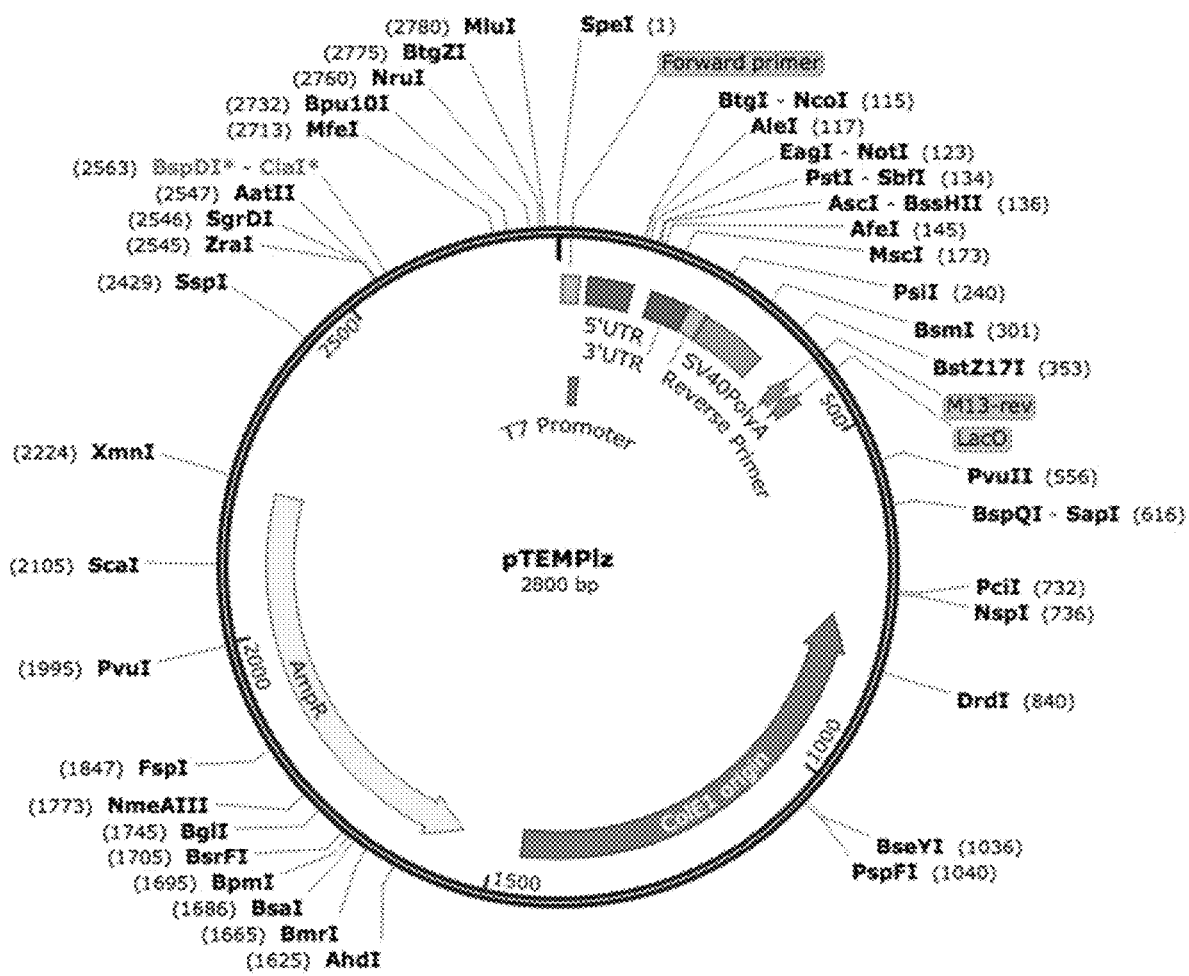
FIG. 1 shows a plasmid map of pTEMPLZ used in generating the modRNA of the disclosure.

All patents, published applications and other references cited herein are hereby incorporated by reference into the present application. Methodologies used in developing the present invention are well known to those of skill in the art unless otherwise indicated.

In the description that follows, certain conventions will be followed as regards the usage of terminology. In general, terms used herein are intended to be interpreted consistently with the meaning of those terms as they are known to those of skill in the art. Some definitions are provide purely for the convenience of the reader.

The term "recognition element for miRNA" or "miRNA recognition element refers to single-stranded RNA-based oligonucleotides that are designed to bind endogenous miRNA and inhibit the expression of a construct containing the recognition element when it is introduced into cells.

The term "miRNA" refers to sequences that are complementary to mRNA that are involved in the cleavage of RNA or the suppression of the translation. Endogenous mature miRNAs function as part of the RNA-induced complex, which has the capacity to post-transcriptionally regulate mRNAs that have sequences with partial complementarity to the bound miRNA. Through the hybridization of the anti-miRNA sequence to the miRNA sequence, the function of the miRNA sequence is neutralized by preventing its selective binding to the target.

The term "modRNA" refers to a synthetic modified RNA that can be used for expression of a gene of interest. Chemical modifications made in the modRNA, for example substitution of pseudouridine for uridine, stabilize the molecule and enhance transcription. Additionally, unlike delivery of protein agents directly to a cell, which can activate the immune system, the delivery of modRNA can be achieved without immune impact. The use of modRNA for in vivo and in vitro expression is described in more detail in for example, WO 2012/138453.

The term "inactive human CD25" (ihCD25) refers to a truncated interleukin-2 receptor that has only the extracellular domain and is unable to signal into the cell. Other species, for example, inactive mouse CD25 may also be used in the disclosed method.

The present disclosure relates to methodology for achieving cell-specific expression of a modRNA encoding a gene of interest (GOI) the expression of which is desired in a cell of interest. In one aspect, the disclosure describes an expression regulatory system for cell-specific transcription, the system comprising a first nucleic acid having a 5' untranslated region (UTR) and a 3' UTR, where the nucleic acid encodes (1) a cell-specific microRNA (miR) recognition element upstream of its 3'UTR, and (2) a translation suppressor protein; and a second nucleic acid having a 5' UTR and a 3' UTR that encodes (1) a suppressor protein interaction motif, for example a K-motif, downstream of its 5'UTR that binds the translation suppressor protein, and (2) a gene that encodes a protein of interest.

Current treatments for MI address the consequences of myocyte loss, but are not effective in enhancing myocardial repair of lost heart muscle (3, 5). Recently, it was demonstrated that one day adult mammalian heart cells (mice) can regenerate heart themselves via CMs proliferation (7). Examining the genetic differences between the regenerative and the non-regenerative stages it was found that the most differentially expressed gene between these stages belong to mitosis and cell cycle categories (7).

Modified mRNA (modRNA) has emerged as an effective and safe tool for somatic gene transfer, and has been successfully used by us and others for gene delivery to the heart.[10,12-15] Here we show that Pyruvate Kinase Muscle Isozyme M2 (Pkm2), a pro-proliferative factor, frequently dysregulated in cancer,[16,17] is highly expressed in regenerative fetal and early neonatal CMs, but not in adult CMs. Restoration of Pkm2 levels using the modRNA delivery of the disclosure exclusively into adult CMs ($_{cms}$Pkm2) post-MI significantly and exclusively induced CMs proliferation, and was associated with improved cardiac function, reduced scar size, increased heart to body weight ratio, reduced CMs size, reduced apoptosis and increased capillary density. Those regenerative processes translated into increased long-term survival post-MI. Using lineage tracing and isolation of Pkm2-transfected CMs followed by gene expression analysis post-MI we show an increase in number of Pkm2-transfected CMs colonies and the potential involvement of key downstream effectors of the pro-proliferative cytoplasmic (via the pentose phosphate pathway (PPP)[18,19]) and nuclear (via trans-activation of β-catenin and Hif1α[20,21]) functions of Pkm2. Our results show that a short pulse of a pro-proliferative gene, using a highly translatable, clinically adaptable platform is sufficient to induce CM proliferation and cardiac regeneration. Those findings underline the therapeutic potential of $_{cms}$Pkm2 modRNA in cardiac disease.

Reactivation of CMs proliferation has been a key element in cardiac regeneration strategies. Zebrafish and newt cardiac regeneration is mostly mediated by CMs proliferation[3,5,7,8]. In mammals fetal development, CMs proliferation is a distinct pathway for heart growth and regeneration[9,22]. It has been shown that after injury adult CMs upregulate a subset of fetal genes suggesting that adult CM are not terminally differentiated and possess some degree of cell plasticity[4,9]. Adult mammalian CMs can divide in vitro and in vivo and this ability can be stimulated by upregulating pro-proliferative genes[9,22-33]. Over the years, several publications have shown that reactivation of adult CMs cell cycle re-entry is possible via proteins[23,24,26,30,34], viruses[26,30,31,35] or transgenic mouse models of pro-proliferation genes[25,28,33]. Protein administration for the purpose of cell cycle induction is challenging due to the very short half-life, the difficulty of local administration, lack of CMs specificity and the inability to deliver intracellular genes, such as transcription factors. The cardiac specific adeno-associated virus ($_{CMS}$AAV) vector is not immunogenic and used in many heart studies but has a very long and sustained expression time that may lead to increased uncontrolled CMs size and cardiac hypertrophy and arrhythmia. Although transgenic mice can be used in CM-specific and transient way, they are not clinically-relevant for gene delivery. Challenges with current approaches highlight the need for an efficient gene delivery approach that can safely, and locally deliver cell cycle inducer genes to the CMs, with a transient, efficient, and controlled manner. Pyruvate Kinase Muscle Isozyme M2 (Pkm2) is a cell cycle inducer. During development, Pkm2 is expressed in many adult tissues including the spleen and lung, however during adulthood Pkm2 is strictly expressed in proliferating cells with high anabolic activity[16,17]. Pkm2 was found to increase adult cell and cancer cells proliferation, angiogenesis and prevent apoptosis caused by oxidative stress[18,20,36-42]. Pkm2 exerts its functions by its two distinct functions: In the cytoplasm, Pkm2 shifts the metabolic fate from glycolysis to pentose phosphate pathway (PPP) by reducing the conversion of phosphoenolpyruvate to pyruvate[18,19]. This leads to the accumulation of galactose, a glycolysis intermediate, and activation of PPP via Glucose-6-phosphate dehydrogenase (G6pd)[43-45]. The PPP pathway activation leads to the synthesis of nucleotides, amino acids, and lipids and the production of reduced NADPH, increase nitric oxide synthase and DNA repair[38,39,41,46-48]. In addition, Pkm2 has a role also in the nucleus. Pkm2 directly interacting with the transcription factors β-catenin and Hif1α. This interaction promotes the expression of genes such as in Ccdn1, c-Myc and Vegfa, and Bcl2[20,21] See summary of Pkm2 role in proliferative or cancer cells in FIG. 5 (S1).

Several studies indicate that cell cycle inducer genes can induce CMs to proliferate (8-22). However, activation of these genes for long periods in CMs may lead to CMs hypertrophy and in some cases to hypertrophic cardiomyopathy and HF(14). In addition, systemic delivery of cell cycle inducer genes can lead to uncontrolled cell growth of non-CM cells in the heart and throughout the body, and can raise safety issues.

Figure 2:
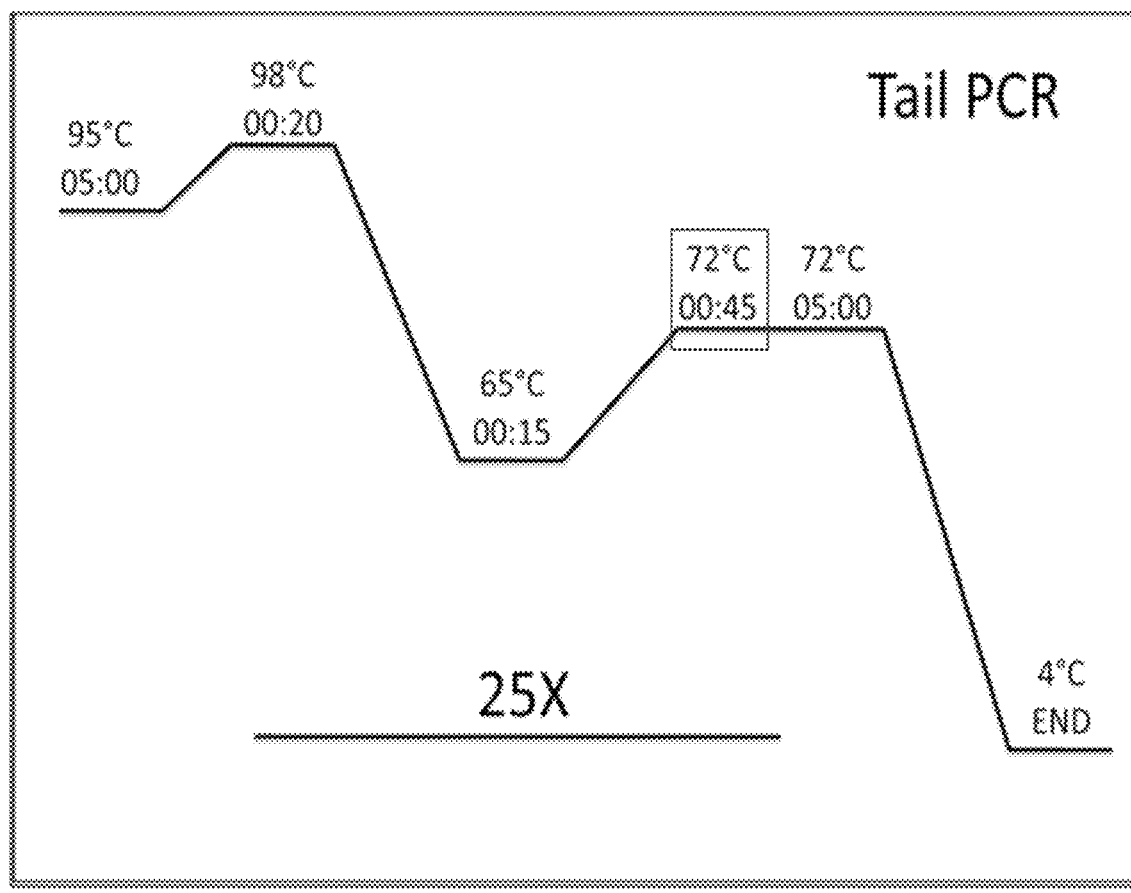
FIG. 2 shows in graphic (top panel) and table form (bottom panel) the PCR settings for synthesizing DNA tailed template. Shown in box is the elongation step that must be set based on the size of the sequence insert. Elongation step requires 30 sec per KB of ORF insert. PCR setting is based on manufacturer instructions from 2× KAPA HiFi HotStart ReadyMix kit.
Figure 3A:
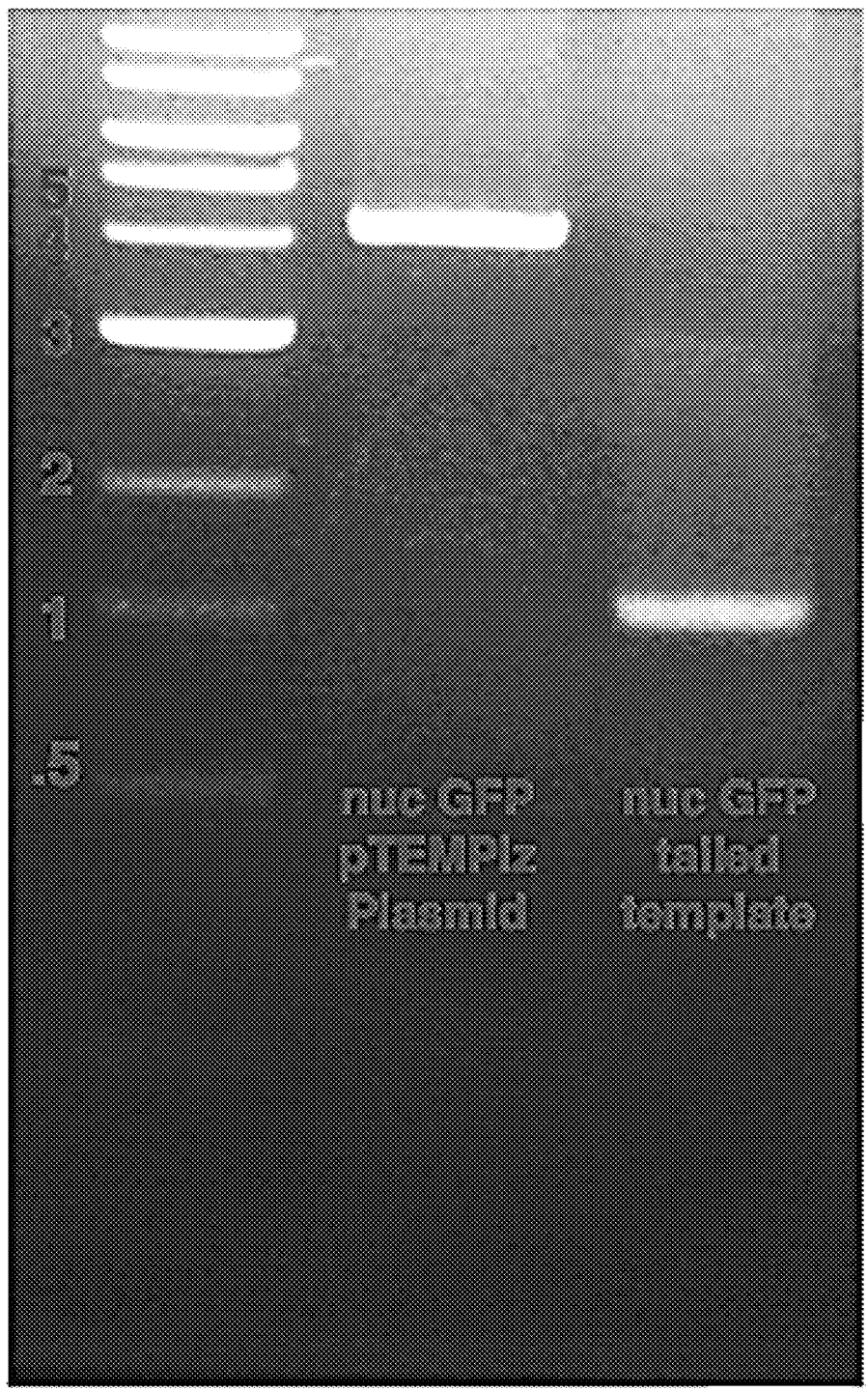
FIGS. 3A-3C show the results of the quality control analysis for modRNA synthesis. A 1% agarose gel determining correct size of the plasmid pTEMPLZ with ORF insert and tailed DNA template for IVT. B Ideal Nanodrop result of final modRNA product. Ideal concentration is between 15-20 ug/ul. 260/280 values closer to 2 indicate purity. C Bioanalyzer result for quality control of synthesized modRNA.
Figure 6A:
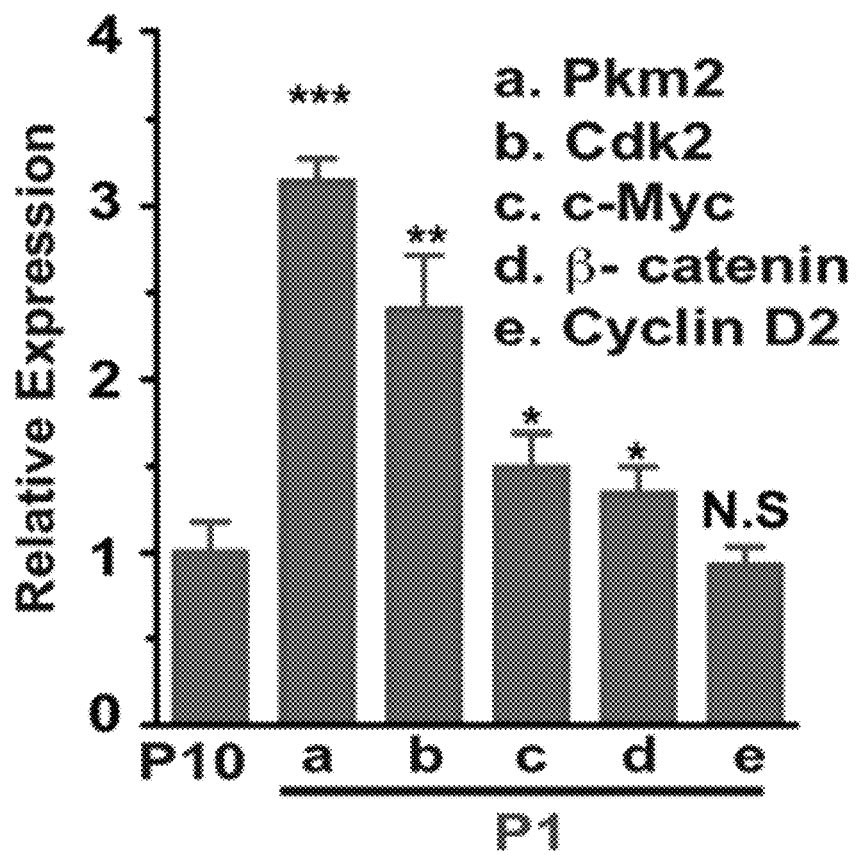
FIGS. 6A-6H show that Pkm2 expression in adult CMs induces proliferation after MI. A Relative expression of Pkm2 measured by qRT-PCR in mice' hearts 1 or 10 days after birth. B Experimental plan for immunostaining of Pkm2 or α-Actinin (CMs marker) at different stages of mouse heart development. C Representative images of Pkm2 expression at different stages of mouse heart developmental. D pharmacokinetics of Pkm2 expression post modRNA delivery in vivo. E Experimental timeline for measuring the effect of Pkm2 on CMs proliferation F A Representative image of DNA synthesis (BrdU$^+$) in CMs (α-Actinin$^+$) and non-CMs cells (α-Actinin$^-$) 7 days post-MI. G-H Quantification of hallmark proliferation markers in CMs F or non-CMs G in adult mice 7 days post-MI. Results represent 2 independent experiments (n=4); white arrow heads point to CMs; yellow arrow heads point to non-CMs, *, P<0.001, , P<0.01, two-tailed student t-test, Scale bar 10 μm.
Figure 6B:
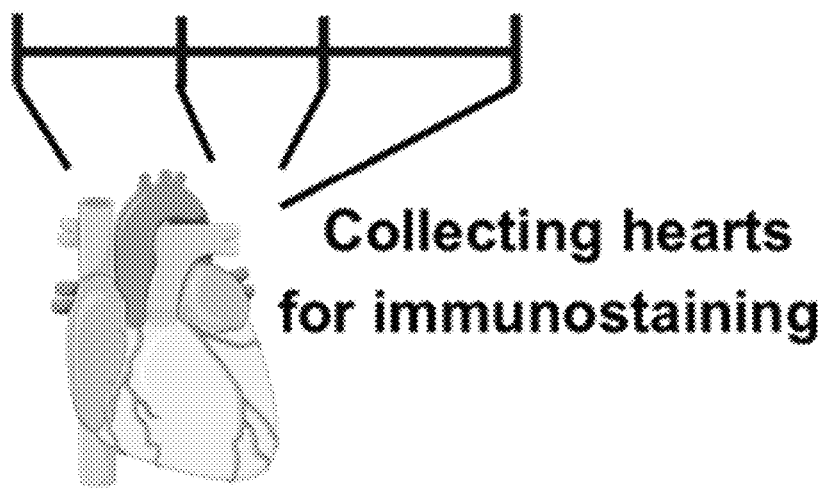
Figure 6C:
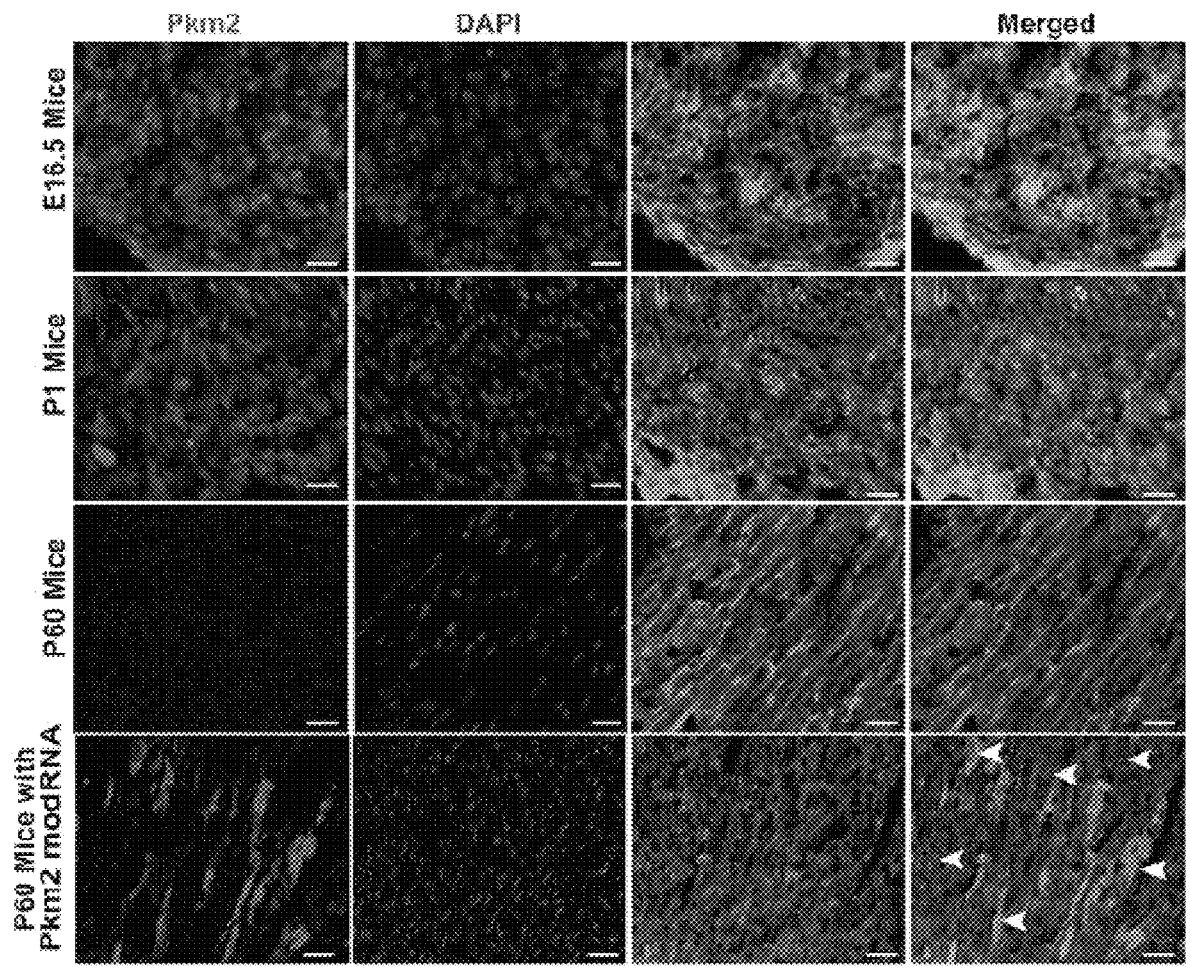
Figure 6D:
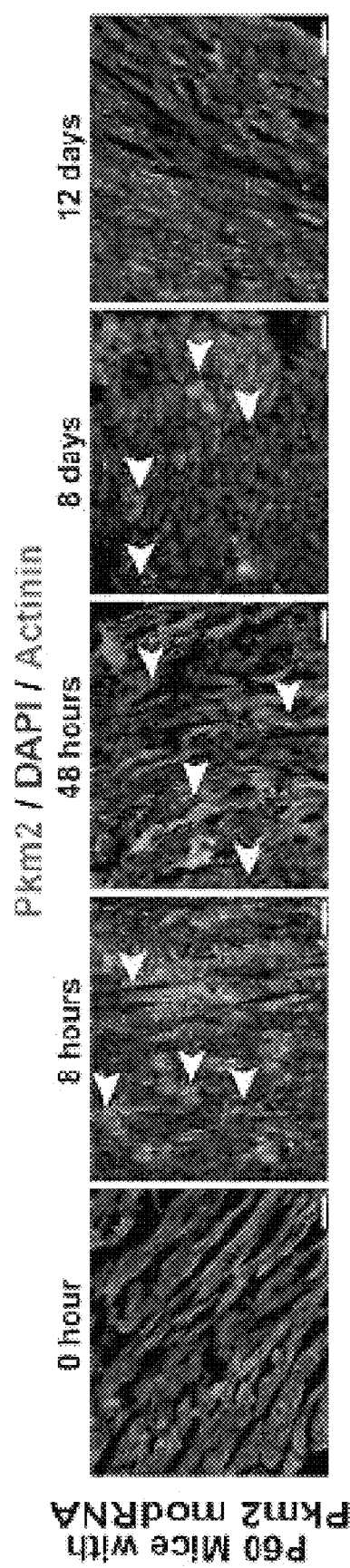
Figure 6E:
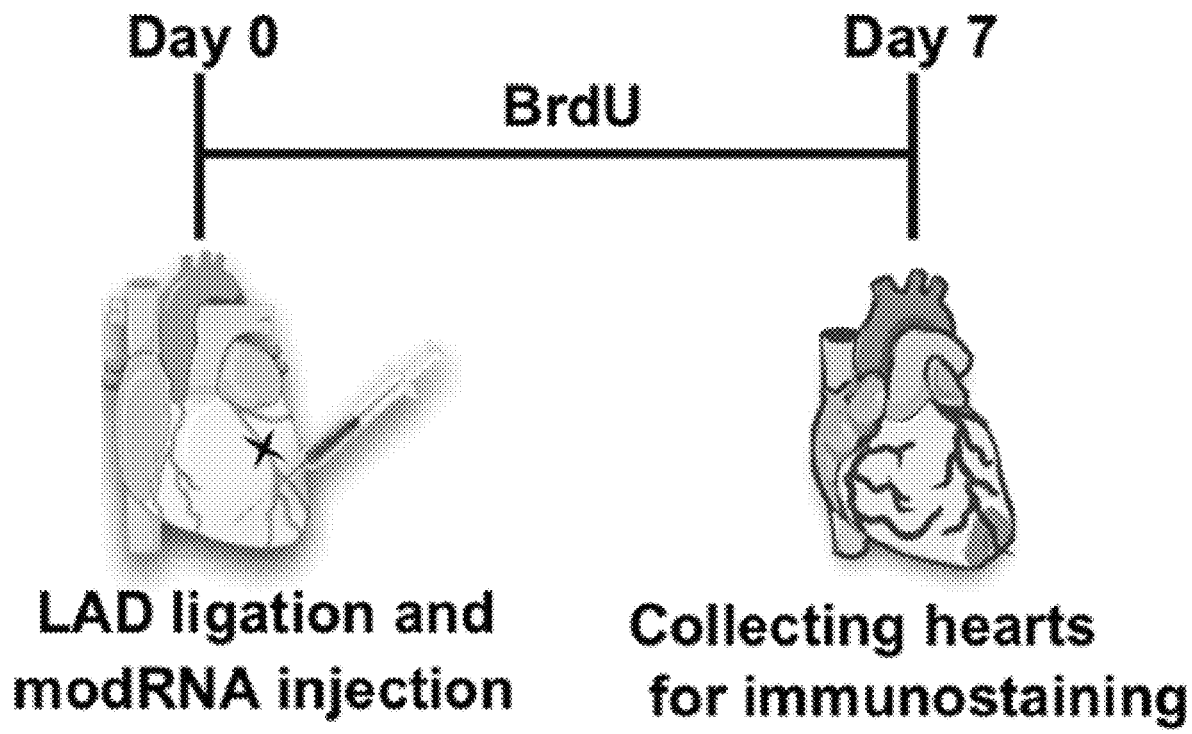
Figure 6F:
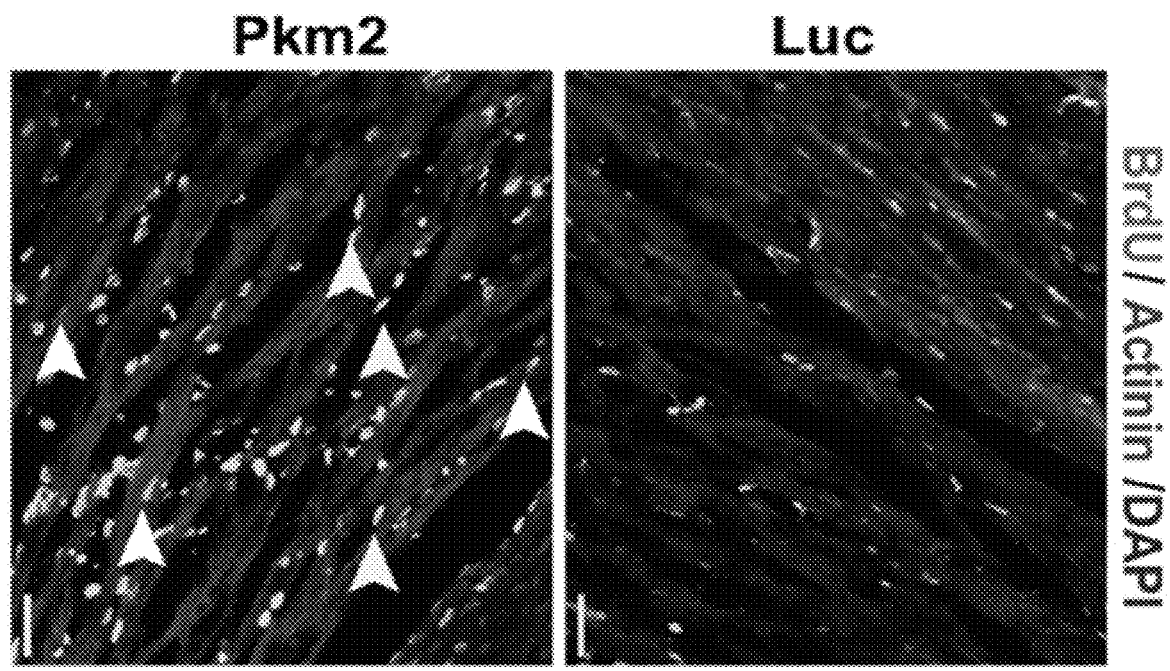
Figure 6G:
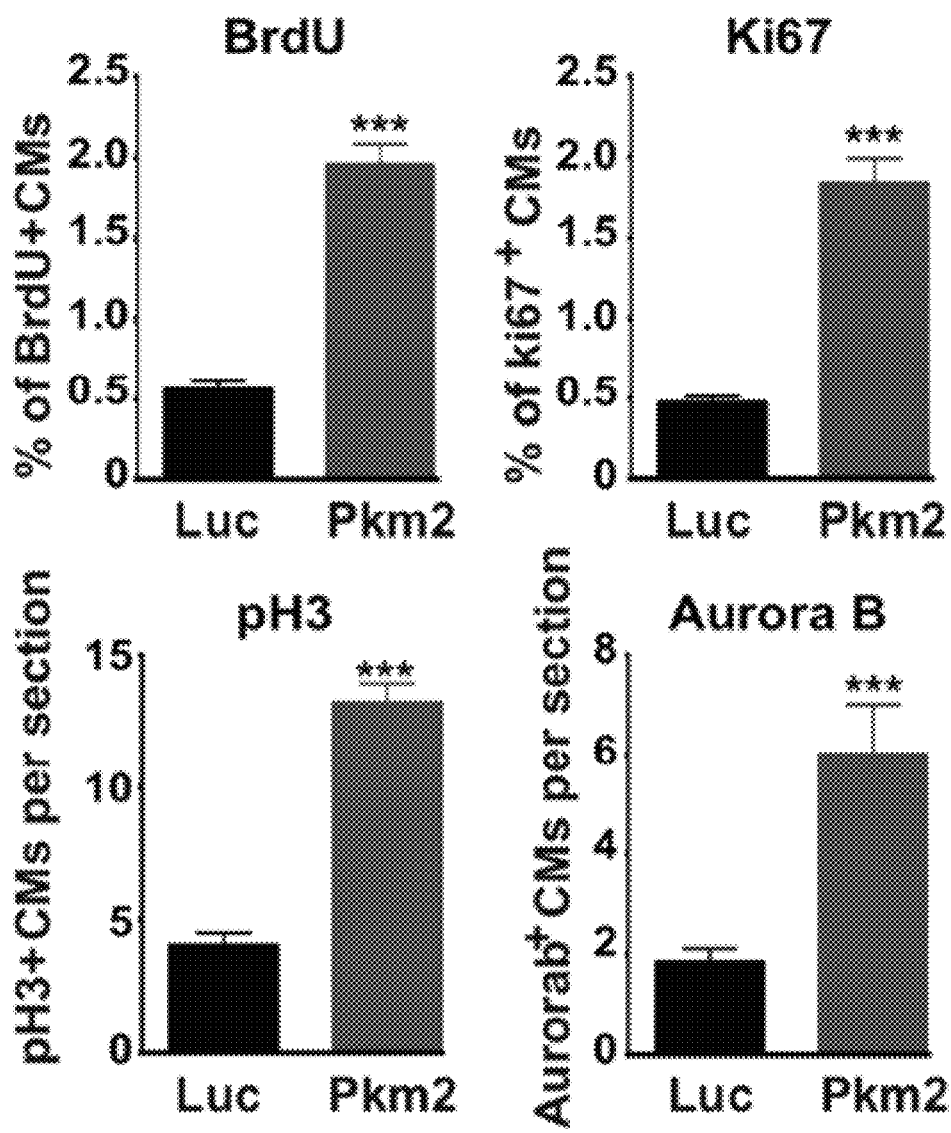
Figure 6H:
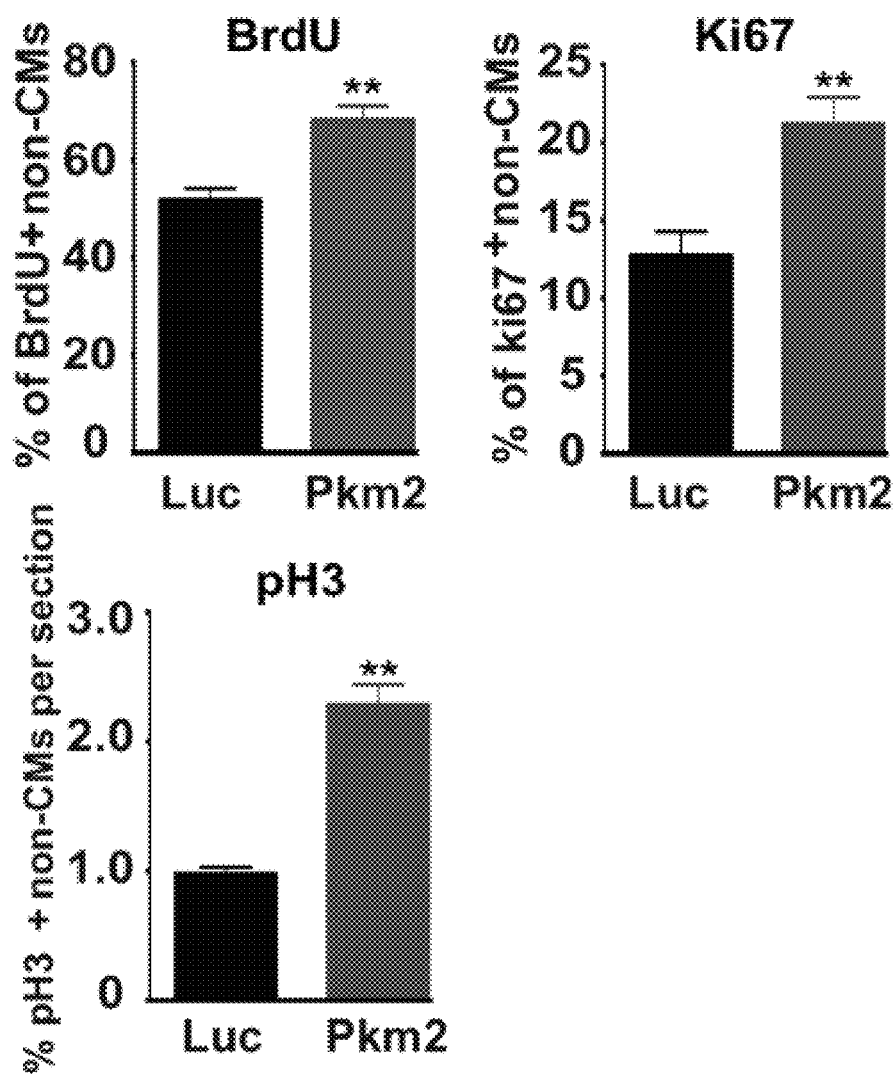
Figure 7A:
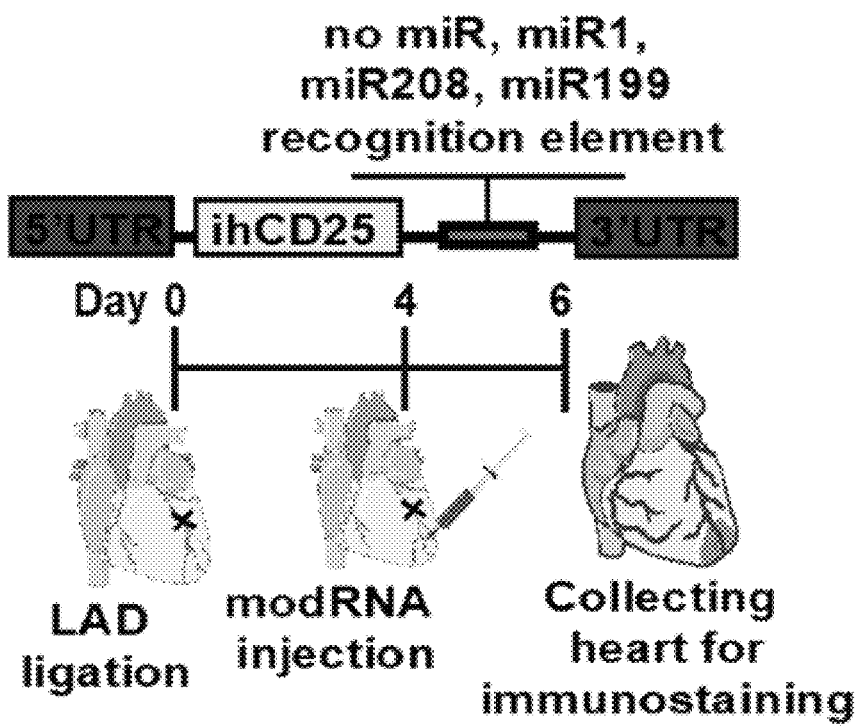
FIGS. 7A-7K show the design and function of $_{cms}$-modRNA in vivo. A Construct design and experimental timeline used to identify $_{cms}$miRs. B Immunostaining images of ihCD25 modRNA expression (red) with or without recognition elements for different miRs post transfection. C Quantification of the experiment in c. D modRNAs constructs design used for $_{cms}$Cre or $_{cms}$nGFP modRNAs delivery in vivo. E-F nGFP-K modRNA (green) transfected alone or co-transfected miR1-208, 4 days post-MI. E Representative images of hearts 7 days post-MI. F Transfection efficiency with different ratios of nGFP-K and miR1-208. Rosa26$^{mTmG}$ mice co-transfected with Cre-K+miR1-208. G Co-transfection of Cre-K+miR1-208. Red: Troponin I. H Quantification of the experiment in g. I Experimental timeline for evaluation of $_{cms}$Pkm2 modRNA effect on proliferation. Quantification of hallmark proliferation markers in CMs J or non-CMs K 7 days post-MI. Results represent 2 independent experiments (n=3 mice); **, P<0.0001, *, P<0.001, **, P<0.01, N.S, Not Significant, two-tailed student t-test (f) or One-way ANOVA, Bonferroni post-hoc test (j,c,k). Scale bar 10 µm or 50 µm in c and for h, respectively.
Figure 7B:
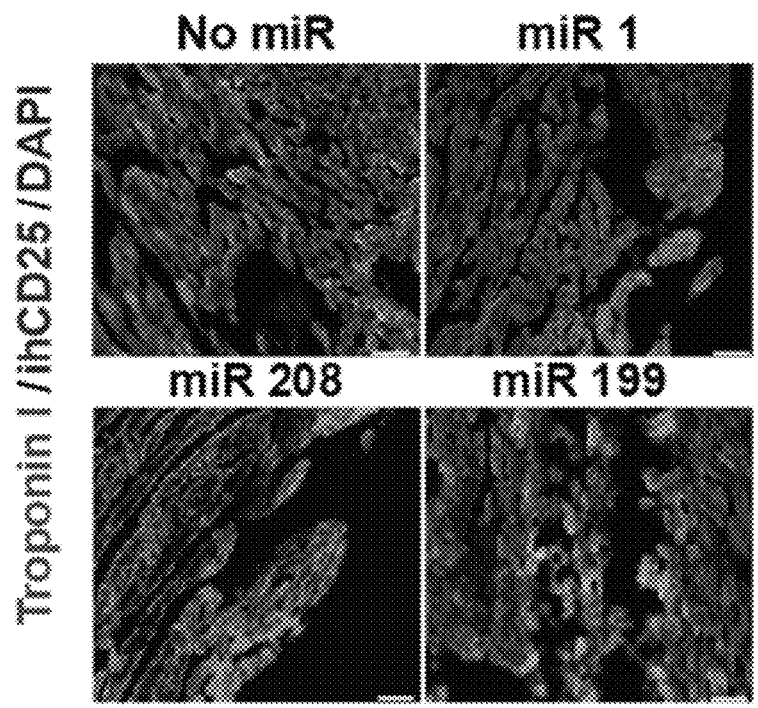
Figure 7C:
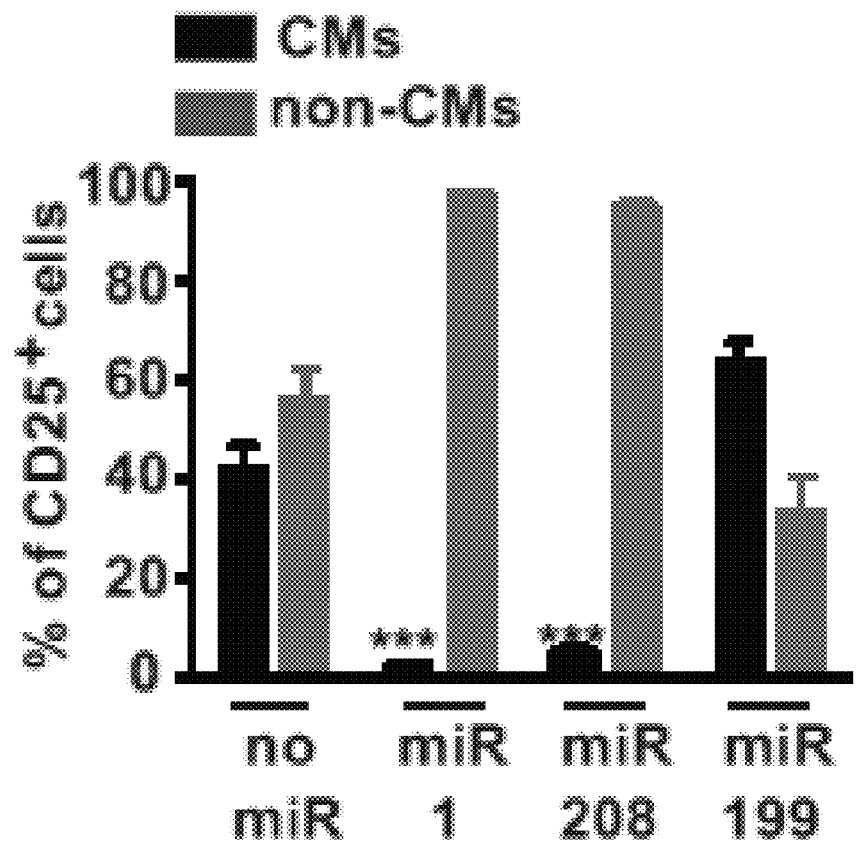
Figure 7D:
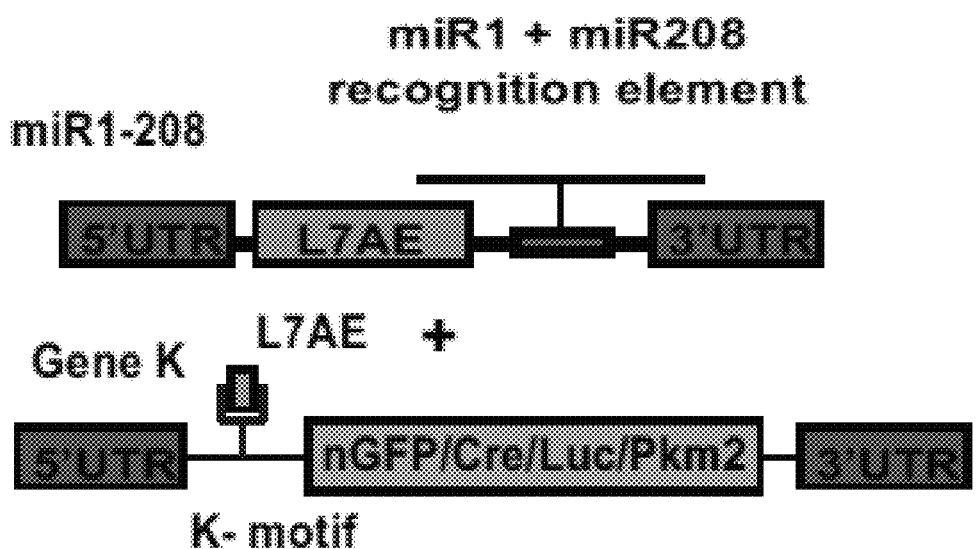
Figure 7E:
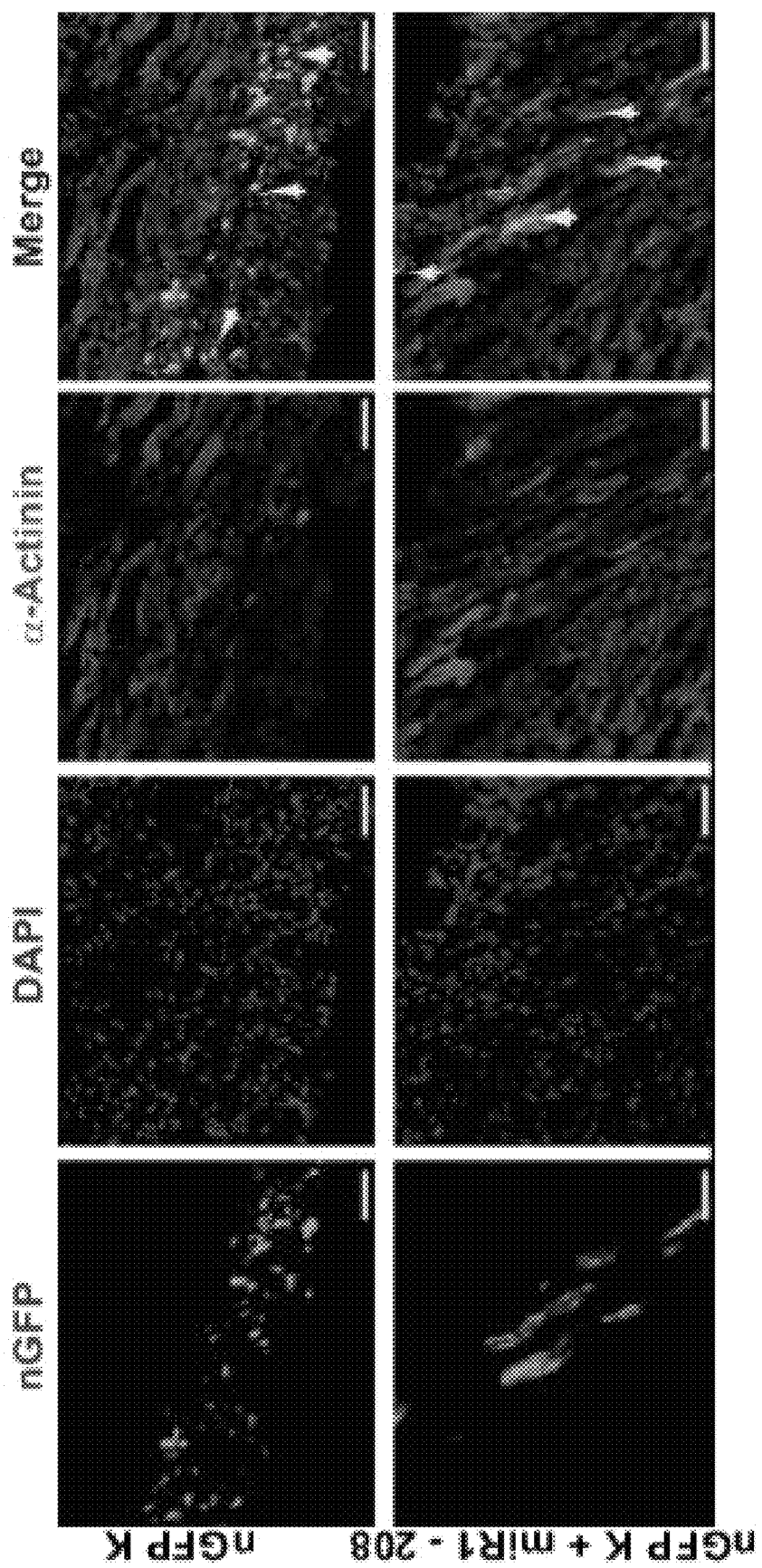
Figure 7F:
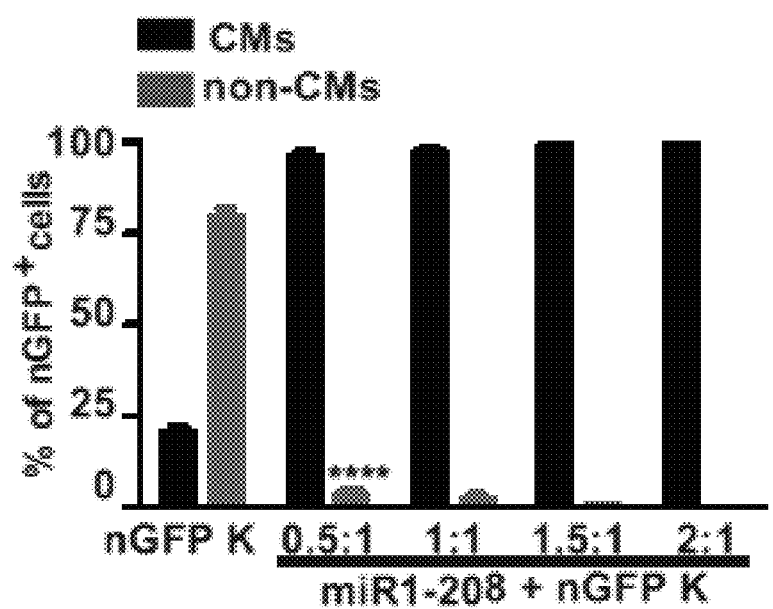
Figure 7G:
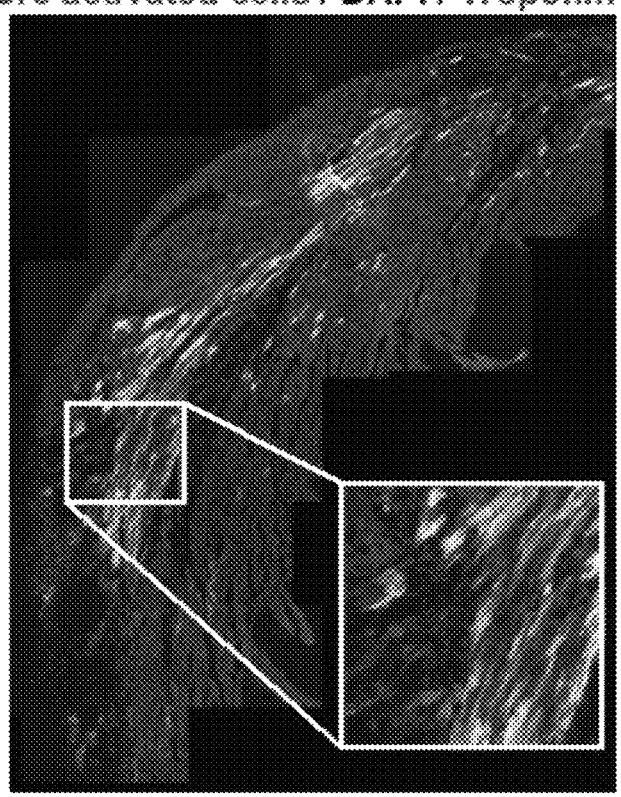
Figure 7H:
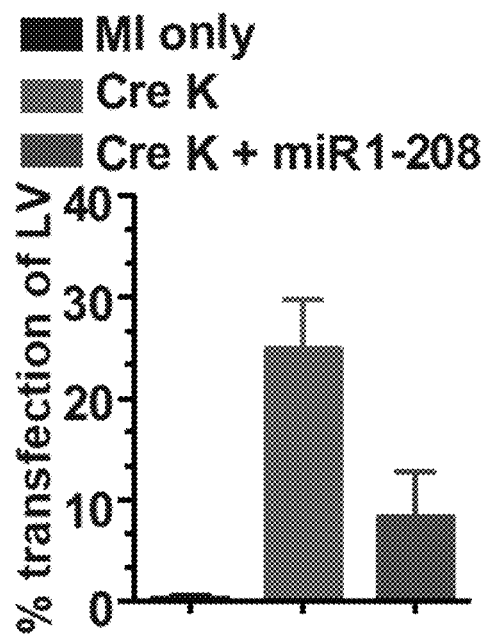
Figure 7I:
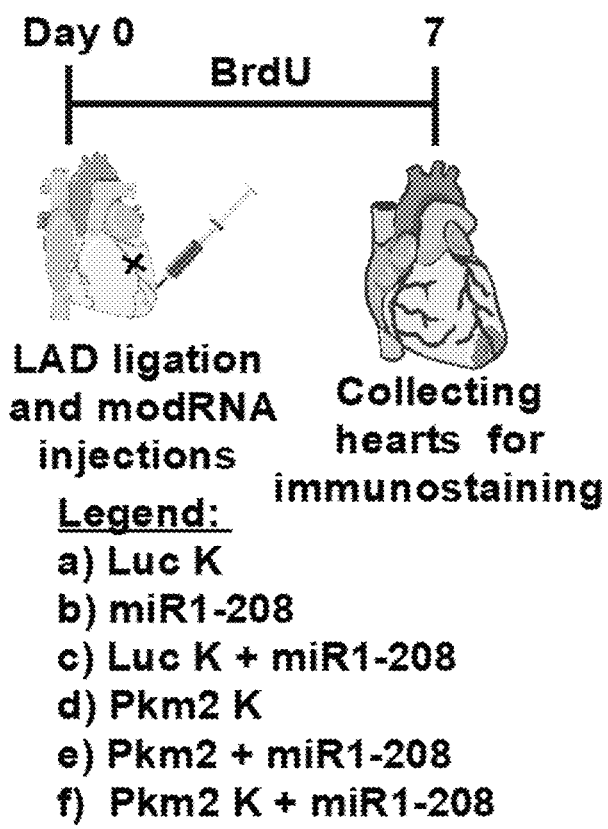
Figure 7J:
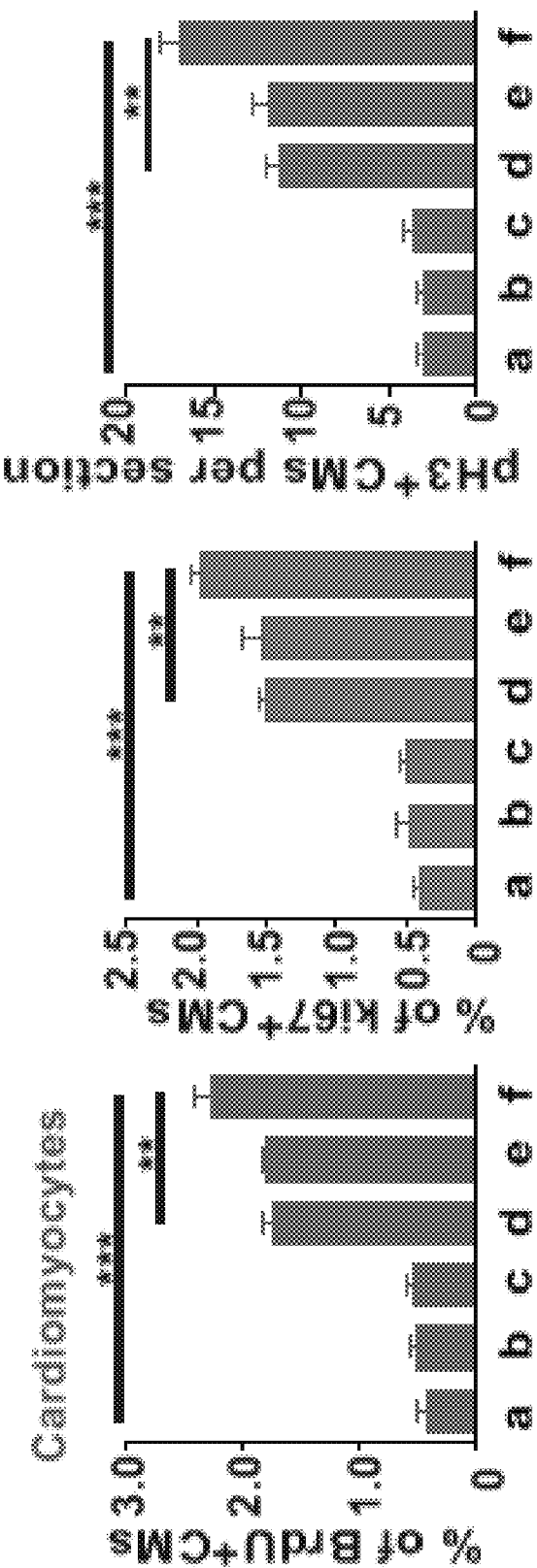
Figure 7K:
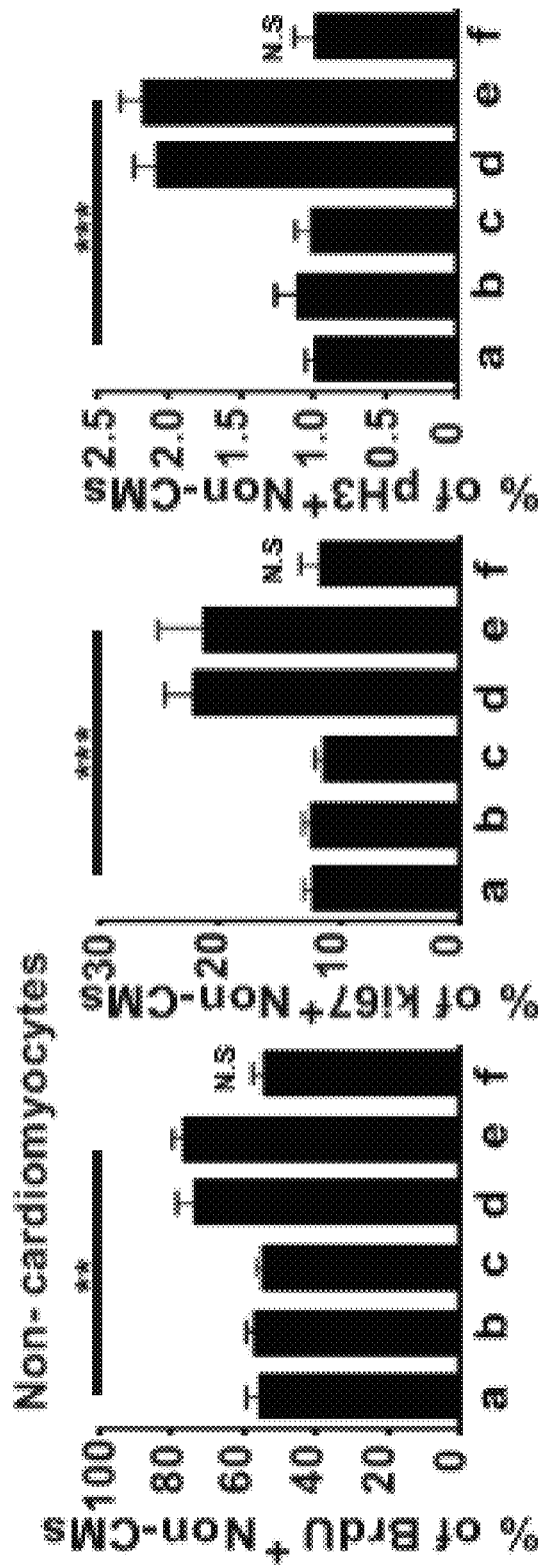
Figure 8A:
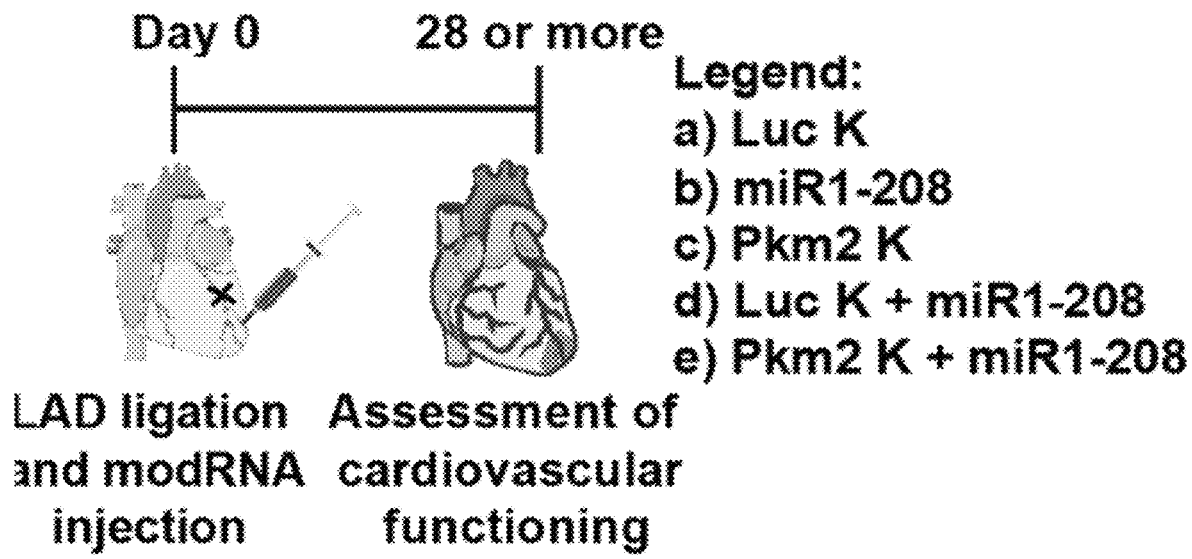
FIGS. 8A-8N show that $_{cms}$Pkm2 modRNA improves cardiac function and outcome post MI. A Experimental timeline to evaluate cardiac function and outcome. B MRI assessments of left ventricular systolic function 1 month post-MI. Images depict left ventricular chamber (outlined in red) in diastole and systole. C Percentage of ejection fraction for the experiments in b. D Echo evaluation of delta in percentage of fractioning shorting differences between day 2 (baseline) and day 28 post-MI. E Representative pictures of masson trichrome staining to evaluate scar size 28 days post-MI. F-I Quantification of scar size F, heart weight to body weight ratio G, CMs size H, and capillary density I measured 28 days post-MI. J-M Number of CMs with different treatments 28 days post-MI. J Representative image of the number of CMs in each group. K Quantification of the experiment in j. L Representative images of nuclei of isolated CMs (mono, bi or multi). M Quantification of the experiment in I N Long-term post-MI survival curve for mice injected with Pkm2-K or luc-K modRNAs and co-transfected with miR1-208. Results represent 2 independent experiments (n=5 mice); *, P<0.001, , P<0.01, *, P<0.05, One-way ANOVA, Bonferroni post hoc test. P-values for long term survival were calculated using the Mantel-Cox log-rank test. Scale bar 10 µm.
Figure 8B:
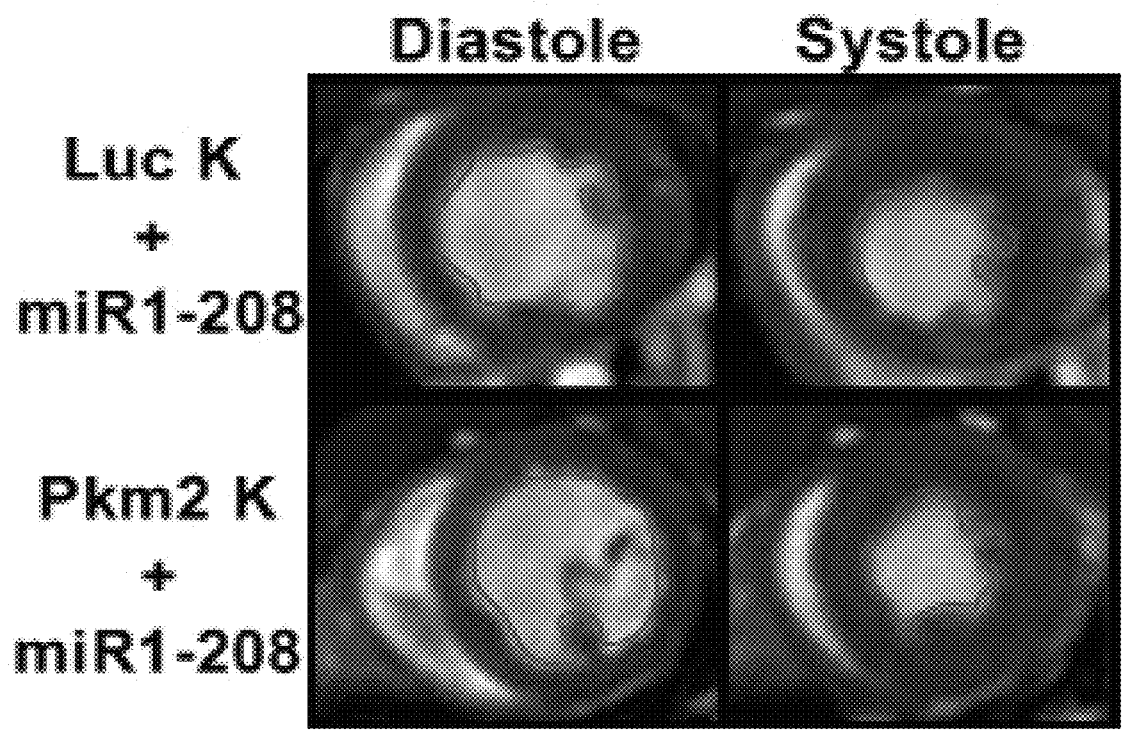
Figure 8C:
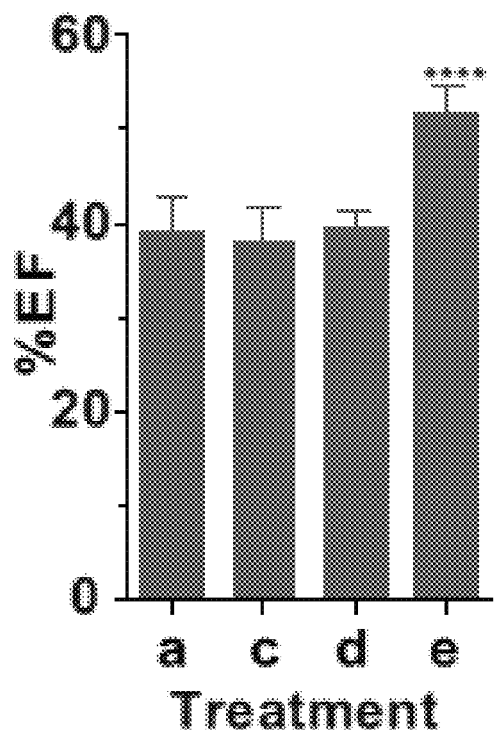
Figure 8D:
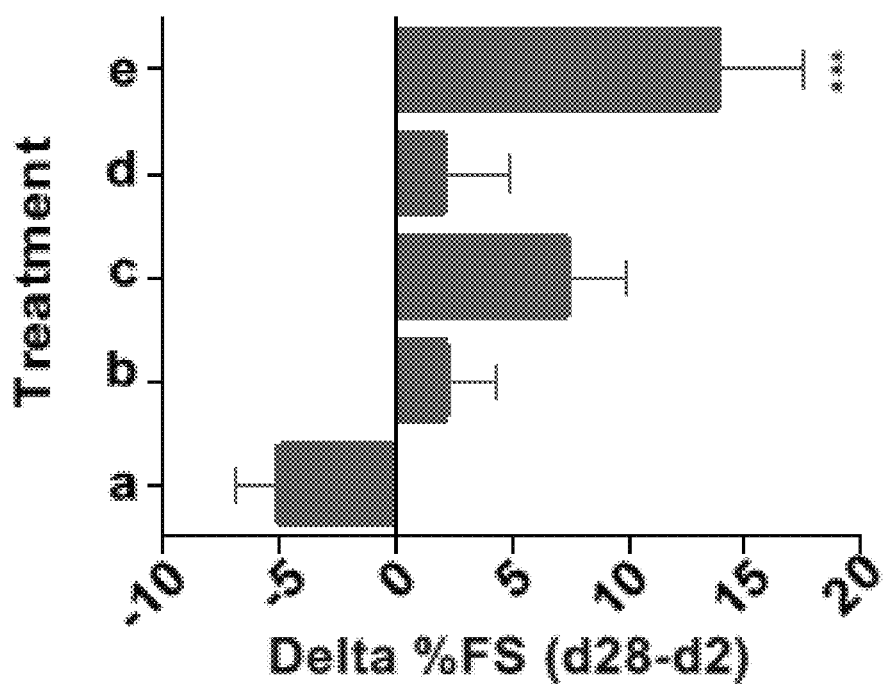
Figure 8E:
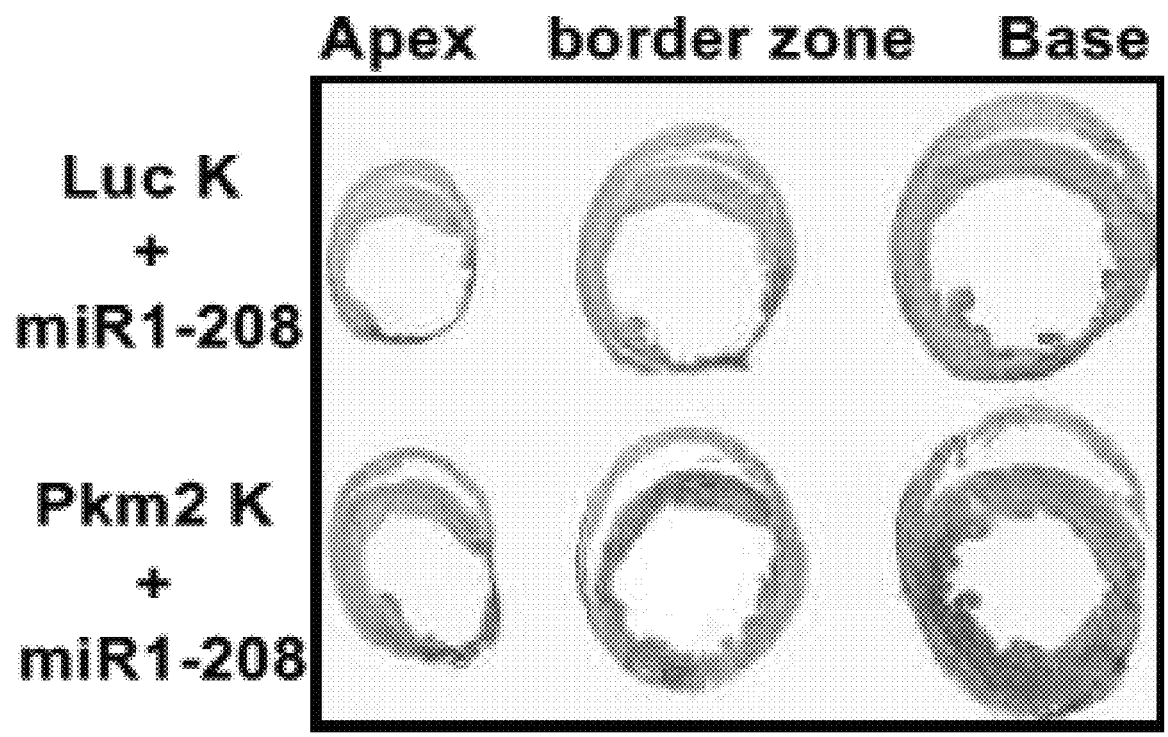
Figure 8F:
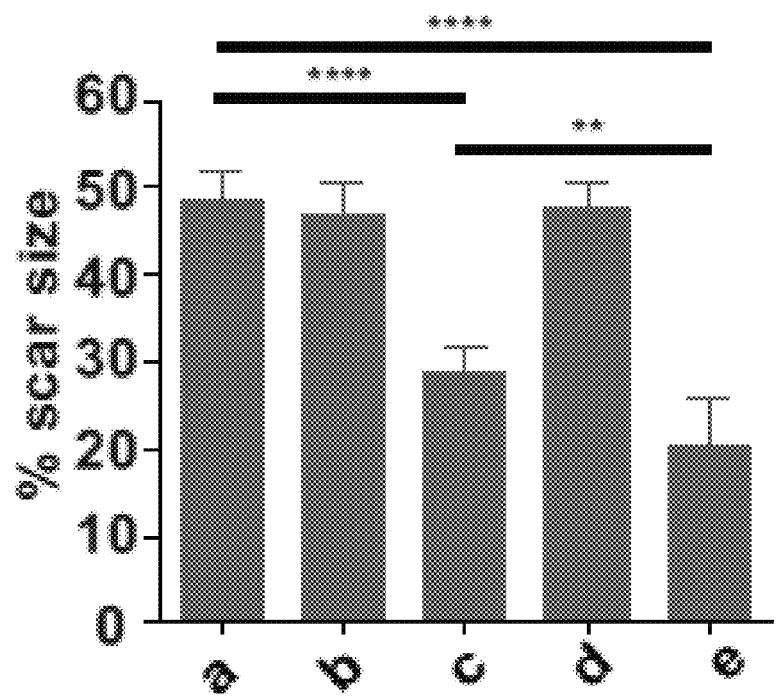
Figure 8G:
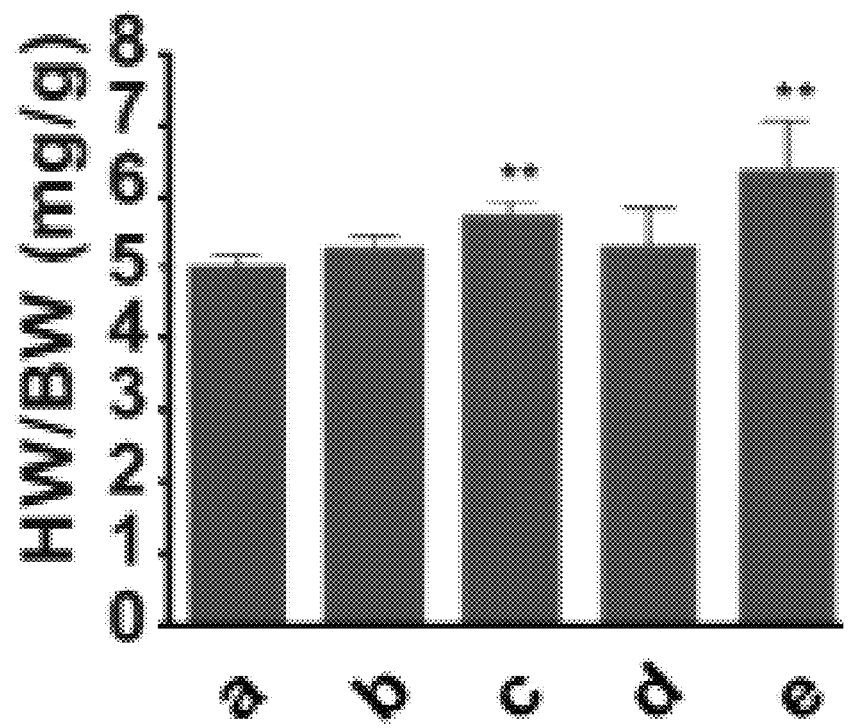
Figure 8H:
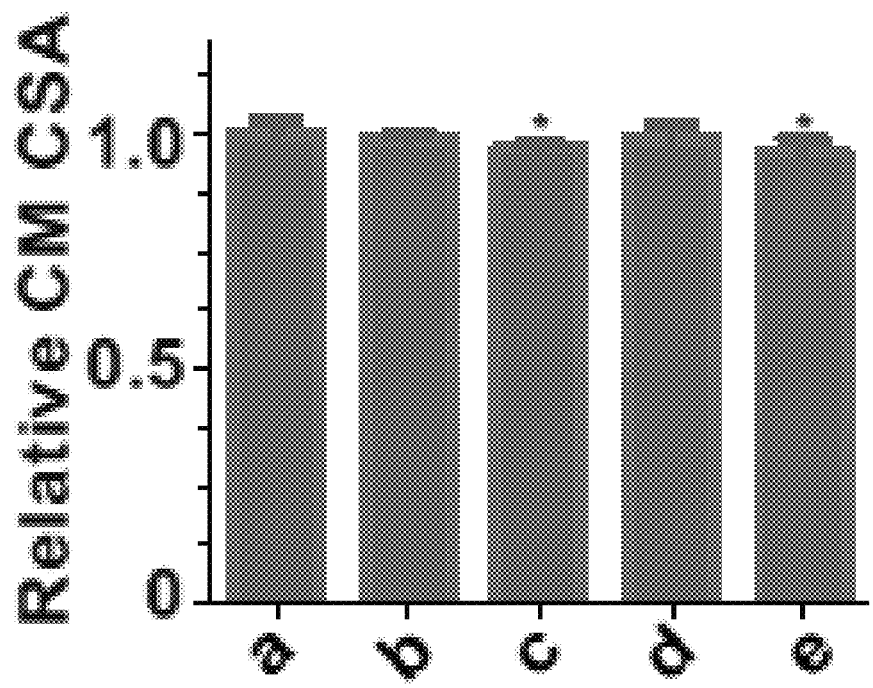
Figure 8I:
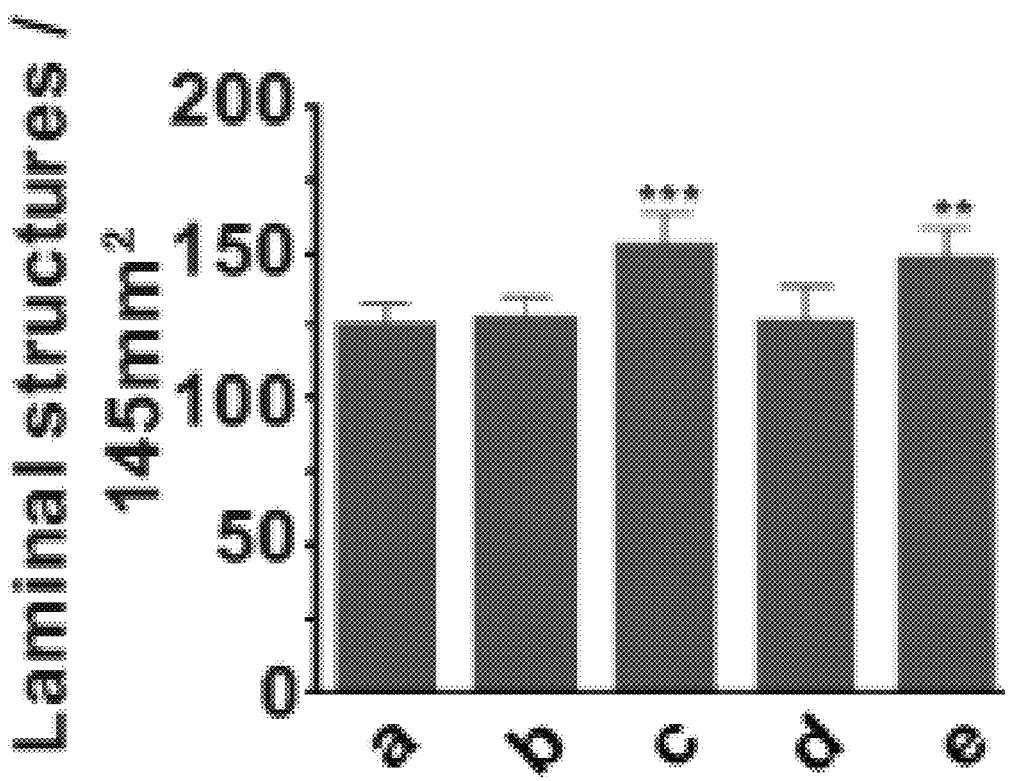
Figure 8J:
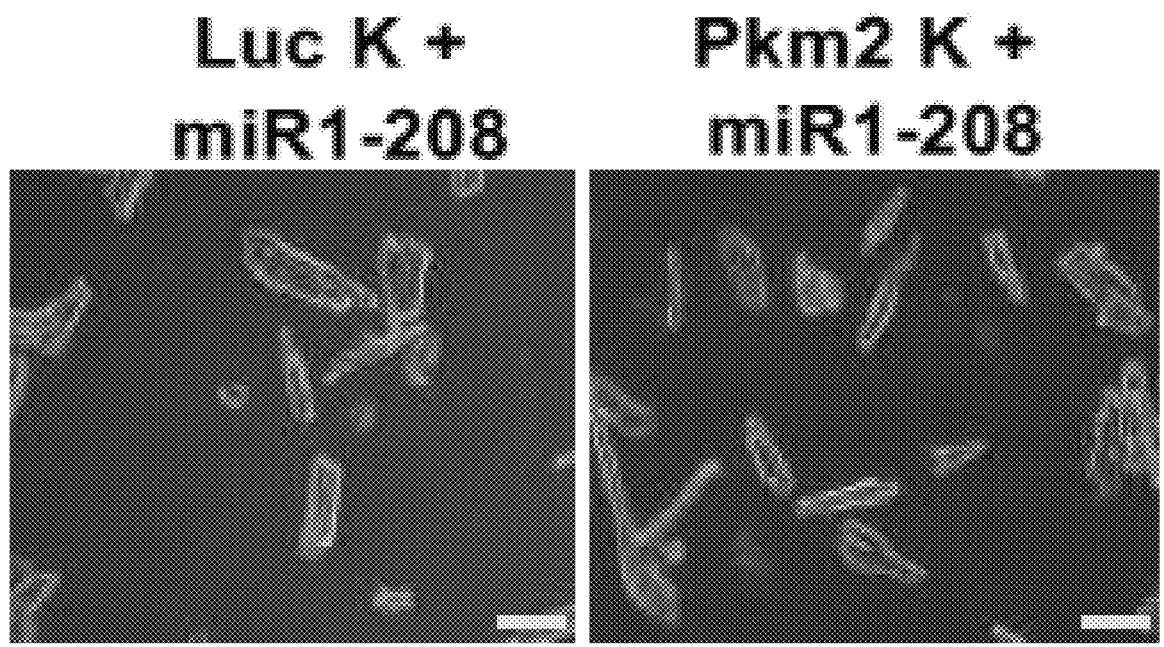
Figure 8K:
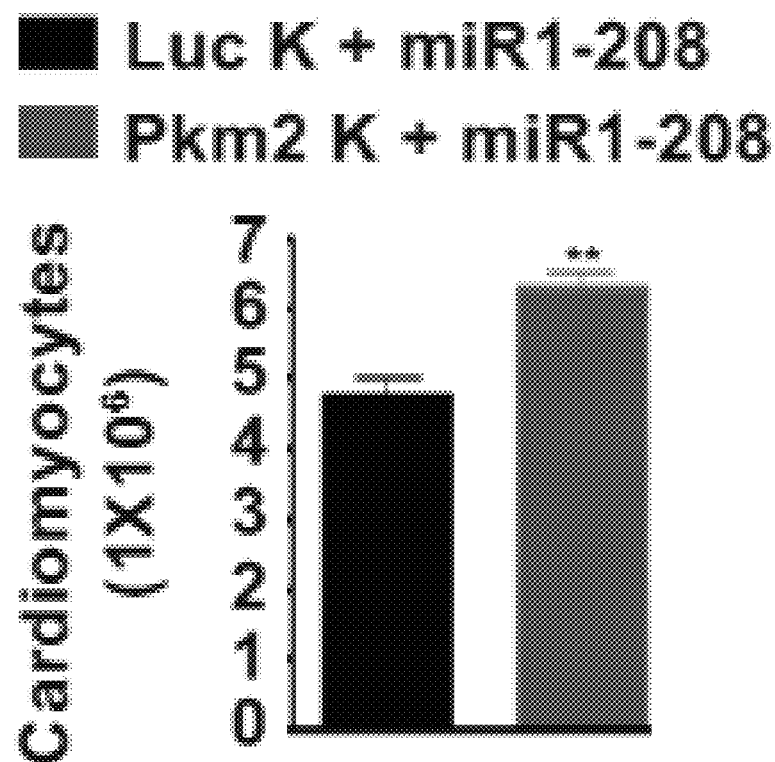
Figure 8L:
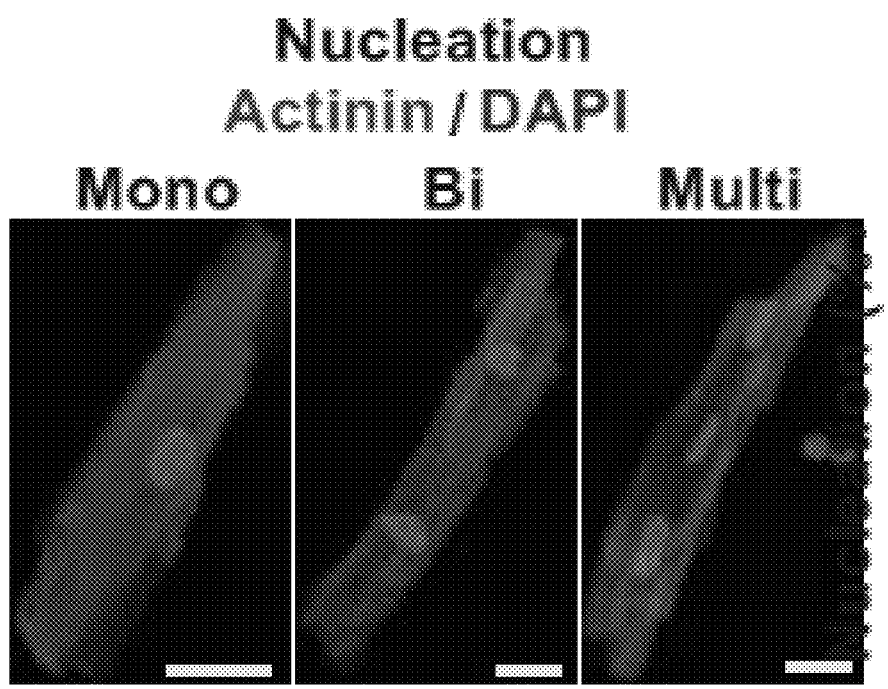
Figure 8M:
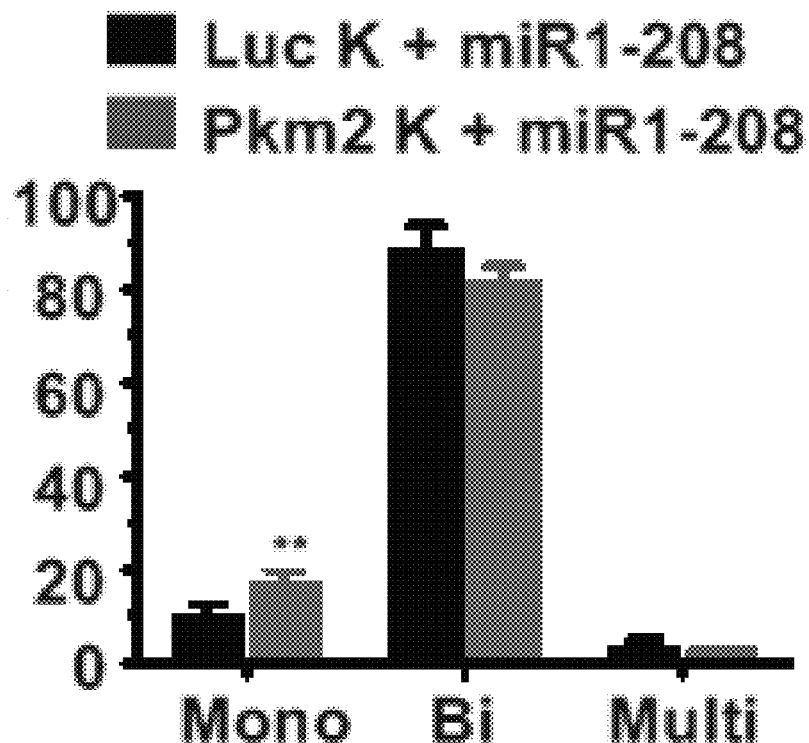
Figure 8N:
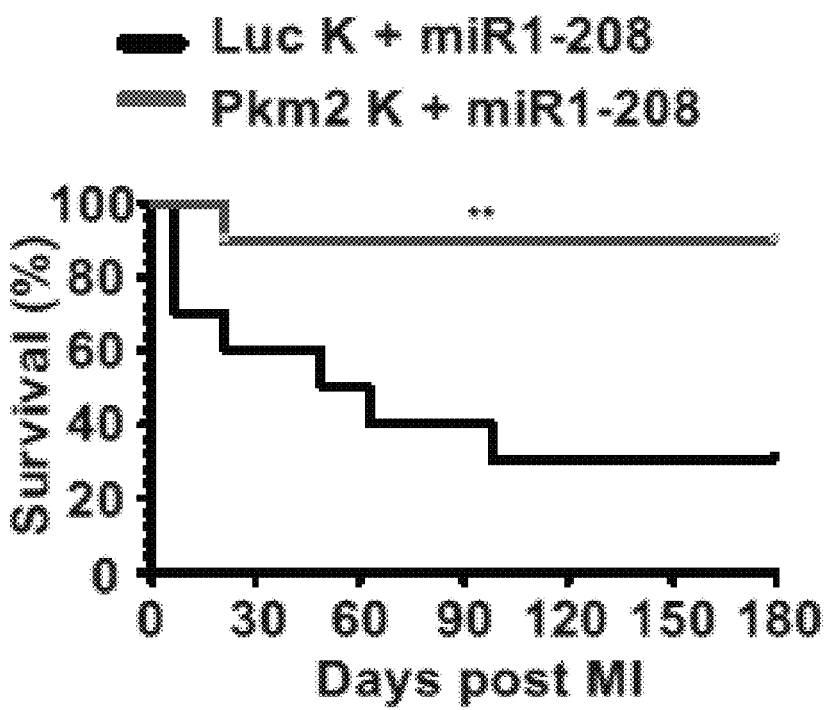
Figure 9A:
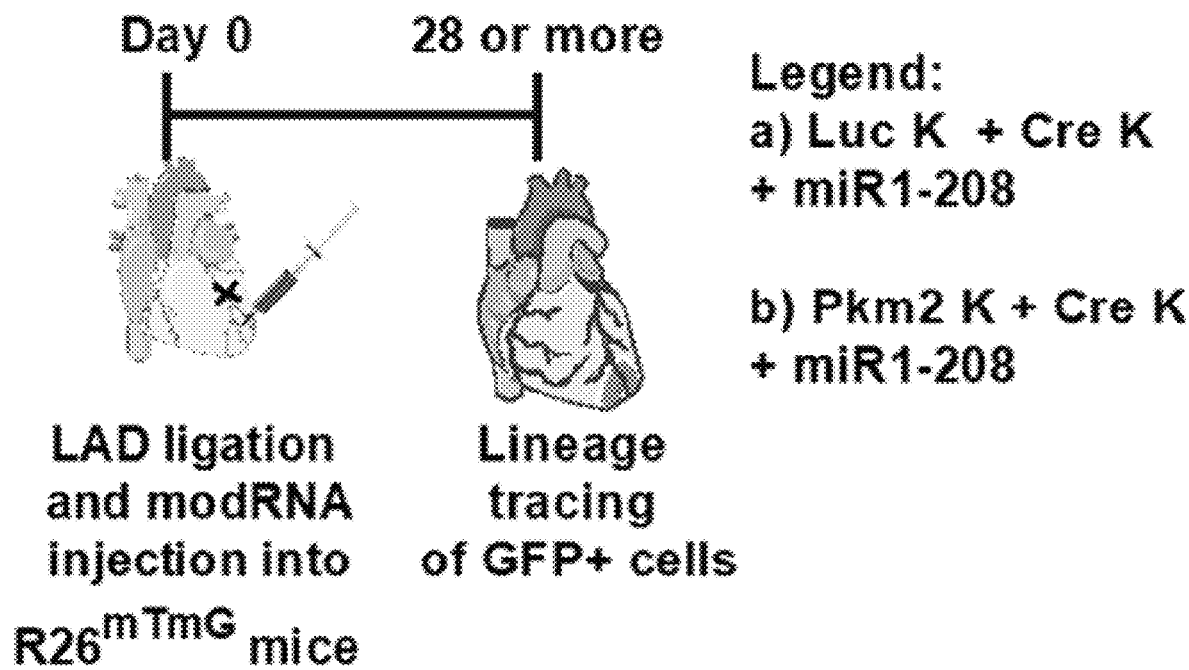
FIGS. 9A-9M show a lineage tracing of CMs expressing cms Pkm2 post-MI and shows increased number of transfected CMs and induction of key downstream mediators of Pkm2's functions. A Experimental timeline used for cardiac lineage tracing in R26$^{mTmG}$ mice B Transfection efficiency (% GFP$^+$) of CMs or non-CMs 28 days post-MI. C Representative images of CMs and their progeny (GFP$^+$) 28 days post-MI. D Quantification of GFP$^+$ CMs 3 or 28 days post-MI. Ratio of heart to body weight E, relative size of GFP$^+$ CMs F, and number of nuclei in GFP$^+$ CMs G in hearts, 28 days post-MI. H Representative image of GFP$^+$ CMs, pH3$^+$ or Ki67$^+$ 28 days post-MI. Quantification of GFP$^+$ pH3$^+$ CMs I or GFP$^+$ Ki67$^+$ CMs J 28 days post transfection with $_{cms}$Luc or $_{cms}$Pkm2 with $_{cms}$Cre modRNA in MI model. K-M 2 days post-MI and administration of $_{cms}$ihCD25 with $_{cms}$Luc or $_{cms}$Pkm2 modRNAs, adult CMs were isolated using magnetic beads. K qRT-PCR analysis to validate purity of isolated CMs. L Gene expression comparisons of key genes for both PPP (G6PD) and key downstream indirect transcriptional targets of Pkm2 in adult CMs. M Expression of cell-cycle promoting genes or cell-cycle inhibitors. Results represent 2 independent experiments (n=3 mice); *, P<0.001, , P<0.01, *, P<0.05, N.S, Not Significant, two-tailed student t-test (b-j) or ANOVA with Bonferroni post hoc test (k-m). Scale bar 50 or 10 µm in c or h, respectively.
Figure 9B:
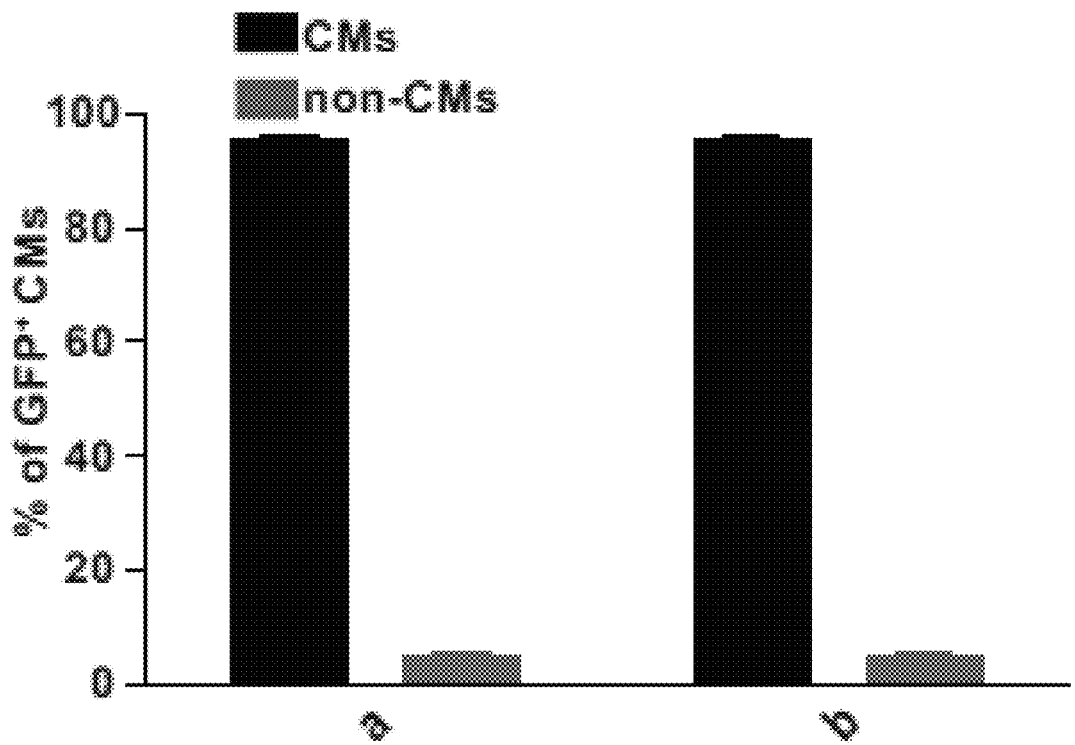
Figure 9C:
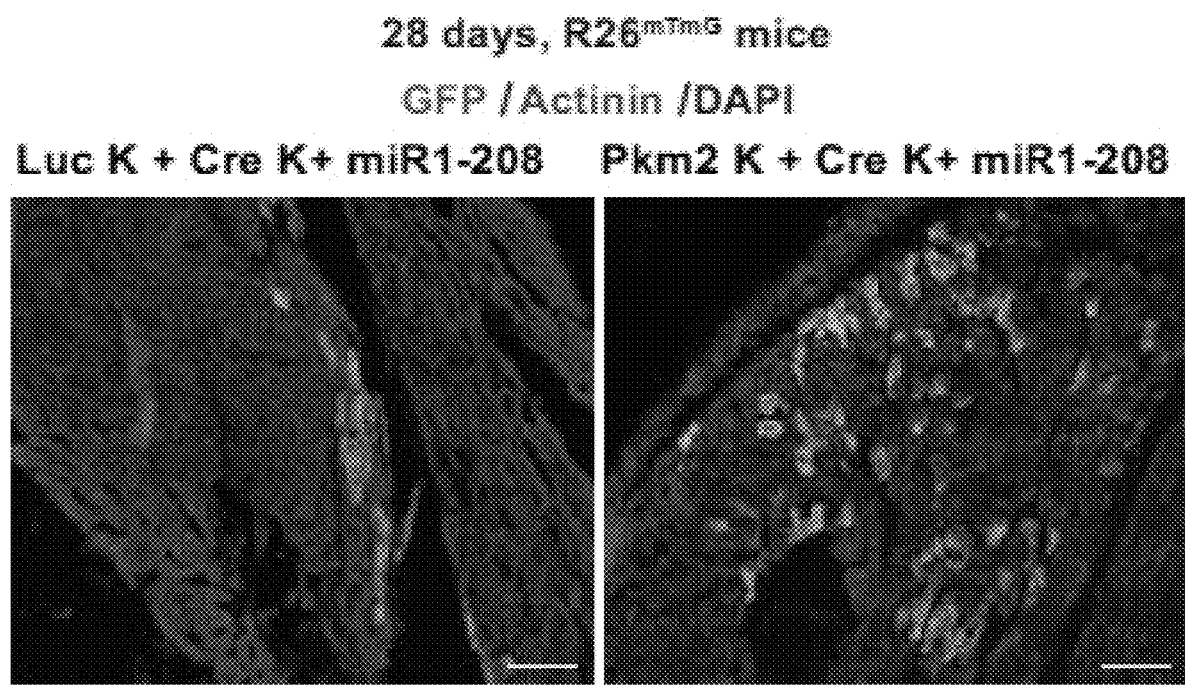
Figure 9D:
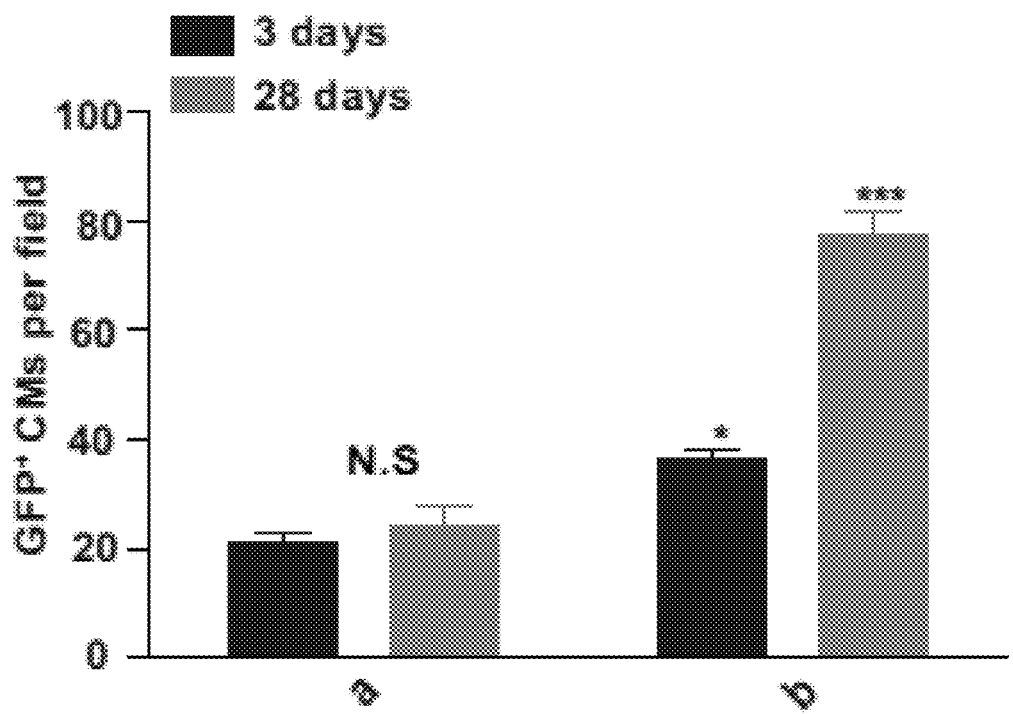
Figure 9E:
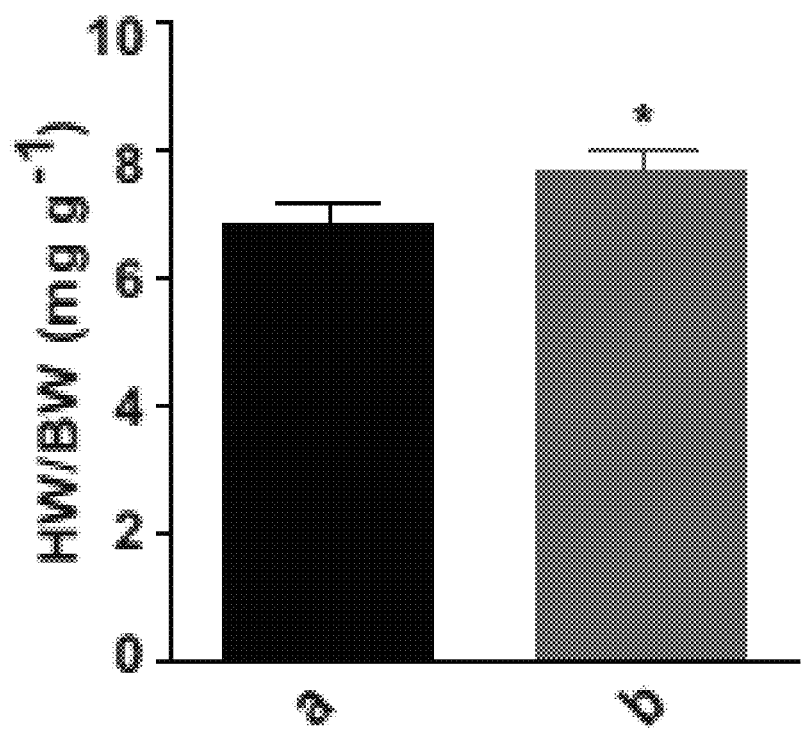
Figure 9F:
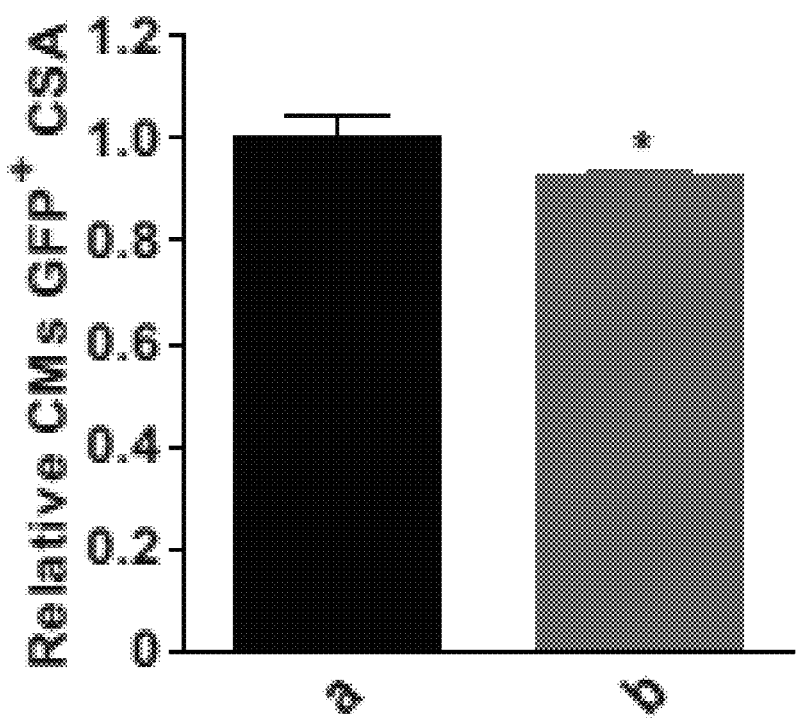
Figure 9G:
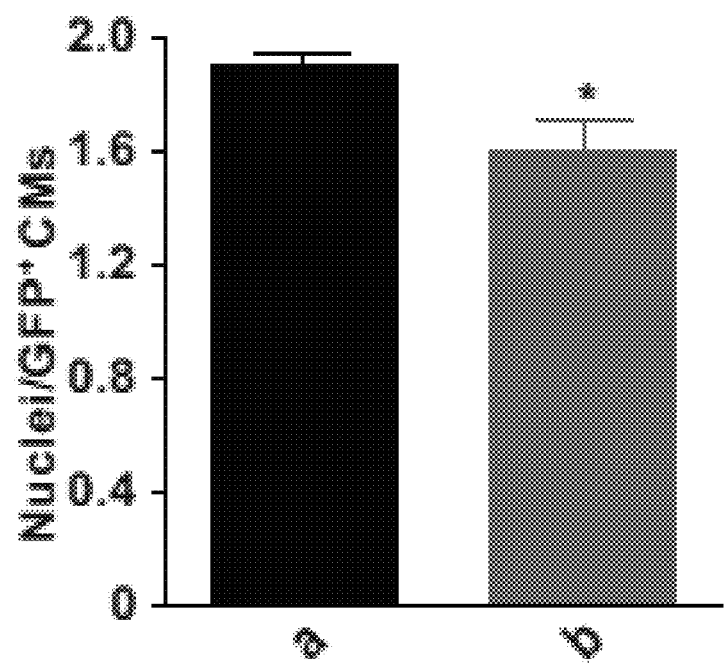
Figure 9H:
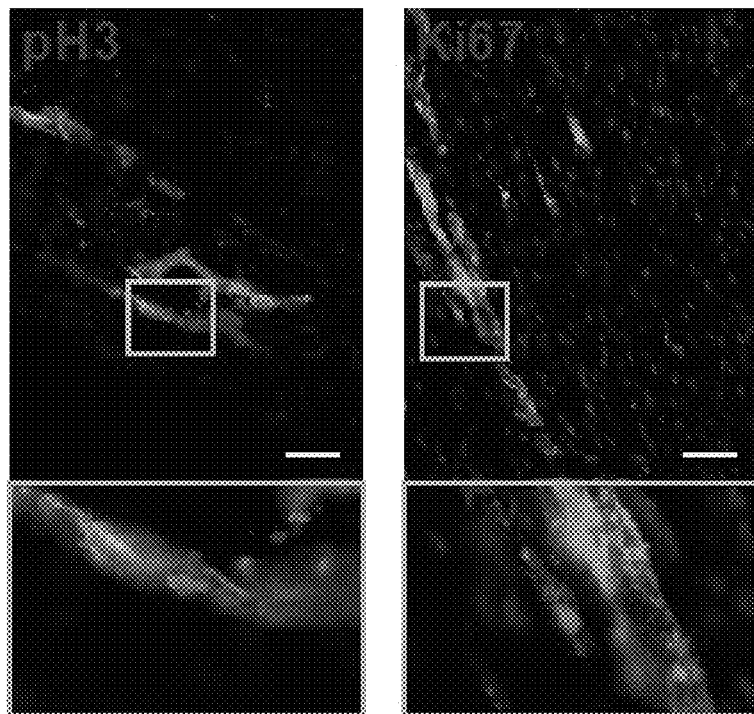
Figure 9I:
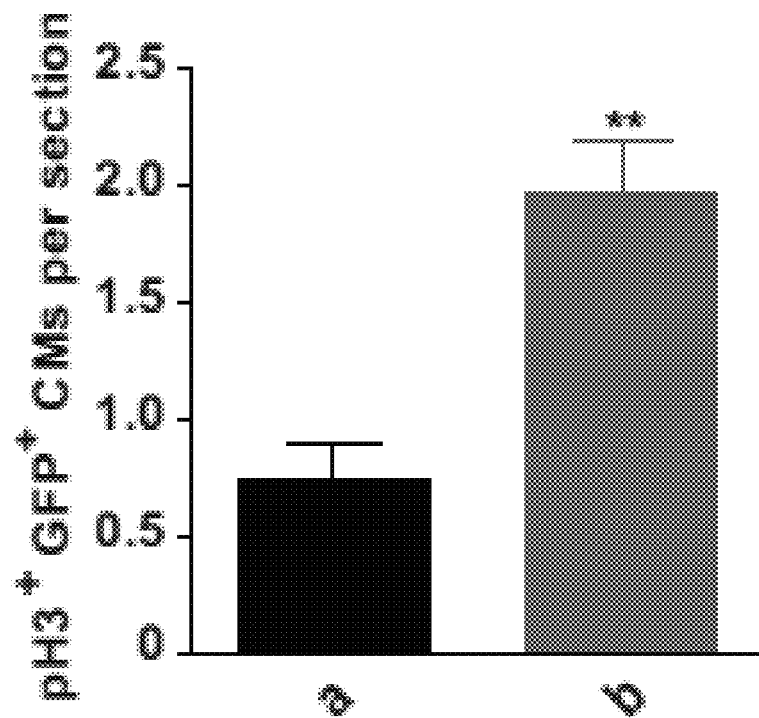
Figure 9J:
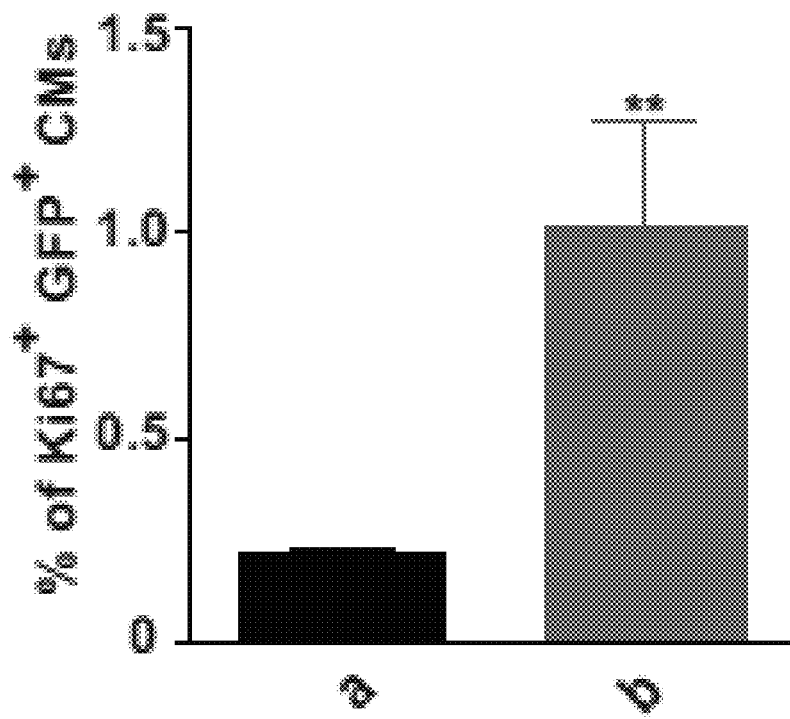
Figure 9K:
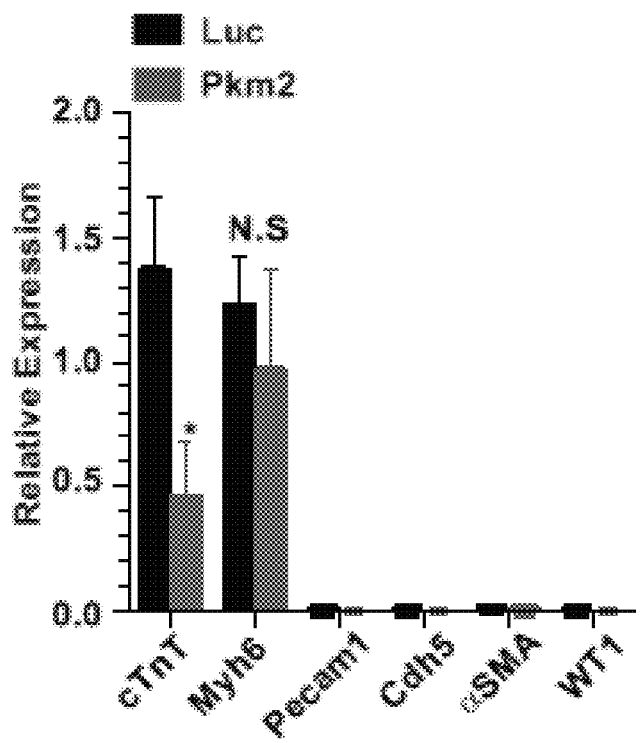
Figure 9L:
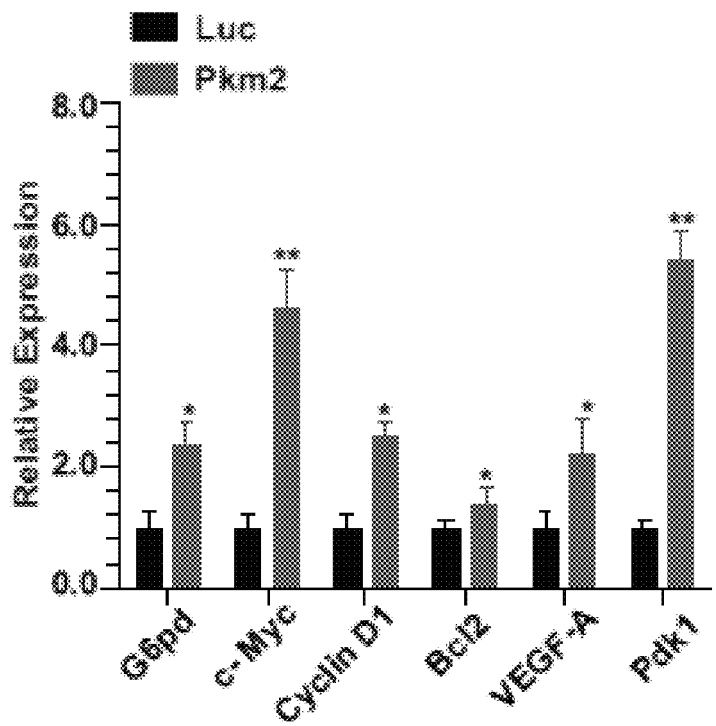
Figure 9M:
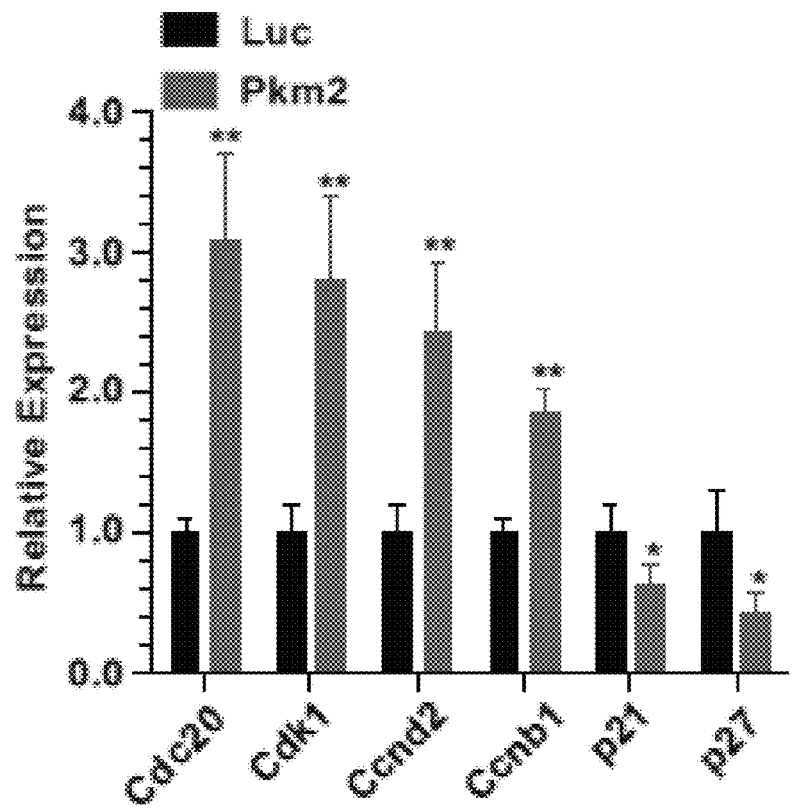
Figure 10A:
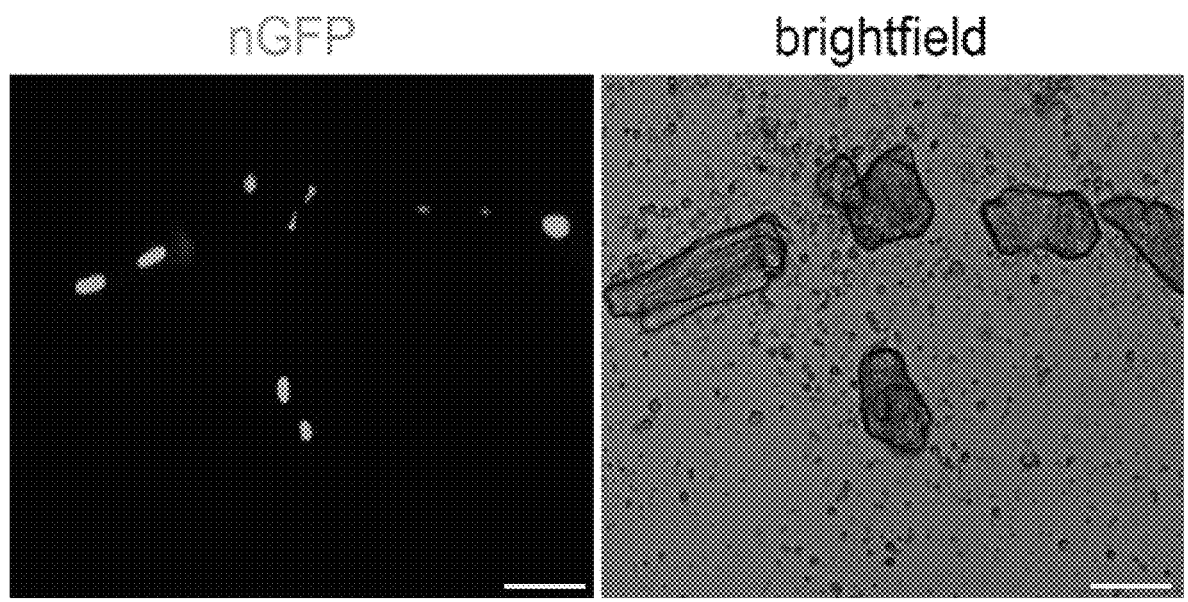
FIGS. 10A-10B shows that adult CMs are successfully transfected with modRNA in vitro. Isolated adult CMs were transfected with nuclear GFP (nGFP) and imaged 20 hours post transfection (bar=10 µm.)
Figure 10B:
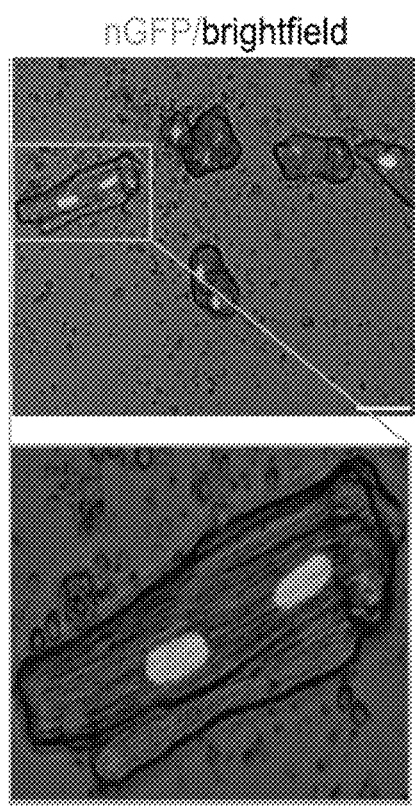
Figure 11:
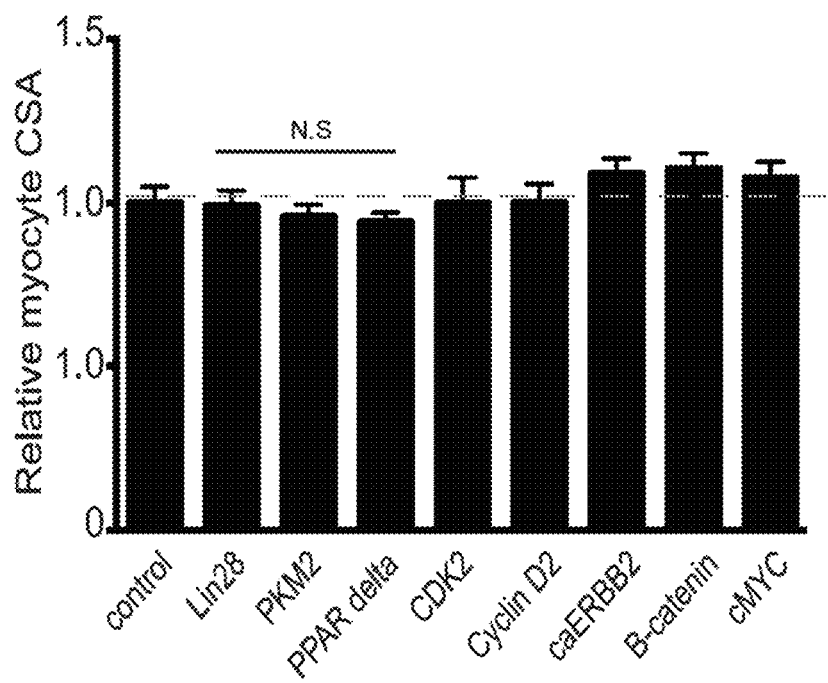
FIG. 11 is a bar graph showing that activation of proliferation of adult CMs in vivo using cell cycle inducer modRNAs do not compromise CM integrity. CM size was measured using wheat germ agglutinin (WGA) staining for CMs cross-section area evaluation in hearts 7 days after MI with different modRNA treatments. Results indicate no significant differences in CM integrity and size when cell cycle inducer Lin28 or Pkm2 modRNAs were delivered in adult mouse MI model. Results represent two independent experiments with n=3 mice, N.S, not significant, two-tailed student t-test.
Figure 12A:
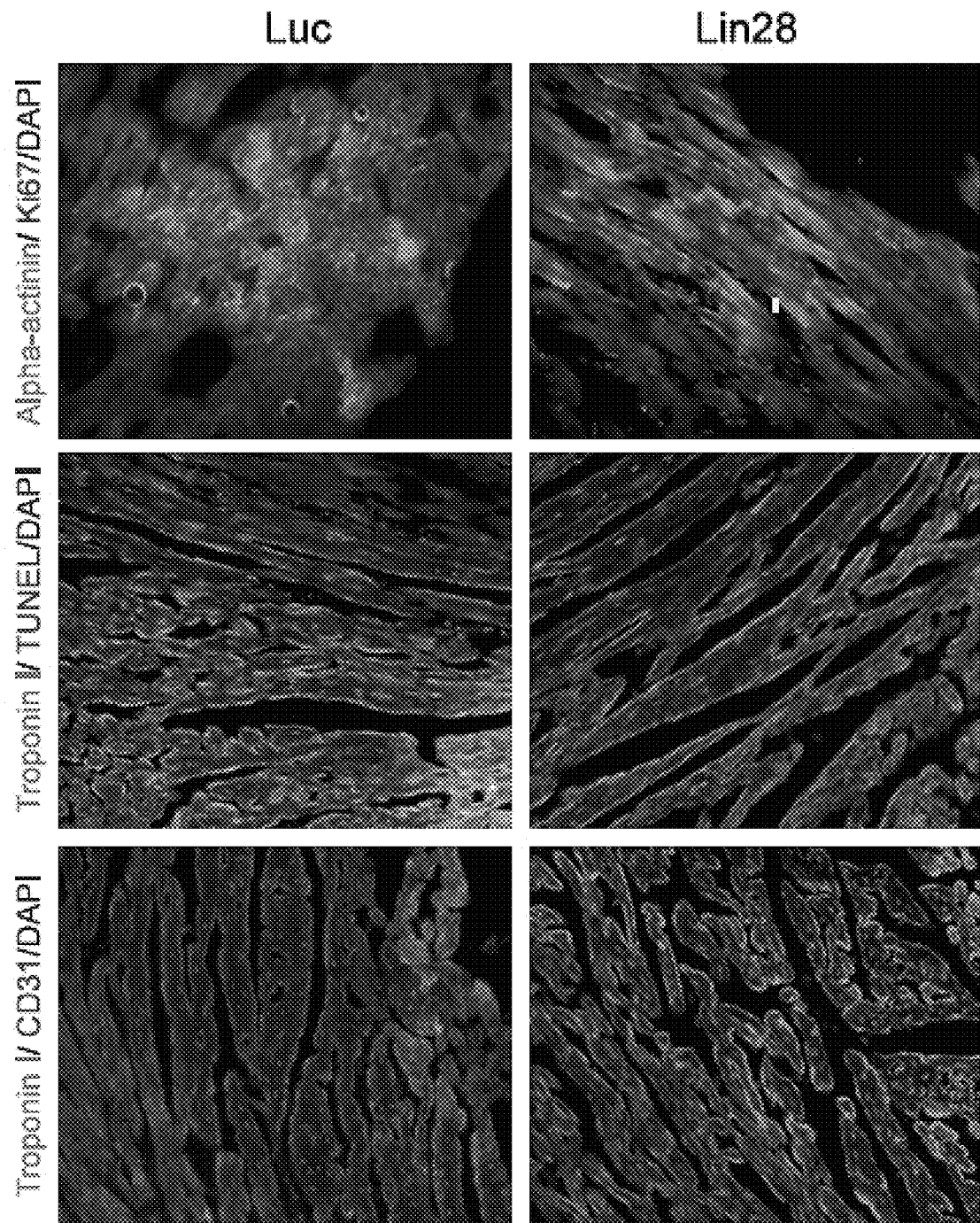
FIGS. 12A-12C show that activation of proliferation of adult CMs in vivo using cell cycle inducer modRNAs reduces CM apoptosis and increases capillary density. CM proliferation (Ki67+) apoptosis (TUNEL+) and capillary density (Cd31+ luminal structures) were measured in the left ventricle of hearts 7 days post MI and different modRNA treatments. A representative data showing Lin28, cell cycle inducer modRNA treatment 7 days post MI induce CM proliferation, reduce apoptosis and increase capillary density. Quantifiable results for apoptosis B or capillary density C level with the different treatments. Results indicate significant reduction in CM apoptosis and elevation in capillary density using cell cycle inducer genes such as Lin28 (red), and PKM2. Results represent two independent experiments with n=3 mice, ***, P<0.001, two-tailed student t-test.
Figure 12B:
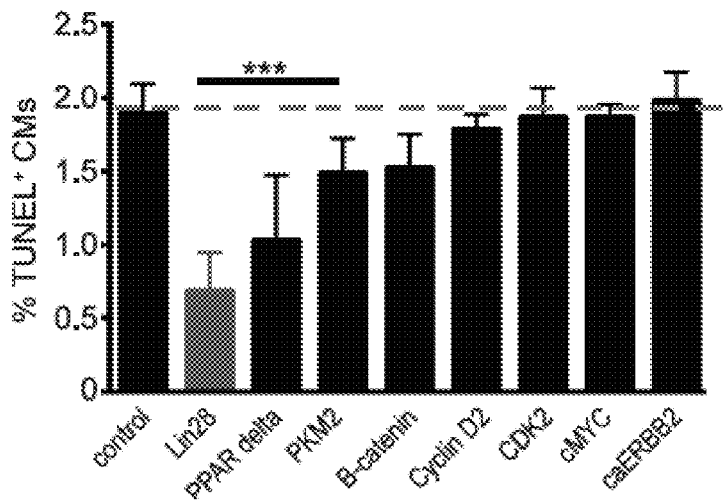
Figure 12C:
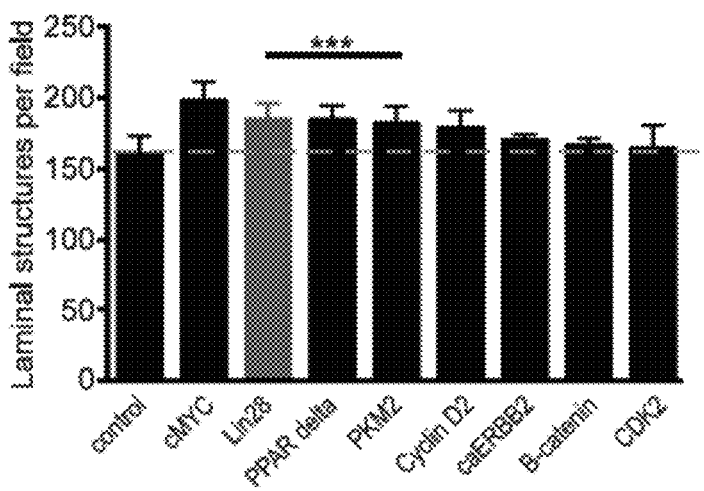
Figure 13A:
FIGS. 13A-13C show that miR-1 and miR-208 are expressed exclusively in rat neonatal CMs in vitro. A Inactivate human CD25 (ihCD25) modRNA with or without miR recognition element for miR-208, miR1, miR133a, miR126, miR199, miR378 and miR29a were transfected into neonatal CM in vitro. 20 hours post transfection cells were fixed and stained with anti CD25 (red) and Troponin I (CM marker, green). B Images taken for different treatments showing that when ihCD25 modRNA had recognition elements of miR-1 or miR-208, CMs (Troponin I+ cells) were unable to translate ihCD25 modRNA (Troponin I+ and ihCD25+ CMs), other treatments resulted in ihCD25 translated in CMs. This indicate that only miR-1 or miR-208 are CMs specific. C quantification of the experiments. Results represent two independent experiments with n=3 wells, bar=10 mm.
Figure 13B:
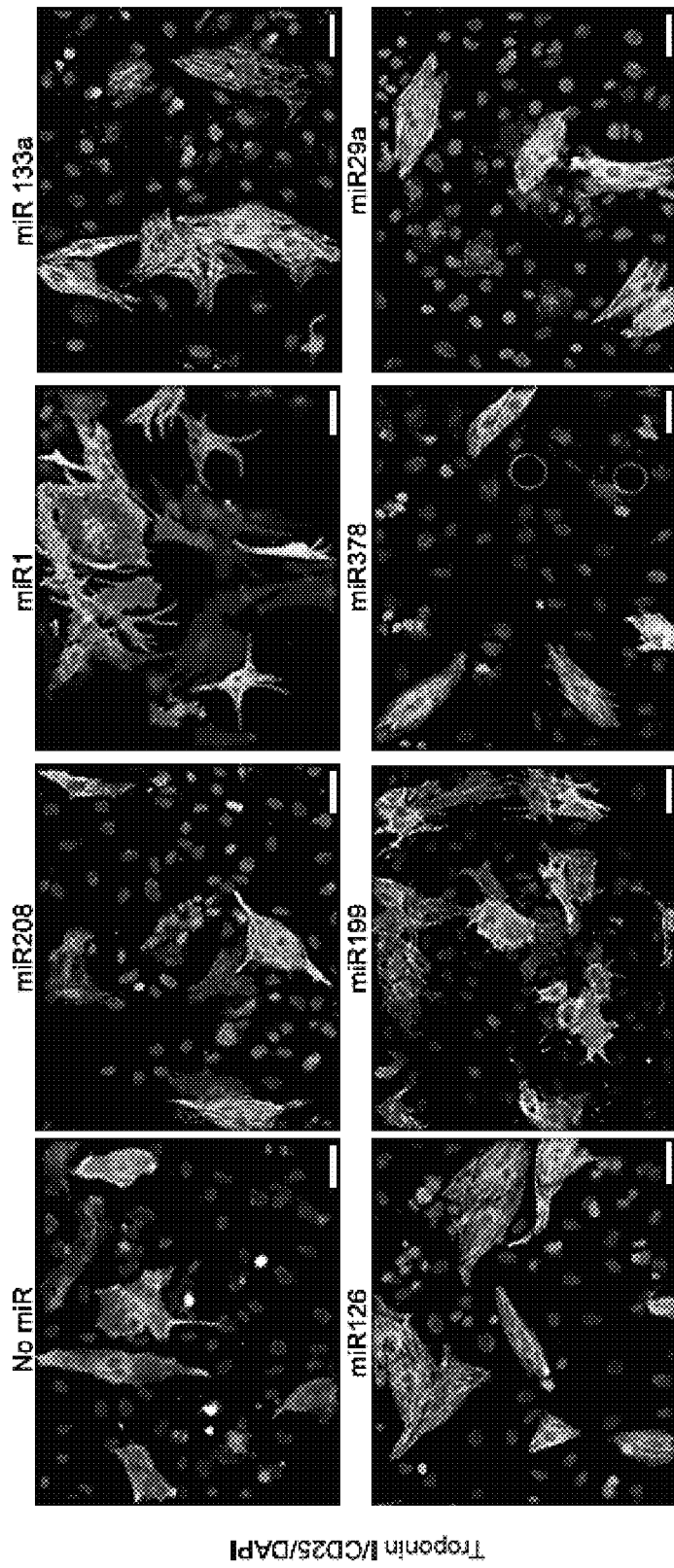
Figure 13C:
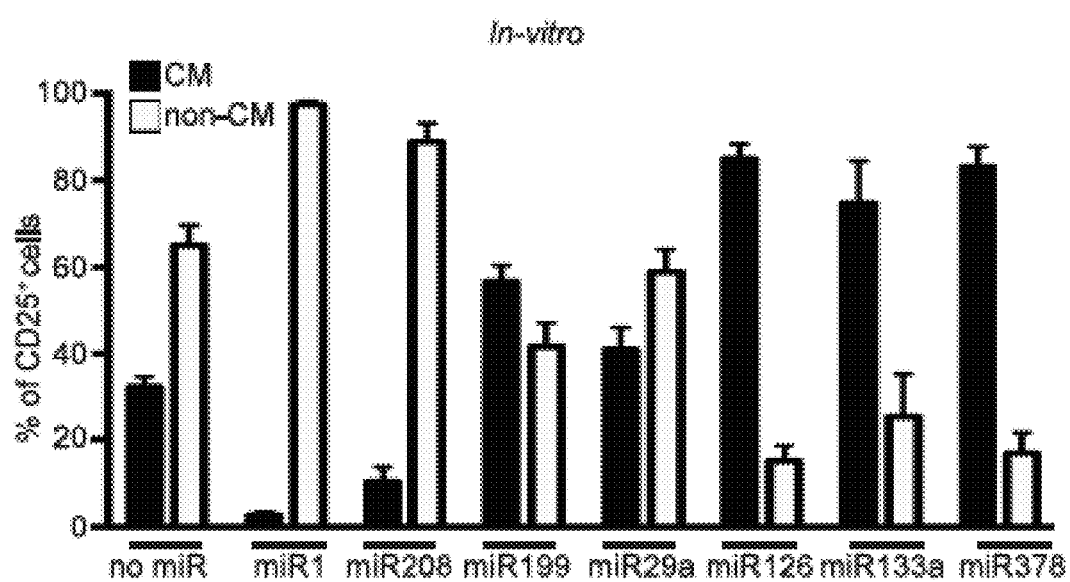
Figure 14A:
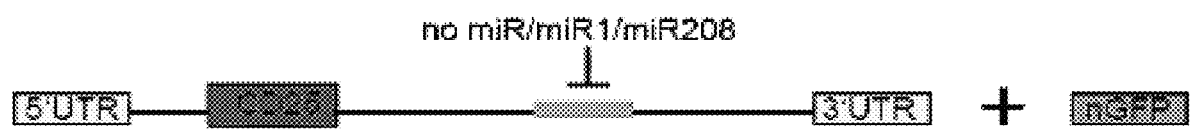
FIGS. 14A-14C show that miR-1 and miR-208 are expressed exclusively in rat neonatal CMs in vitro. A ihCD25 modRNA with or without miR recognition element for miR-208 or miR1 were co-transfected with nGFP into neonatal CM in vitro. 20 hours post transfection cells were fixed and stained with anti CD25 (red) and Troponin I (CMs marker, green nuclear). nGFP was used as transfection control. B images taken for different treatments showing that when ihCD25 modRNA had recognition elements of miR-1 or miR-208, CMs (Troponoin I+ cells) were unable to translate ihCD25 modRNA (Troponoin I+ and ihCD25+ cells), however ihCD25 modRNA without miR recognition elements was able to translate in CMs. all cells were transfected with nGFP indicating that modRNA was delivered successfully. C quantification of the experiments. Results represent two independent experiments with n=3 wells, bar=10 mm.
Figure 14B:
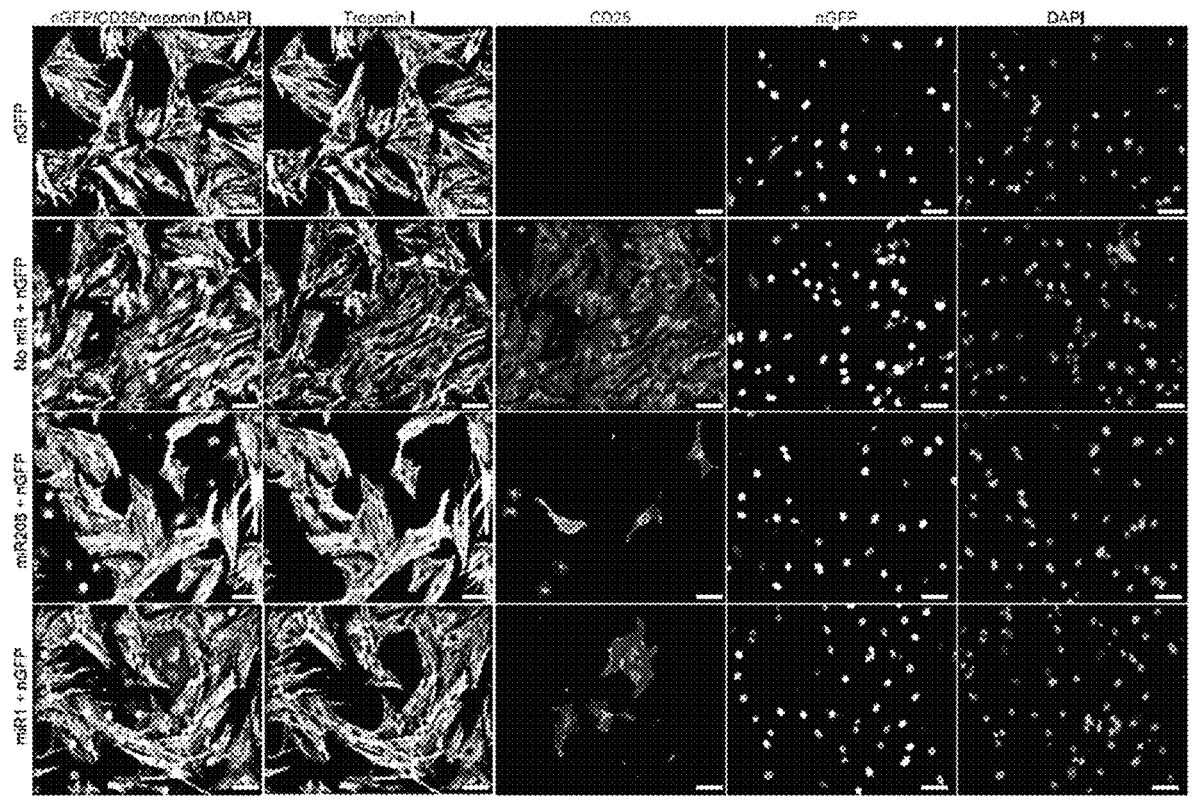
Figure 14C:
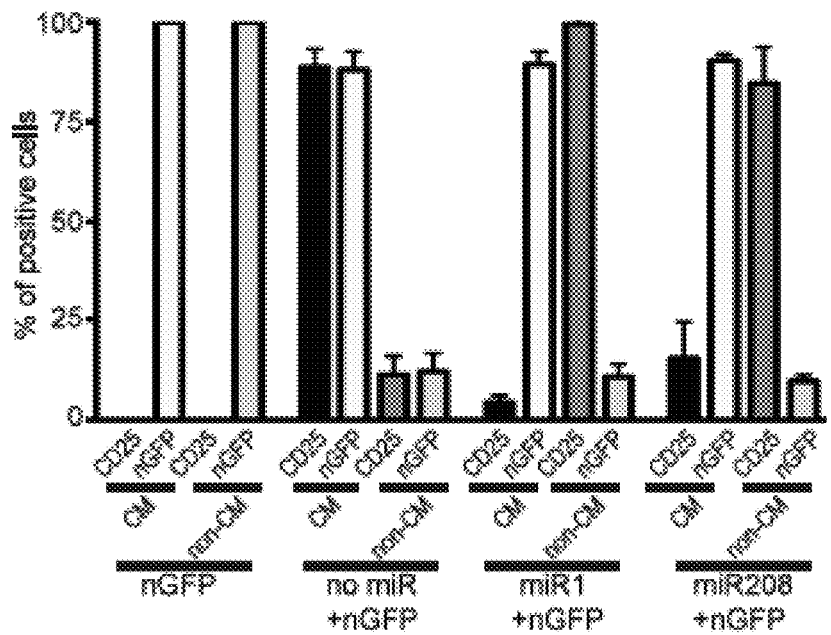
Figure 15A:
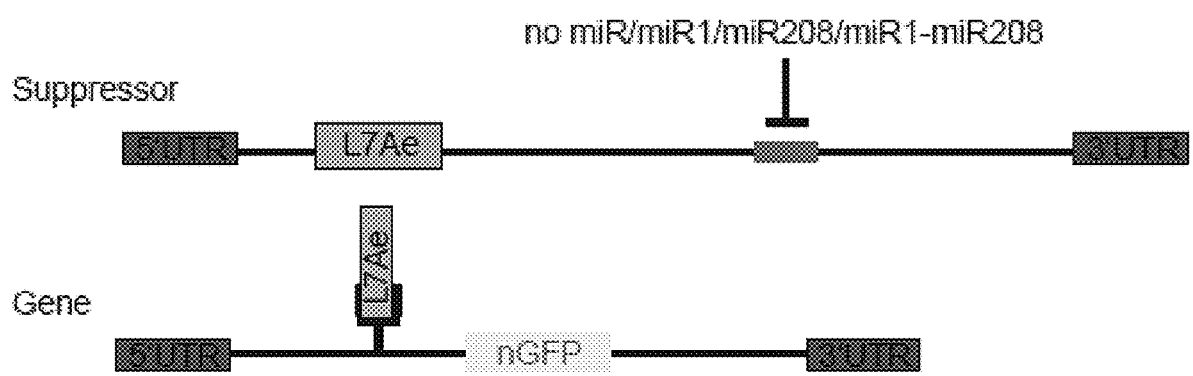
FIGS. 15A-15C show that miR-1 and miR-208 express exclusively in adult mouse heart in vivo. A ihCD25 modRNA with or without miR recognition element for miR-208 or miR1 were co-transfected with nGFP into adult mouse heart in MI model. 20 hours post MI and delivery of modRNA hearts were collected, fixed and stained with anti CD25 (red), Troponoin I (CMs marker, white) and nGFP (green). nGFP was used as transfection control. B images taken for different treatments showing that when ihCD25 modRNA had recognition elements of miR-1 or miR-208, CMs (Troponoin 1+ cells) were unable to translate ihCD25 modRNA (Troponoin 1+ and ihCD25+ cells), transfecting ihCD25 without miR recognition site resulted in ihCD25 translated in CMs. all cells were transfected with nGFP indicating that modRNA was delivered successfully. C quantification of the experiments. Results represent two independent experiments with total n=5 mice, bar=10 mm.
Figure 15B:
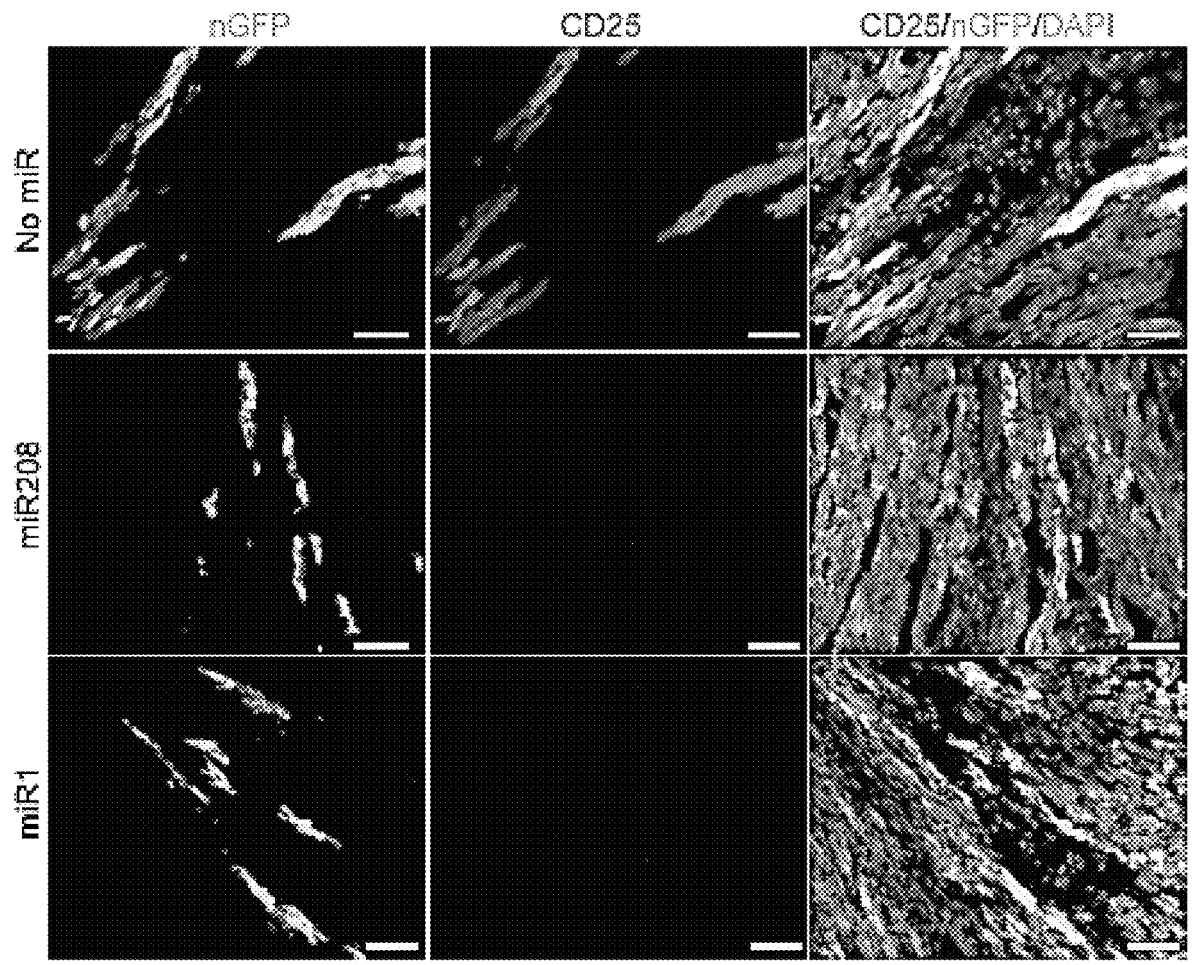
Figure 15C:
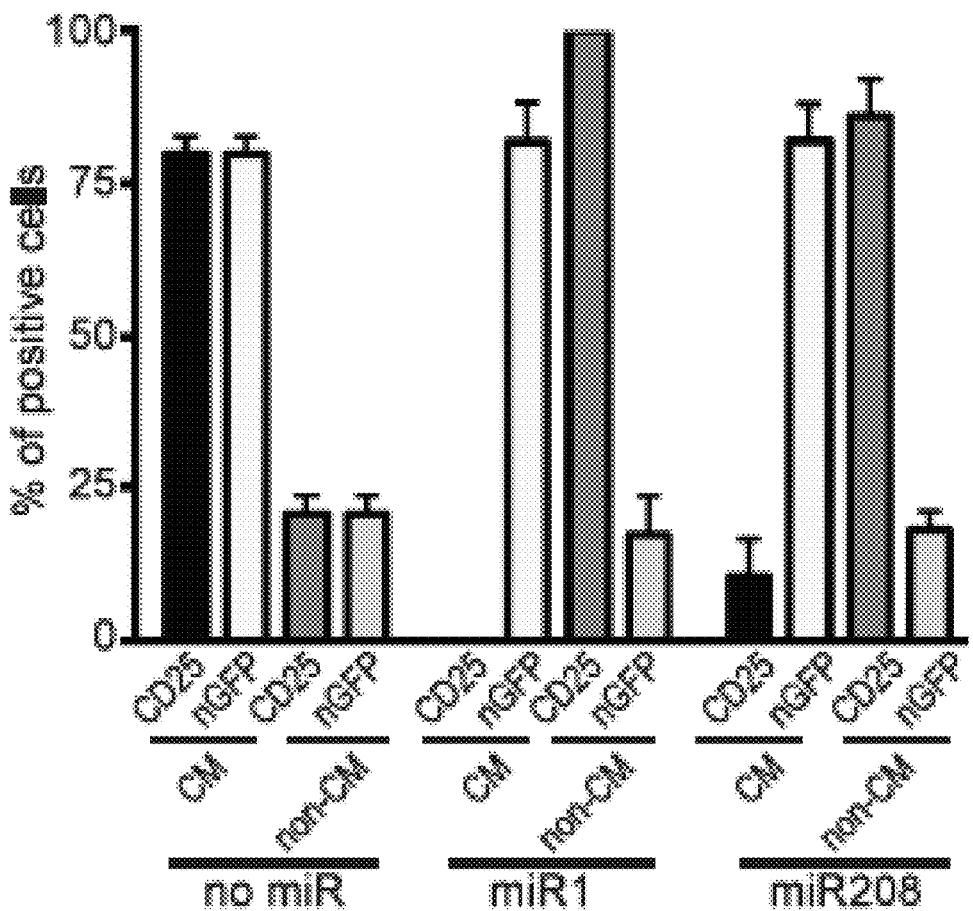
Figure 16A:
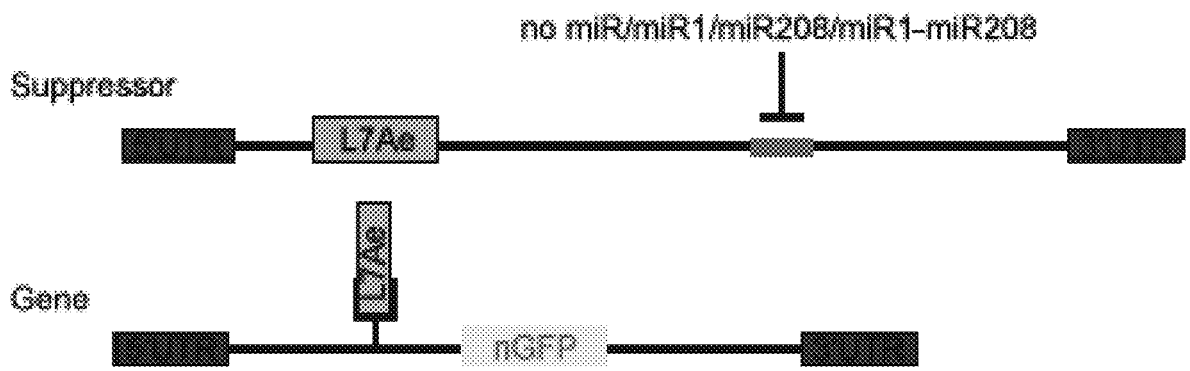
FIGS. 16A-16C show that nGFP CMs specific modRNA carrying recognition element for miR-208, miR-1, or both, in 1:1 ratio, show nGFP translation mostly in CMs in vitro. A CMs specific modRNA design. B nGFP CMs specific modRNA caring recognition element for miR-208, miR-1, or both, in 1:1 ratio, were transfected into neonatal rat CMs in vitro. 20 hours post transfection cells were fixed and stain for nGFP (nuclear green) and Troponin I (CM marker, red). C quantification of the experiment described in B. Results represent two independent experiments with n=3 wells, bar=10 mm.
Figure 16B:
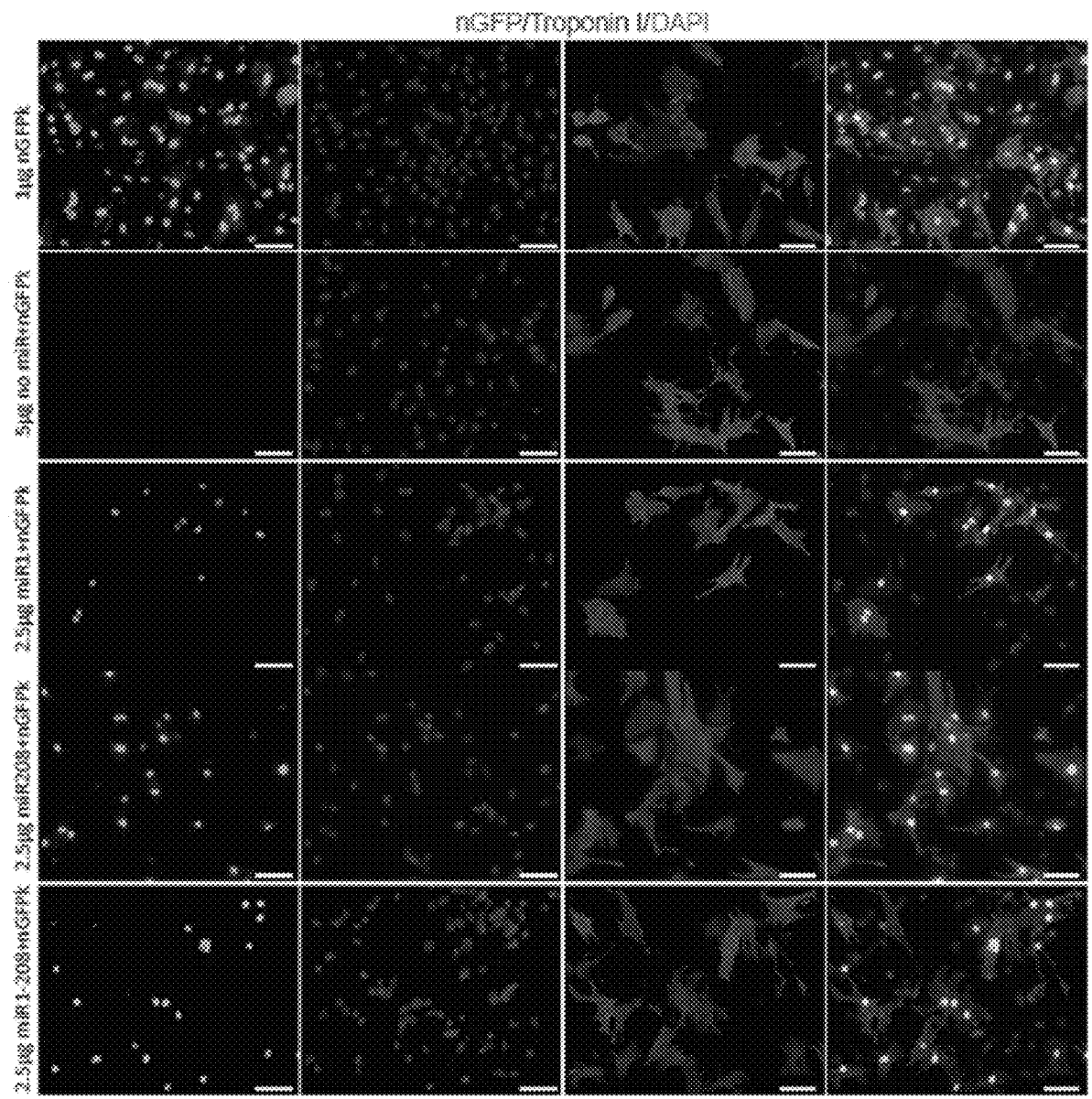
Figure 16C:
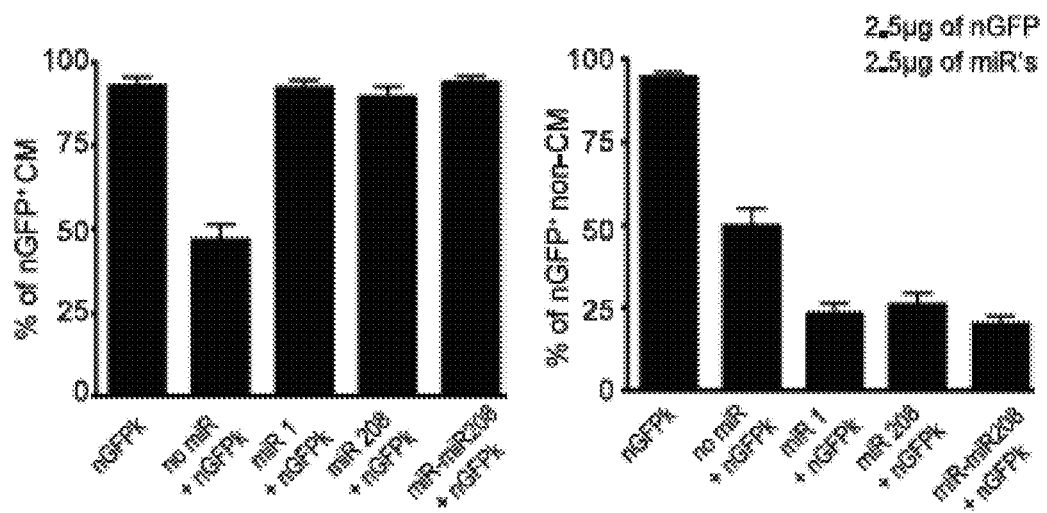

The differential expression of different cell cycle inducer genes in the heart changes during heart development. Others and we focused on two different time points after birth (Day 1 and Day 10) as they represent developmental stages that the heart has regenerative ability via CMs proliferation (day 1) and lacking this ability (day 10). As can be seen in FIG. 1a several cell cycle inducer changes significantly between the two stages of development. However Pkm2 levels in mice hearts are high during fetal development49 and are very significantly decreased by day 10 after birth. As Pkm2 most highly significant is upstream to several cell cycle inducer genes and his changes is the to Co-immunostaining of Pkm2 and the CMs marker α-Actinin revealed that Pkm2 was highly expressed in CMs during development and at one-day post birth, however, its expression was undetectable 8 weeks after birth (FIGS. 1 b&c). Pkm2 expression in the heart post-MI was restricted to immune cells (CD45+) and non-CMs but not upregulated in CMs (FIG. 11). We have restored Pkm2 levels by direct injection of Pkm2 modRNA into the myocardium (FIG. 1c). Pharmacokinetics study of Pkm2 levels after myocardial injection indicated that Pkm2 protein expression occurred a few hours post injection, and lasted for at least 8 days, but no longer than 12 days (FIG. 1d). To test the effect Pkm2 expression on CMs proliferation we isolated 4-day old neonatal rat CMs and transfected them with Luc control or Pkm2 modRNAs (FIGS. 12A-12C). Pkm2 modRNA was translated 12 hours post transfection and levels remained up to 10 days post transfection (FIGS. 12A-12C). Three days post transfection with Pkm2 or Luc modRNAs there was a significant increase in proliferation of Pkm2-transfected CMs (FIGS. 12A-12C). To test Pkm2 effects in MI setting, we directly injected Pkm2 or Luc modRNAs into the myocardium immediately after LAD ligation.13-15 One week post-MI and injection, Pkm2 significantly induced proliferation of CMs and non-CMs (FIGS. 1 e-h). We hypothesized that the observed improvement in proliferative capacity may translate into better regeneration, and result in improved outcome post-MI. However, inducing non-CMs proliferation in the heart frequently results in undesired effects, mainly by promoting fibrosis and immune response. Hence, we developed a unique CM-specific modRNA (cmsmodRNA) system that is based on two distinct modRNAs (FIG. 2, FIGS. 13A-13C and FIGS. 14A-14C). The first construct contains L7AE, an archaeal ribosomal protein that regulates the translation of genes containing a kink-turn motif (K-motif), a specific binding site for L7AE.50,51 Translation of L7AE modRNA suppresses the translation of the designed gene of interest modRNA when the two are co-transfected into the cell. By adding a CM-specific microRNA (cmsmiR) recognition element to the L7AE gene 3'UTR, we were able to prevent L7AE translation in CMs that abundantly and mostly exclusively express those miRs, allowing the translation of the gene of interest modRNA strictly in CMs (FIGS. 13A-13C). miR1-1 (miR-1), miR-208a (miR-208) and miR-199a (miR-199) are reported to be expressed mostly in CMs.52-54 We tested the expression of those miRs in our model by generating an inactive human CD25 (ihCD25) —a truncated gene containing only the extracellular domain of hCD25—as a reporter gene that can be immunostained when expressed on the surface of cells/tissues. We have designed two versions of the ihCD25 construct, with or without recognition elements for miR-1, miR-208 or miR-199. modRNAs were transfected into neonatal CMs (FIGS. 14A-14C), or injected using the MI model (FIGS. 2ga-c and FIGS. 14A-14C). miR-1 and miR-208 were found to be CM-specific, as indicated by positive ihCD25 staining in non-CM but not in CMs. We designed a L7AE modRNA that contains both miR-1 and miR-208 recognition elements (miR-1-208) (FIGS. 2d-k), and used a nuclear GFP modRNA (nGFP-K) and a Cre recombinase (Cre-K) modRNAs that contains a K-motif. In our MI model, transfection of nGFP-K resulted in the translation of nGFP in both CMs and non-CMs. However, when nGFP-K was co-transfected with miR-1-208, nGFP was exclusively translated in CMs (FIGS. 2e&f). Co-transfection Cre-K with miR-1-208 in our MI model using Rosa26 reporter mice (Rosa26mTmG) resulted in GFP expression strictly in CMs (FIG. 2g). Injection of Cre-K alone resulted in transfection efficiency of ~24.8% of heart section/~2600 cells in left ventricle (both CMs and non-CMs). However, Cre-K+miR1-208 combination resulted in transfection efficiency of 7.7%/~800 cells of exclusively CMs (FIG. 2h). We also showed that the non-mammalian protein L7AE does not exacerbate immune response post MI (FIGS. 15A-15C). We hypothesize that this is due to the already active immune response in the heart immediately post MI. We concluded that the use of L7AE in mice model is immunologically safe. To test the functionality of our cmsmodRNA delivery platform in our MI model, we directly injected Luc-K, miR1-208, Luc K+miR1-208, Pkm2-K, Pkm2+miR1-208 or Pkm2-K+miR1-208 (cmsPkm2). Seven days post transfection we measured the proliferation rate in the heart (FIG. 2i). Pkm2-K modRNA alone or Pkm2+miR1-208 significantly increased proliferation of both CMs and non-CMs (P<0.001) compared to Luc modRNA (FIGS. 2 j&k). However, cmsPkm2 modRNA significantly reactivated the proliferation of only CMs (P<0.001), with no significant influence on the proliferation of non-CMs. Using live imaging of neonatal rat CMs for 24 hours, we found that co-transfection of cmsPkm2 modRNA with cmsnGFP modRNA increased CMs proliferation in comparison to transfection with cmsnGFP modRNA alone (Supplemental Movie 1). Additionally, cmsPkm2 modRNA significantly reduced apoptosis and increased capillary density in the myocardium 2 or 7 days post-MI (FIGS. 16A-16C). MRI or echo showed that cmsPkm2 significantly increased the percentage of ejection fraction (FIGS. 3a-d and Supplemental Movies 2&3) and delta of percentage fractioning shortening from day 2 (baseline) to day 28 post-MI (FIG. 3d). Left ventricular internal diameter end systole was increased, while left ventricular internal diameter end diastole was significantly increased in cmsPkm2 mice compared to control 28 days post-MI (FIGS. 16A-6C). 28 days post-MI, Pkm2 or cmsPkm2 expression significantly reduced cardiac scar formation Additionally, no abnormality in the cardiac tissue (e.g. angioma, edema) was observed post injection of cmsPkm2 (FIGS. 3e&f), heart weight to body weight ratio was significantly increased (FIG. 3g) while CMs size was significantly decreased, indicating the CMs proliferation (FIG. 3h and FIGS. 16A-16C), and capillary density was significantly increased (FIG. 3i) in Pkm2 or cmsPkm2 modRNA transfections compared to controls. Lastly, cmsPkm2 significantly increased CMs number in the heart without elevating the number of nuclei per CM, while increasing the mononuclear fraction compared to control (FIGS. 3j-m). Importantly, long-term survival curve for mice treated immediately after MI with cmsLuc or cmsPkm2 modRNAs showed significant improvement in mice survival post-MI and cmsPkm2 transfection (FIG. 3n). To understand the mechanism by which cmsPkm2 improves cardiac function post-MI, we used a lineage-tracing model that combines cmsmodRNAs and R26mTmG (FIGS. 4a-j) to exclusively express Pkm2/Luc in CMs (by mixing cmsPkm2/cmsLuc+cmsCre modRNA; GFP-labeled CMs, FIGS. 4a&b), and trace the fate and properties of transfected CMs over time, after the cmsmodRNA was no longer expressed. The number of CMs transfected with cmsPkm2+Cre modRNAs was higher 3 days post-MI and significantly higher 28 days post-MI compared to control (FIGS. 4c&d). Heart weight to body weight ratio was significantly increased (FIG. 4e), while GFP+ CMs size (FIG. 4f) and nuclei number/cell (FIG. 4g) was significantly decreased in mice treated with cmsPkm2+ Cre modRNA compared to control. Importantly, 28 days post treatment with cmsPkm2+Cre modRNA, GFP+ CMs showed elevated expression of proliferative markers such as pH3 and Ki67 (FIGS. 4h-j), long after Pkm2 was not expressed. Changes in gene expression post cmsPkm2 or cmsihCD25 together with cmsihCD25 modRNAs delivery in MI setting were measured 2 days post injection. Isolated cells were enriched for CMs markers with significantly lower expression of Troponin T (FIG. 4k). Pkm2 expressing cells significantly upregulated effectors downstream of its cytoplasmic (G6pd) and nuclear (c-Myc, Cyclin D1, Bcl2, VEGF-A and Pdk1) functions (FIG. 4*l*). In accordance with the increased proliferation, we observed an upregulation of cell cycle-promoting genes (Cdc20, Cdk1 and Ccnd2, Ccnb1), and downregulation of the cell cycle inhibitors (p21 and p27) in Pkm2+ ihCD25+ CMs compared Luc+ ihCD25+ CMs (FIG. 4M).

Figure 17A:
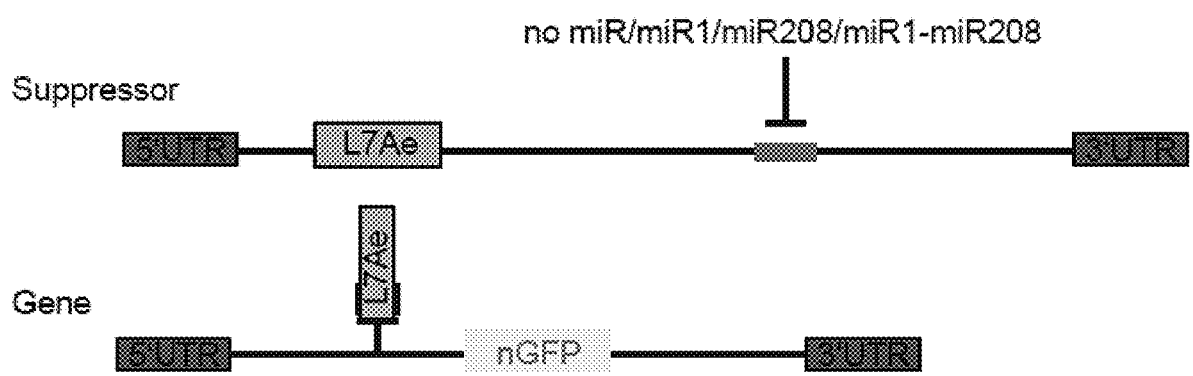
FIGS. 17A-17C show nGFP CMs-specific modRNA carrying recognition element for miR-208, miR-1, or both, in 1:2.5 ratio or higher, show nGFP translation exclusively in CMs in vitro. A CMs specific modRNA design. B nGFP CMs specific modRNA caring recognition element for miR-208, miR-1, or both, in different ratios, were transfected into neonatal rat CMs in vitro. 20 hours post transfection cells were fixed and stain for nGFP (green nuclear) and Troponin I (CM marker, red). C quantification of the experiment described in B. Results represent two independent experiments with n=3 wells, bar=10 mm.
Figure 17B:
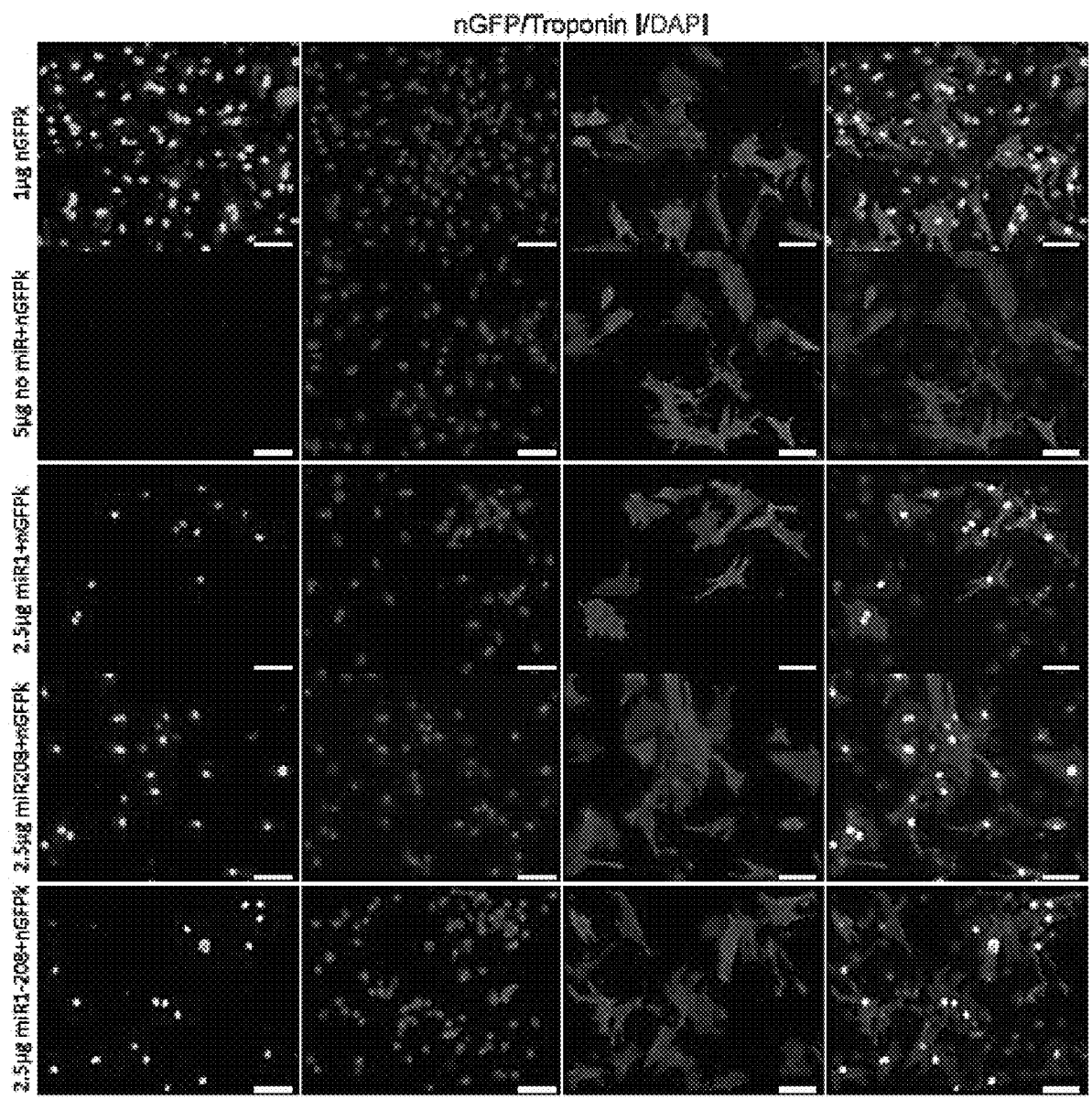
Figure 17C:
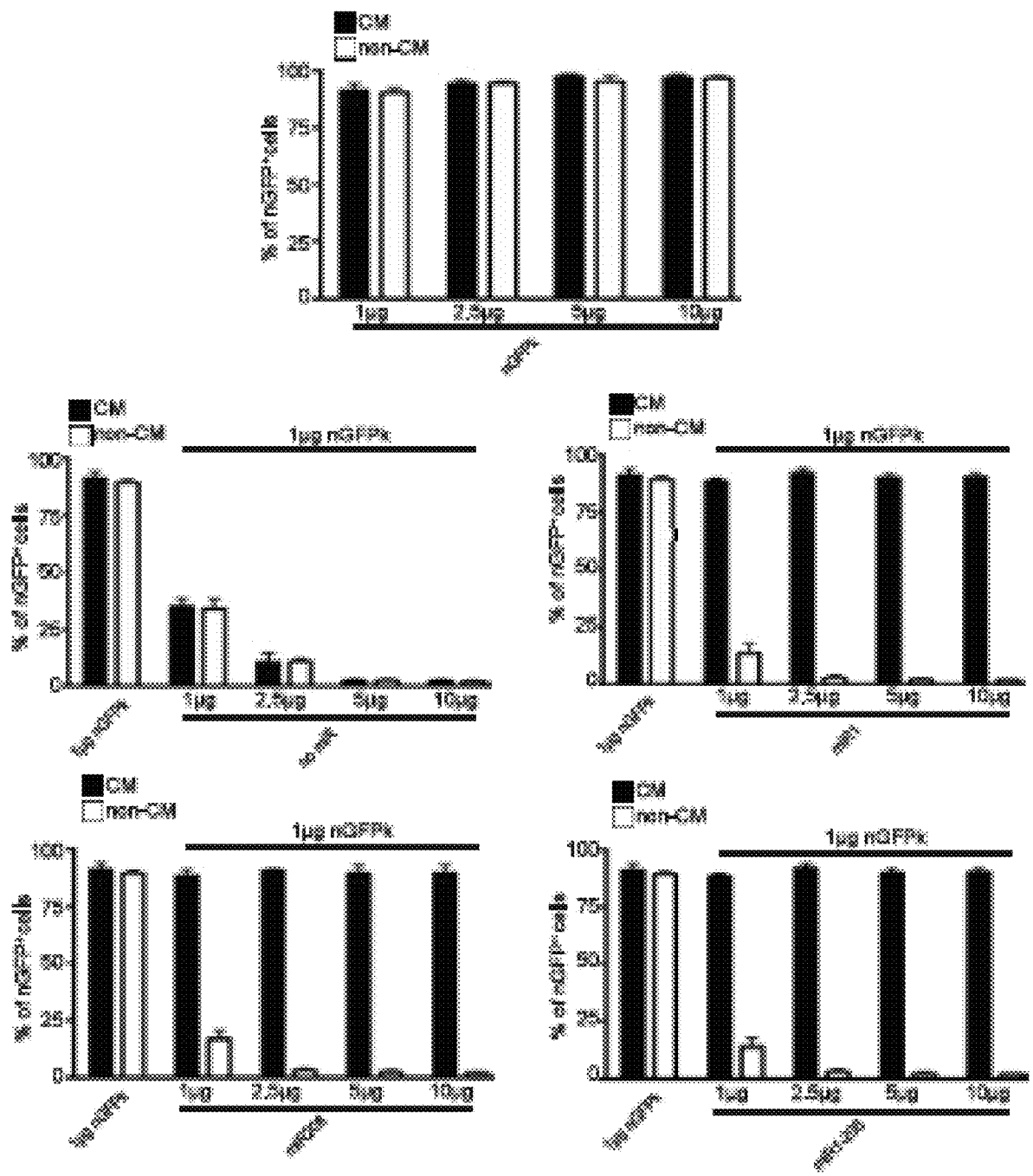
Figure 18:
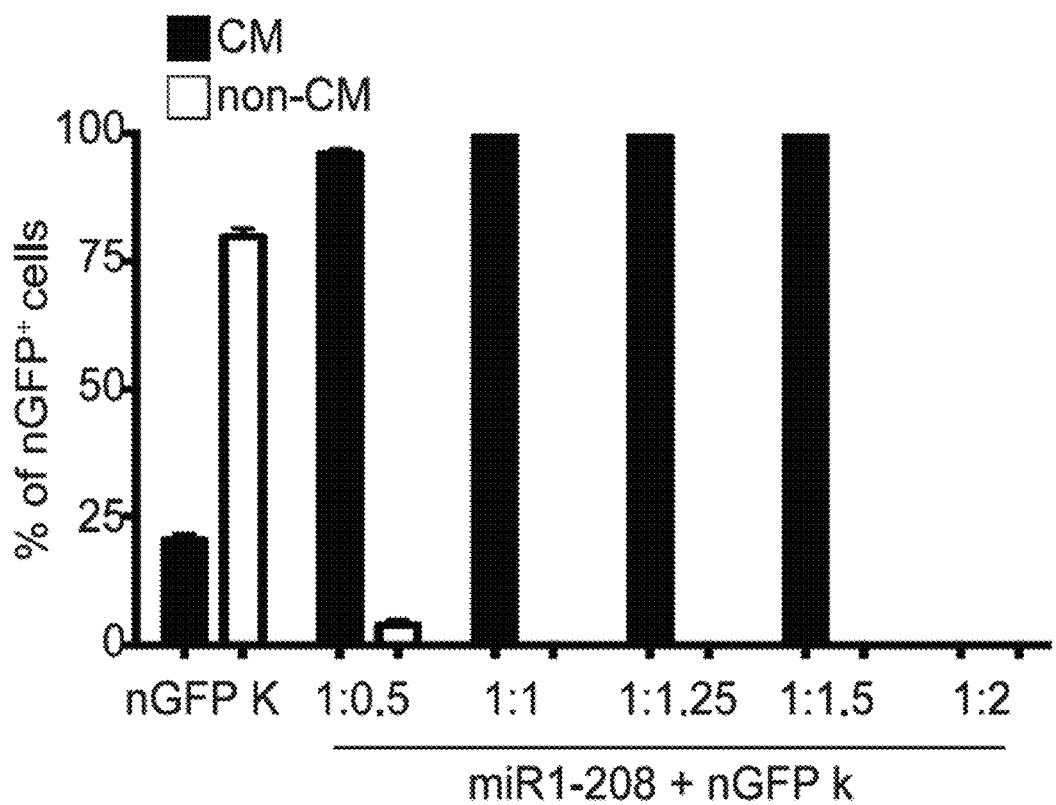
FIG. 18 nGFP CM-specific modRNA carrying recognition element for both miR-1 and miR-208, in 1:0.5 ratio or higher, show nGFP translation exclusively in CMs in vivo. Results represent two independent experiments with n=3 mice, bar=10 mm.
Figure 19A:
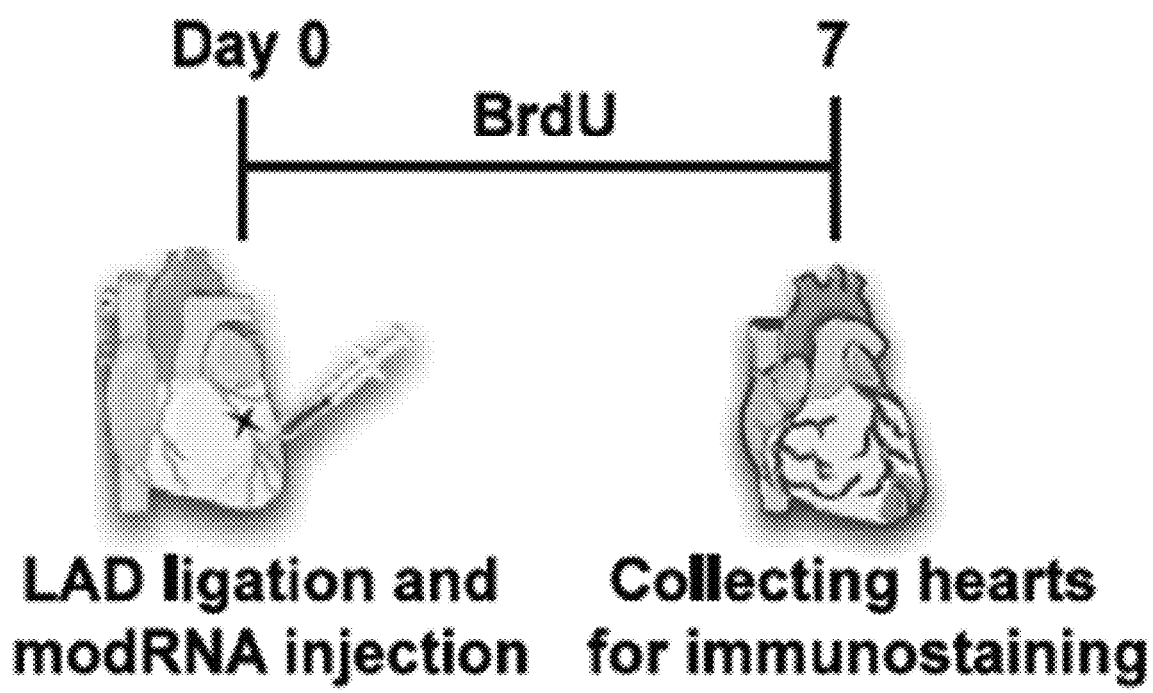
FIGS. 19A-19C Pkm2 CM-specific modRNA promotes proliferation exclusively in CMs. A Experimental time line. B modRNA design used in the experiments. C Lin28/PKM2 CMs-specific modRNA promotes proliferation exclusively in CMs. PKM2 modRNA carrying a k motif co-transfected with L7AE-miR1 and miR208 were tested for reactivation of adult mouse cardiomyocytes proliferation 7 days post-delivery in a mouse myocardial infarction model. Red dashed line represents control proliferation rate. Results represent 2 independent experiments with n=2 mice (total n=4 mice), ***P<0.001, N.S., Not significant; two-tailed student t-test.
Figure 19B:
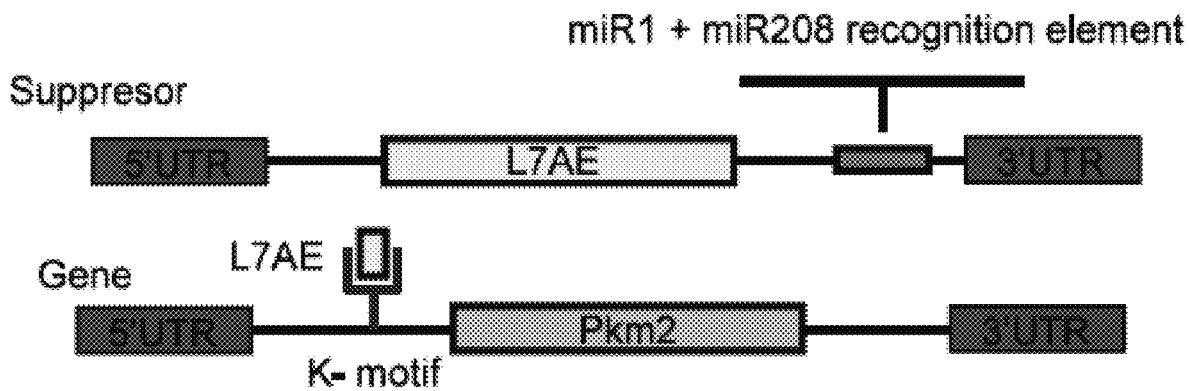
Figure 19C:
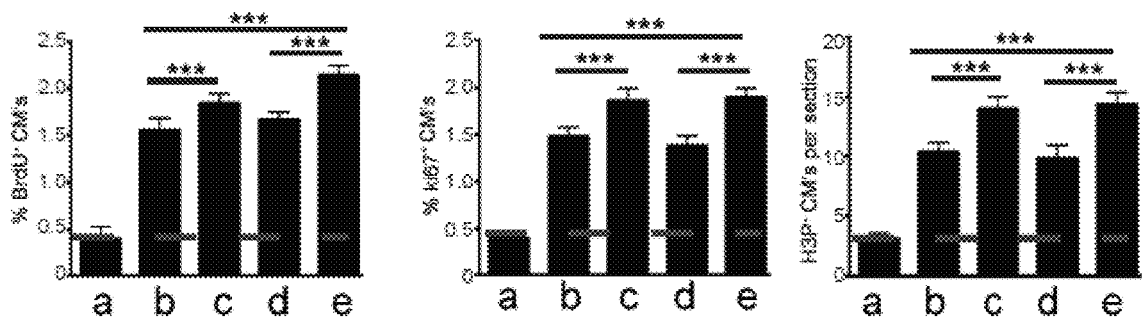
Figure 19C:
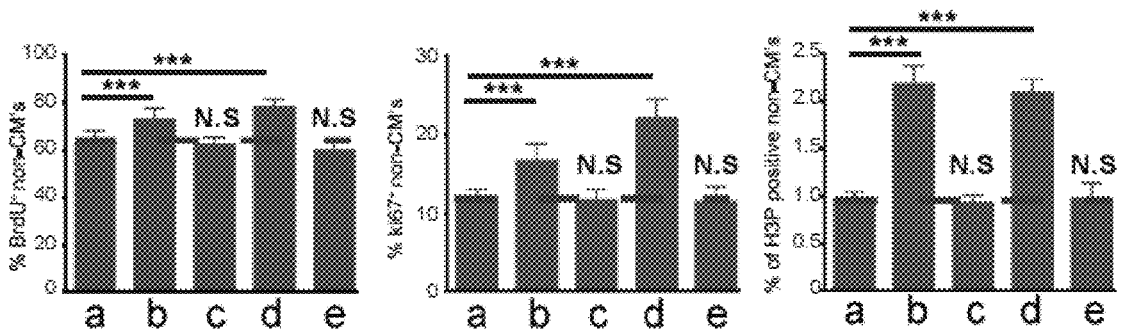
Figure 20:
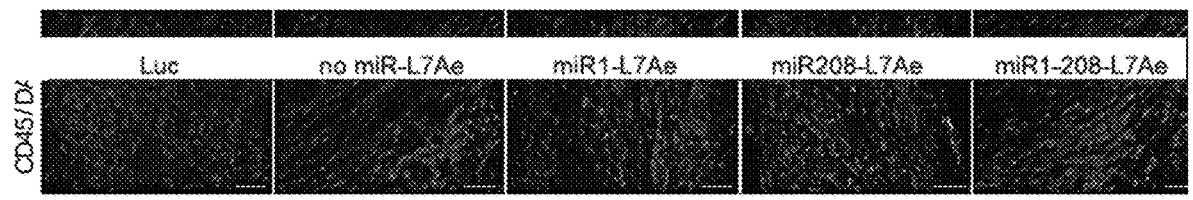
FIG. 20 L7AE modRNA did not elevate immune response in adult mouse myocardial infraction model. Quality images showing that no elevation in immune response (CD45+ cells, red) can be seen after L7AE is been delivered with or without recognition elements of different miRs. Scale bar=10 μm.
Figure 21A:
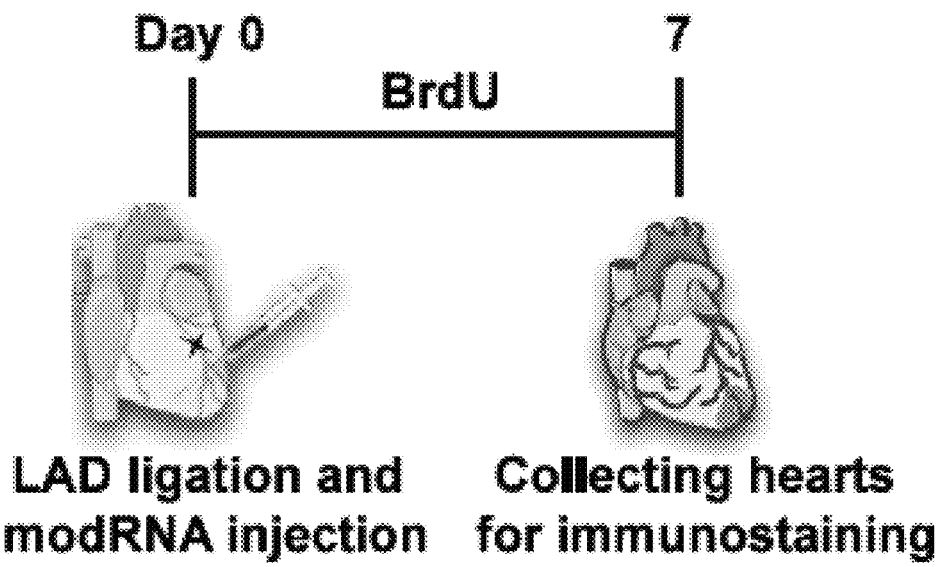
FIGS. 21A-21C Evaluation of L7AE modRNA with or without miR recognition element for miR-208 or miR1 or both on CMs proliferation and size, in vivo. A Mouse adult heart after MI was injected with Luc, L7AE without miR recognition element or with recognition element for miR-1 or miR-208 or both. 7 days post MI hearts were collected, fixed and stain for different proliferation markers such as Ki67, BrdU, H3P and Aurora B B and WGA for measuring CMs size in the treated hearts C Results indicate that L7AE with miR recognition element for miR-208 or miR-1 or both induce CM proliferation without compromising CMs size. Results represent two independent experiments with n=3 mice, N.S, not significant, ***, P<0.001, two-tailed student t-test.
Figure 21B:
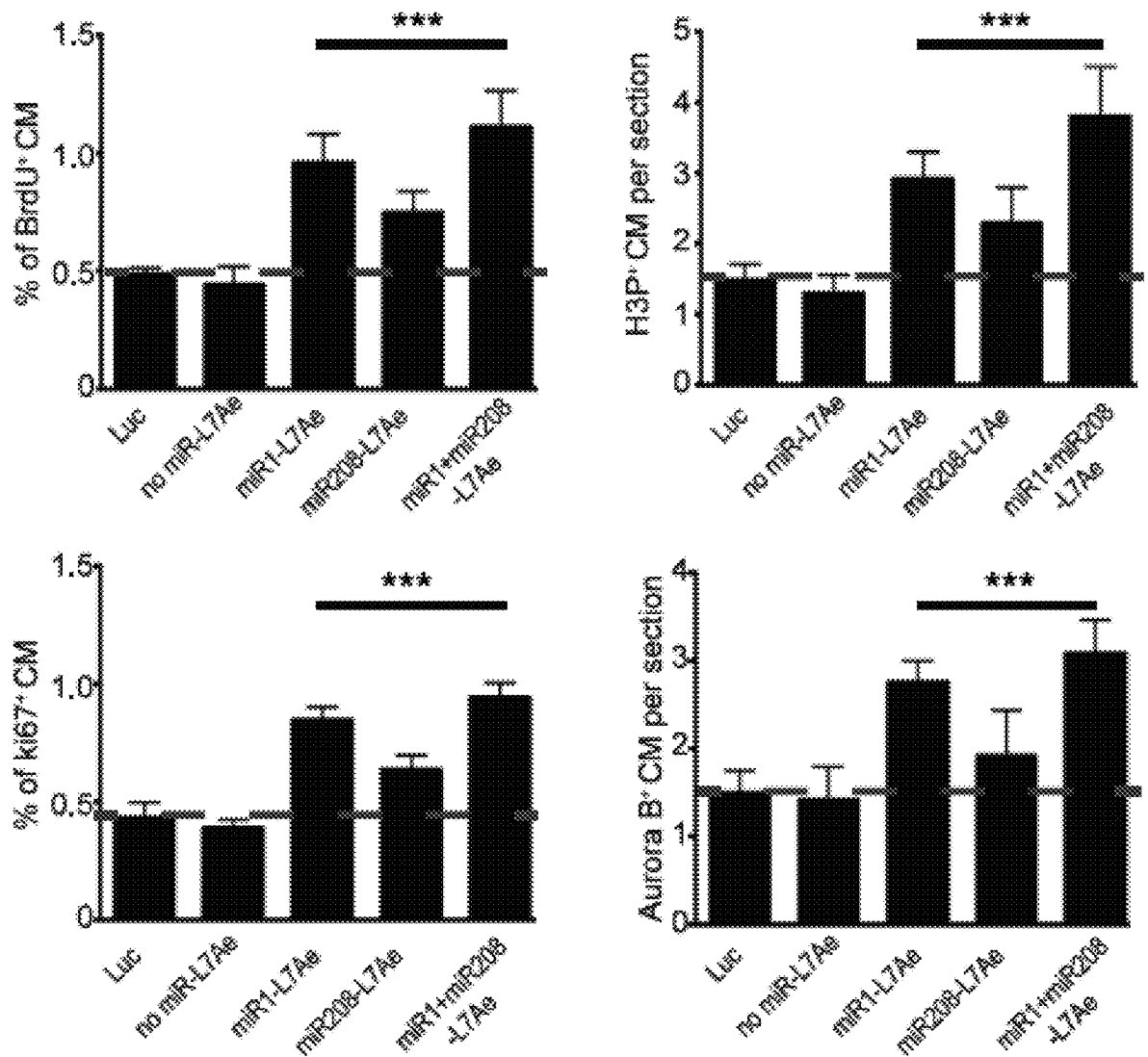
Figure 21C:
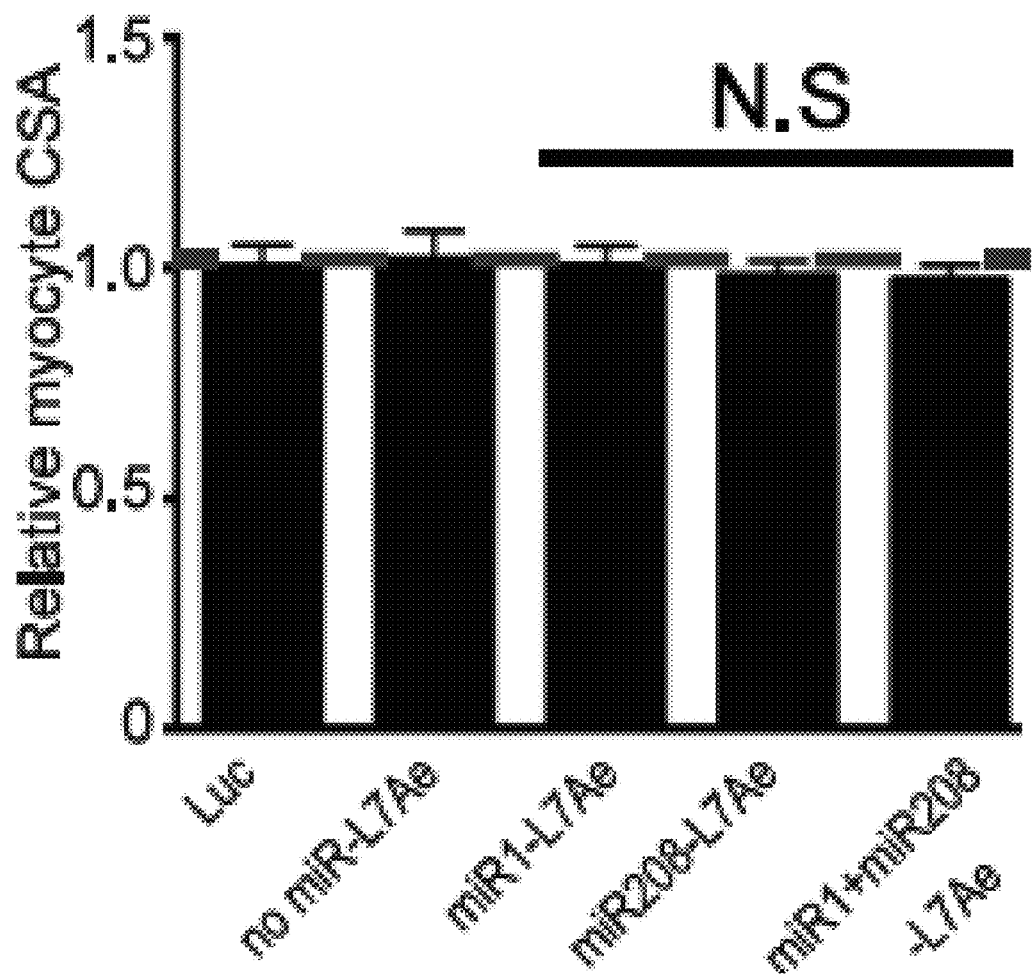
Figure 22A:
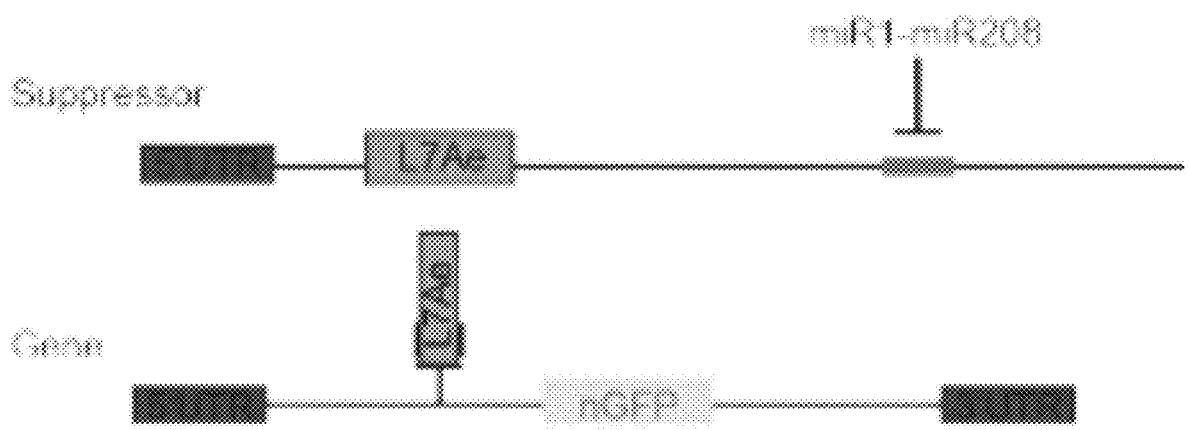
FIGS. 22A-22C show the transcriptional/translational regulatory system used to express nGFP.
Figure 22B:
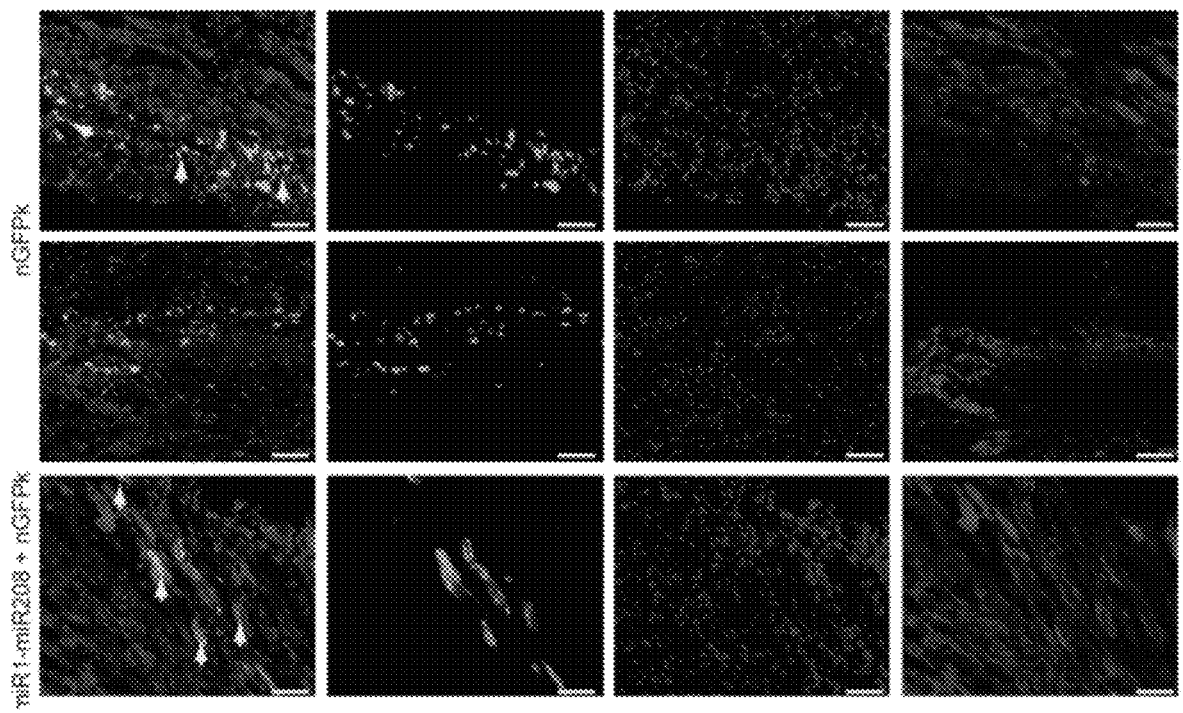
Figure 22C:
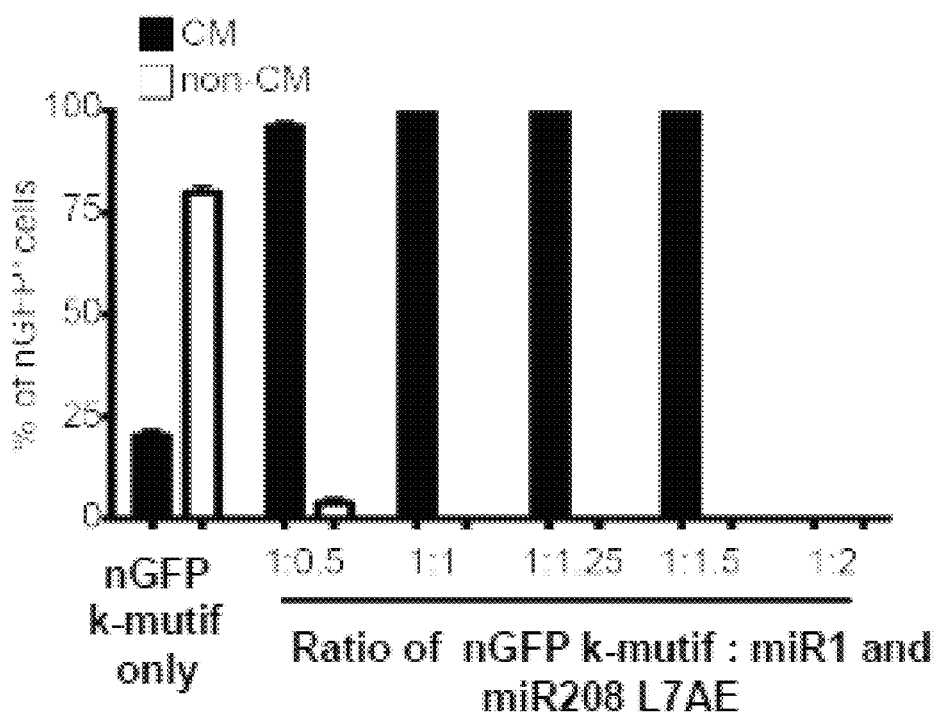
Figure 23A:
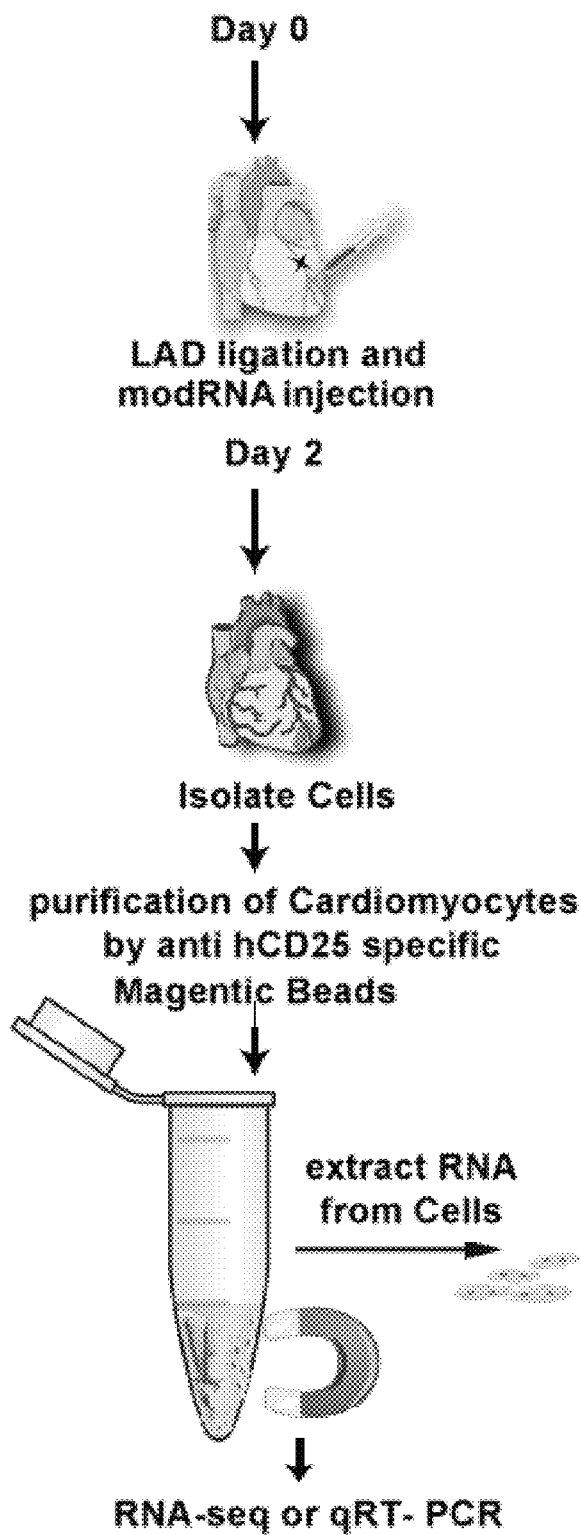
FIGS. 23A-23D show the results of isolation of transfected adult CMs from heart post MI using a CMs specific modRNA approach and magnetic bead sorting. A Isolation of adult CMs was performed 2 days post MI and modRNA administration. Anti-hCD25 magnetic beads were used to isolate CD25-positive cells. B CFW mice were transfected with ihCD25 and nGFP carrying the k motif. All positive cells isolated with this approach are GFP+ ihCD25+. C When transfected together with L7AE carrying recognition elements of miR1 and miR208 (CM specific modRNA) results in mixture of transfected CMs (nGFP+ and ihCD25+) and non-transfected CMs and no-cms. D Using hCD25 magnetic beads allows one to isolate only transfected CMs. Mice=3.
Figure 23B:
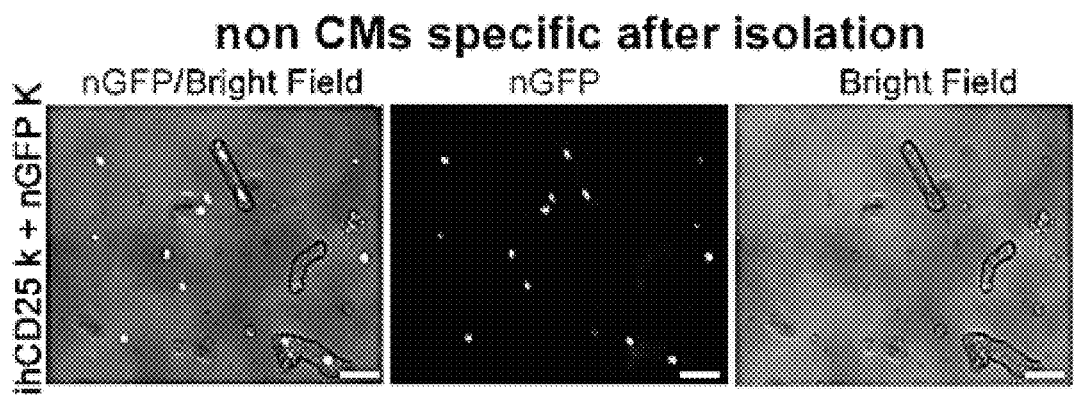
Figure 23C:
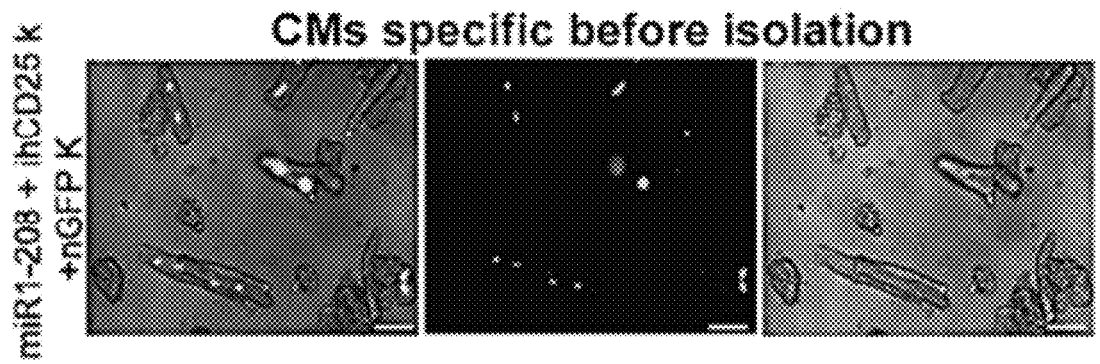
Figure 23D:
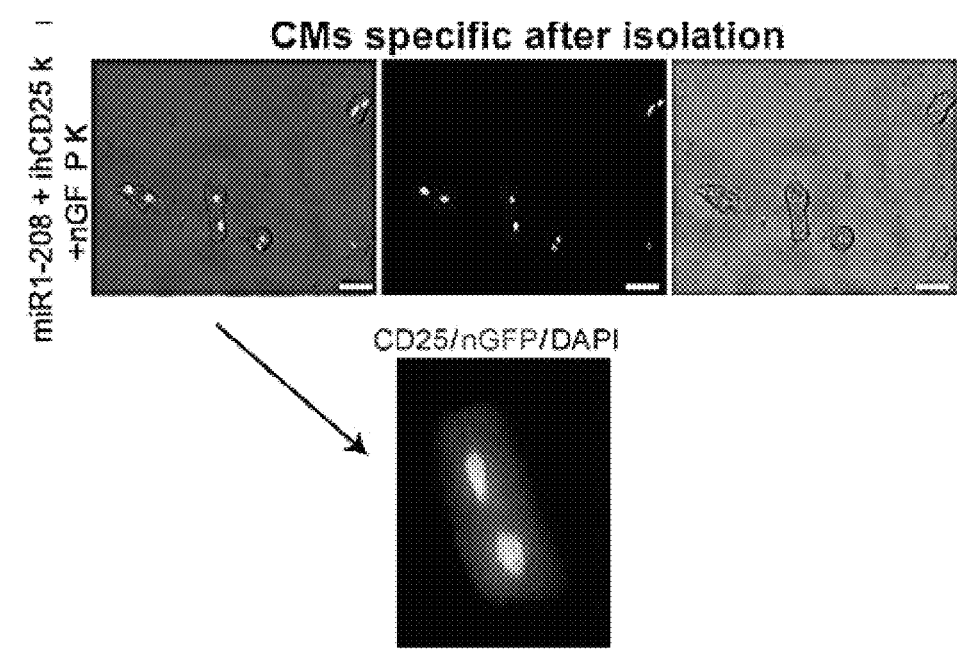
Figure 24:
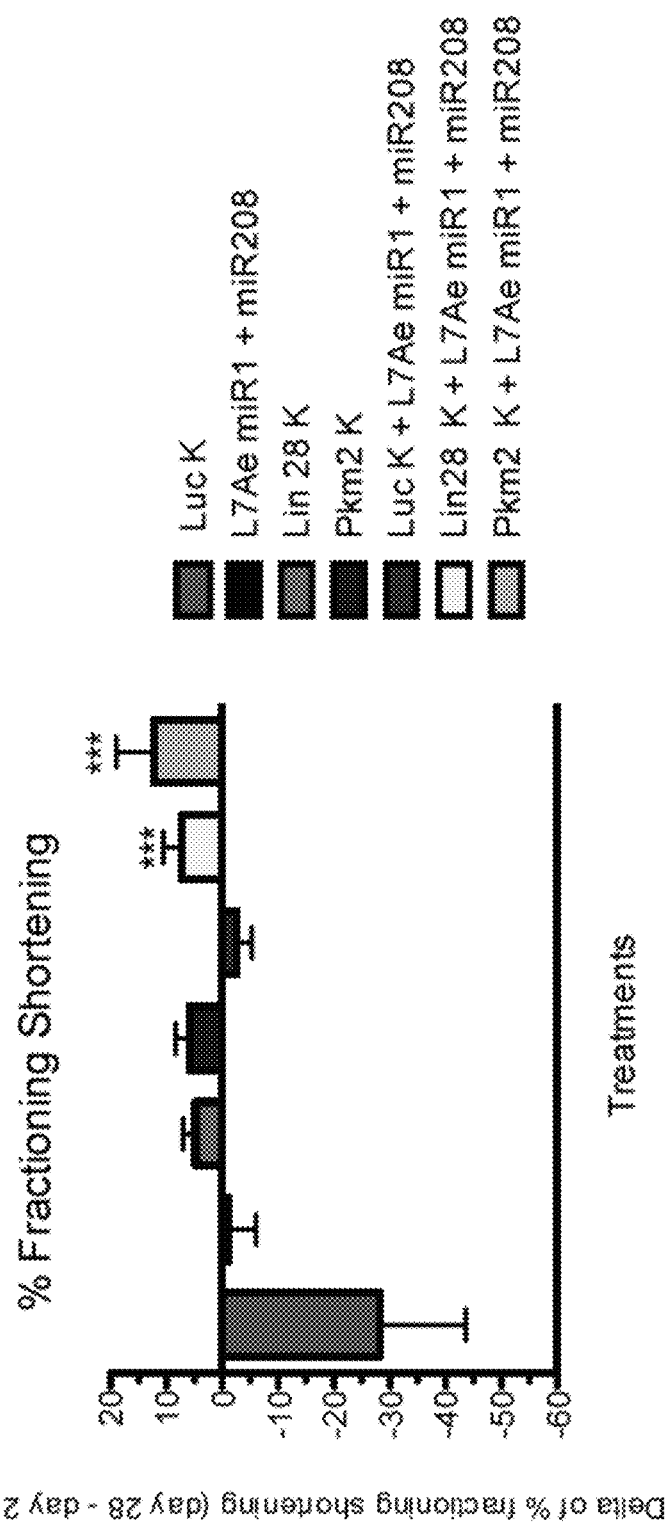
FIG. 24 shows that Lin28 or Pkm2 CMs specific modRNA improve cardiac function 28 days post MI and injection in mouse myocardial infraction model. Heart function was measured for different treated groups at day 2 and day 28 post MI using echocardiography. Results show improvement of cardiac function in Lin28 or Pkm2 treated groups with synergistic effect when Lin28 or Pkm2 were delivered in CMs specific manner (+L7Ae miR1+miR208). n=3 mice, ***, P<0.001, two-tailed student t-test.

The rapid downregulation of Pkm2 after birth, which coincides with the loss of cardiac regeneration ability,[55] points to its involvement in fetal and neonatal cardiac regeneration. Additionally, its previously-described pro-proliferative and pro-survival roles in cancer, make it an ideal candidate to promote cardiac function/regeneration. Our finding that $_{cms}$Pkm2 improves outcome after MI, most likely by improving cardiac function, has physiological and clinical implications, as they underline the potential therapeutic value of $_{cms}$Pkm2 expression immediately post-MI. Our results are in agreement with a recent publication showing that a short expression of synthetic miRs is sufficient for the induction of CMs proliferation and cardiac regeneration[56]. In addition, the cardiac specificity of our modRNA along with its short expression time make it a safe and translatable strategy for cardiac regeneration. Our data point to the high potency of Pkm2 and its ability to induce metabolic reprogramming that better supports CMs homeostasis with long-term beneficial effects, lasting weeks after the protein was no longer expressed. Our experimental approach and tools will allow us to further investigate other relevant pro-proliferative and metabolic reprogramming genes and their therapeutic potential in different disease models, and to efficiently and precisely study CMs cell fate. Notably, our isolation approach using $_{cms}$ihCD25 (FIGS. 17A-17C) overcomes the challenge of FACS sorting of adult transfected CMs.[31] This study pioneers the use of $_{cms}$modRNAs to manipulate cellular behavior and holds a great therapeutic potential for cardiac disease, as modRNA is a safe, transient, local, and non-immunogenic platform for gene transfer.

The field of cardiac gene therapy is expanding, yet its use in the clinical setting is limited. Currently the most widely used method for targeting gene expression to the heart is through viral vectors, particularly the adeno-associated virus (AAV) vector (1-3). During the past few decades several attempts were made to insert genes of interest into CMs using adenovirus, associate adeno virus (AAV), lentivirus and DNA plasmid. While both AAV and adenovirus possess high CM transfection levels, lentivirus and DNA plasmid CMs transfection efficiency is low. Adenoviruses can elicit a robust immune response, leaving only AAV as a suitable option for gene delivery system to the heart. Using CMs-specific promoters in AAV may allow for cell-cycle inducers gene expression strictly in CMs, however its pharmacokinetics in the heart (expression starts at day 4 and remains for at least 11 months) may lead to uncontrolled growth and hypertrophic cardiomyopathy and HF (3, 5). Additionally, over 60% of healthy human individuals possess neutralizing antibodies directed against the AAV capsid that can efficiently neutralize gene expression delivered by this method (21). Viral gene therapy shows promise yet its applications are limited due to its length of expression and inability to regulate gene expression in a quantifiable dose manner (1-3).

While the use of unmodified exogenous RNA as a gene delivery method is appealing because it may be safer than plasmid DNA owing to a reduced risk of genomic integration, it is ineffective due to its instability outside the cell and the strong innate immune response it elicits when transfected into cells (10,11).

Kariko et al. discovered that the substitution of Uridine and Cytidine with Pseudouridine and 5-methylcytidine, respectively, drastically reduced the immune response elicited from exogenous RNA (11,12). In order to increase stability and translational efficiency, a 3'-O-Me-m7G(5')ppp (5')G Anti Reverse Cap Analog (ARCA) cap is substituted at the 5' end of the RNA molecule (4,5,10). Modified mRNA (modRNA) therefore provides a novel and effective gene delivery method that provides short-term (1-2 weeks), titratable gene expression for use both in vitro or in vivo (4-9).

Modified mRNA (modRNA) has emerged as an effective and safe tool for somatic gene transfer, and has been successfully used by us and others for gene delivery to the heart.[10,12-15] Here we show that Pyruvate Kinase Muscle Isozyme M2 (Pkm2), a pro-proliferative factor, frequently dysregulated in cancer,[16,17] is highly expressed in regenerative fetal and early neonatal CMs, but not in adult CMs. Restoration of Pkm2 levels using modRNA delivery exclusively into adult CMs ($_{cms}$Pkm2) post-MI significantly and exclusively induced CMs proliferation, and was associated with improved cardiac function, reduced scar size, increased heart to body weight ratio, reduced CMs size, reduced apoptosis and increased capillary density. Those regenerative processes translated into increased long-term survival post-MI. Using lineage tracing and isolation of Pkm2-transfected CMs followed by gene expression analysis post-MI we show an increase in number of Pkm2-transfected CMs colonies and the potential involvement of key downstream effectors of the pro-proliferative cytoplasmic (via the pentose phosphate pathway (PPP)[18,19]) and nuclear (via trans-activation of β-catenin and Hif1α[20,21]) functions of Pkm2. Our results show that a short pulse of a pro-proliferative gene, using a highly translatable, clinically adaptable platform is sufficient to induce CM proliferation and cardiac regeneration. Those findings underline the therapeutic potential of $_{cms}$Pkm2 modRNA in cardiac disease.

It has recently been shown (1) that by using modified mRNA (modRNA) technology, modRNA can drive a transient, safe gene expression in the heart with high transfection levels without eliciting immune response or compromising the genome(5, 22). Exogenous unmodified mRNA that enters the cell via the cell membrane is recognized by endosomal Toll-like receptors 7/8 and 3(23, 24). This process inhibits protein translation and activates the innate immune response, ultimately leading to apoptosis of the hosting cell. ModRNA is synthesized by substituting ribonucleotides with naturally modified ribonucleotides. The use of these modified ribonucleotides results in changing the secondary structure of the synthesized mRNA, which prevents the Toll-like receptors from recognizing the modRNA and therefore permitting its translation to a functional protein by the ribosomal machinery without eliciting immune response or compromising the genome (5, 22).

Applicants previously showed that modRNA transfects different cell types in the heart including CMs with high efficiency, leading to immediate and high levels of protein expression in a transient, pulse like kinetic (duration of 3-5 days in vitro and 7-10 days in vivo). Co-transfection of two individual modRNAs resulted in co-translation of both. Using the MI model (5) and Luc, LacZ and nGFP modRNAs delivery in myocardium, Applicants show that the cardiac tissue after MI is well transfected with modRNA and several cell types such as CMs and non-CMs are highly transfected in the left ventricle. Applicants then selected several candidate cell cycle inducer genes that had previously been shown to have the ability to induce neonatal CMs during cardiac development (CDK2, β catenin) (16) or reactivation of adult CMs proliferation in transgenic mouse models (CyclinD2, cMYC)(12, 14) and others that had shown robust proliferative potential in different organs and cell types but had never been tested in cardiomyocytes and heart (Lin28, PKM2)(24, 25).

Generally, a platform for making cell specific modified mRNA (modRNA) is as follows.

First, choose a cell type of interest for making cell specific modRNA. Identify candidate microRNA (miR) that have been reported to express in the cell of interest and preferably only in the cell of interest (e.g., in the case of cardiomyocytes, miR1, miR29, miR126, miR133, miR199, miR208, miR378). Identify reverse complement sequences for each miR sequence that allows recognition of the specific miR to this sequence. Add to 3'UTR each of the previous calculated miR reverse complement sequence to ihCD25 k motif, a truncated receptor for hCD25 carrying a k motif. This allows ihCD25 to express only in those cells that are lacking the specific miR that the reverse complement sequence is targeting.

Co-transfect a mixture of cells that contains the cell of interest and other cell type (e.g fibroblasts) as well with nGFP modRNA and with different miR-ihCD25 modRNAs. After about 18 hours, fix the cells and stain the cells for GFP (show transfected cells with modRNA) and for reporter gene (with anti hCD25, show cells that are lacking the miR that was target) and cell specific markers (e.g., for cardiomyocytes Troponin I, for endothelial cells, Pecam1, etc.).

Identify GFP-positive cells that are also positive for cell specific marker (e.g Troponin I for cardiomyocytes) but negative for reporter gene (hCD25). This means that this specific miR-ihCD25 was not translated although the modRNA was delivered to this cell type. This will indicate that this miR is specifically expressed in the cell type of interest and can be used to create cell specific modRNA. Create cell specific modRNA by adding to the 3'UTR of L7AE the sequence that inhibits ihCD25 in the cell of interest. Co-transfect with mir-L7AE and gene of interest that carrying in his 5' UTR k-motif. These two modRNAs will allow you to specifically deliver a gene of interest to a specific cell type.

In one embodiment, Applicant designed and generated modRNAs for each of the above genes. Using rat neonatal CMs, Applicant tested the translation of each modRNA. In addition, the functionality of the protein was tested by measuring the proliferation rate of rat neonatal CMs with control and the candidate cell inducer modRNAs. All candidate cell cycle inducer modRNAs increase the proliferation of neonatal rat CMs and adult CMs proliferation after MI to various extents. Both Lin28 and PKM2 significantly increased CMs proliferative capacity. Therefore, those genes were selected for further investigation.

Lin28 is a known suppressor of Let7 that tightly controls cell cycle regulators (25-29). To test whether Lin28 induces cell cycle regulators, nGFP (control modRNA) or Lin28 modRNA was injected immediately after LAD ligation and found a significant increase in the expression of Ccnb1, Ccnb2, Cdc20, Cdk1 and Aurka cell cycle genes after 3 days using RT-PCR. The use of cell cycle inducer modRNAs such as Lin28 modRNA in a non-specific manner increases proliferation not only in CMs, but also non-CMs representing an experiential challenge since the model and hypothesis were aimed to test aimed to test CMs proliferation as a mean to achieve increased cardiac regeneration.

Figure 5A:
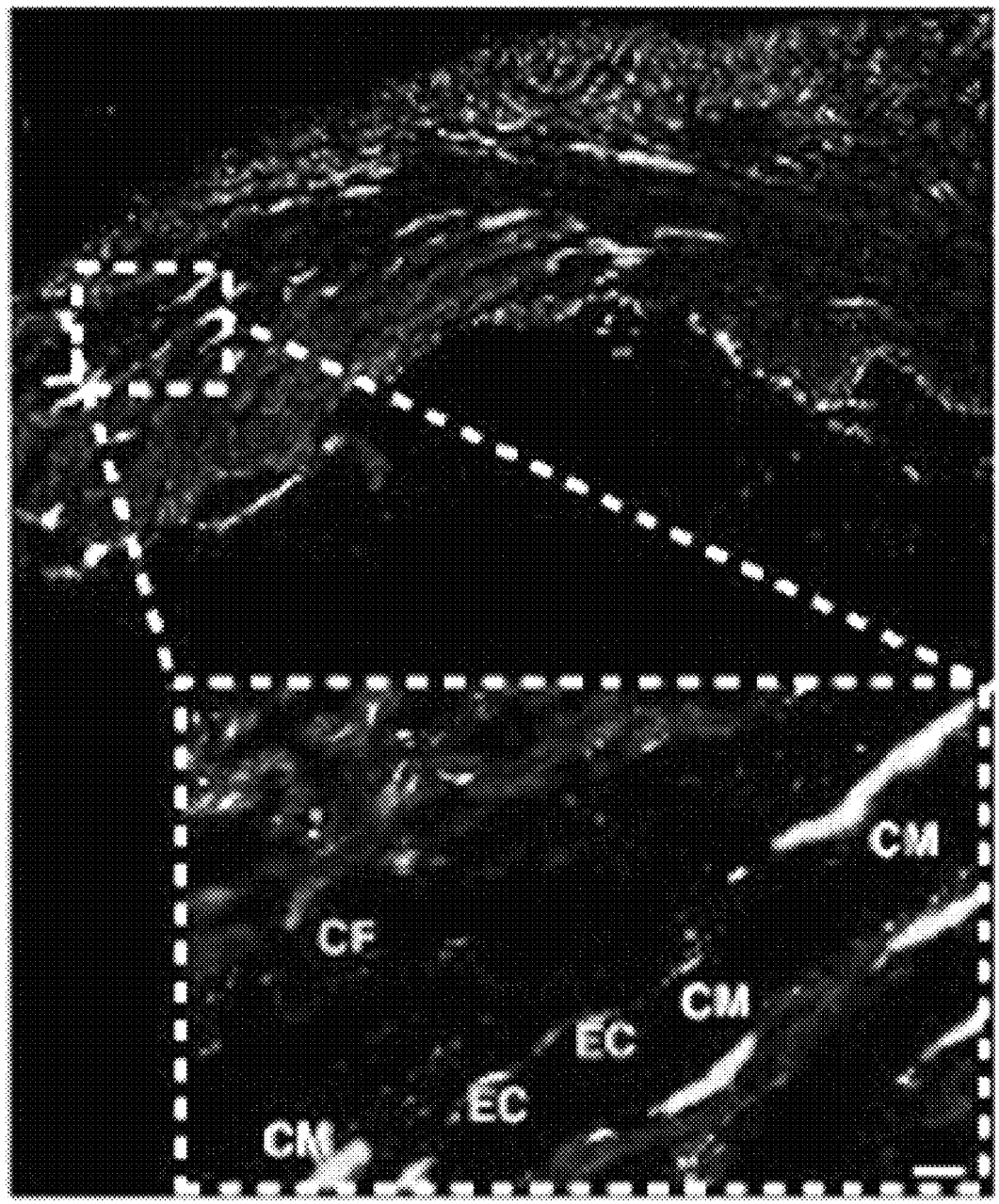
FIGS. 5A and 5B shows adult mouse myocardial infarction and heart failure models. Adult mouse myocardial infarction model (MI model) is performed using a permanent ligation of left anterior descending coronary artery (LAD) following direct intramuscular injection of modRNA. One or more days post MI, hearts are collected and used for immunostaining. B Adult mouse heart after MI is highly transfected with Luc; LacZ and nGFP modRNAs. A Several cell types are transfected with modRNA, including cardiomyocytes (CM), cardiac fibroblasts (CF) and endothelial cells (EC).
Figure 5B:
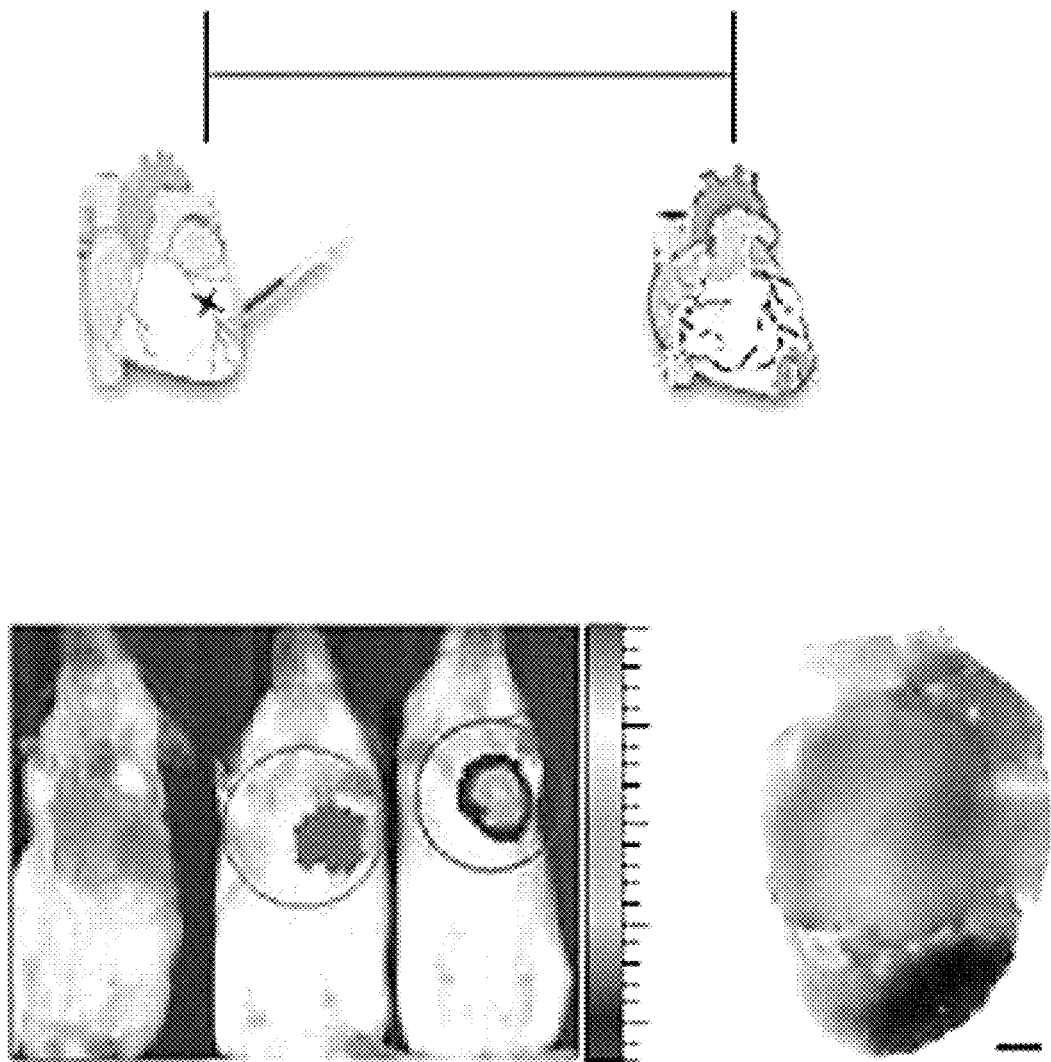

To address this challenge Applicants designed a CM-specific modRNA system that is based on two distinct modRNAs (FIG. 5). The first construct is a suppressor modRNA the carries L7AE, an archaeal ribosomal protein that regulates the translation of a designed gene of interest modRNA with kink-turn motif—a specific binding site for L7AE(30, 31). Translation of L7AE modRNA will suppress the translation of the designed gene of interest modRNA when the two are co-transfected into the cell. By adding a CMs-specific microRNA (miR) recognition element to the L7AE gene, we are able to prevent L7AE translation in CMs that abundantly and mostly exclusively express the miR ("suppress the suppressor" approach) allowing the translation of the gene of interest modRNA strictly in CMs. It was shown previously, using miR recognition element, results in a reduction of the number of copies of the targeted miR (32,33). Reduction in number of miRs in the heart can be detrimental or beneficial to the heart (33-42). In our approach we need to be sure we don't reduce miR expression that is beneficial to cardiac regeneration but rather reducing miR expression that is detrimental to cardiac regeneration. miR1-2 (miR1), miR208a (miR208) and miR199a (miR199) are expressed mostly in CMs (33, 39, 41). miR1 and miR208 were found to be upregulate after MI in adult animal study and humans (33, 38, 41, 43). miR1 and miR208 up regulation has detrimental effects, while its down regulation has beneficial effects after MI and heart diseases (32-42)

To test the expression of these miRs in CMs, we have made an inactive human CD25 (ihCD25) gene, a truncated gene containing only the extracellular domain (ECD) of hCD25—as a reporter gene. We have designed two versions of the ihCD25 construct, with or without the miR recognition elements for miR-1, miR-208 or miR-199. We then transfected the modRNAs into neonatal CMs in vitro and in vivo using the MI model (FIG. 2). As can be seen in FIG. 6 both miR-1 and miR-208 were found to be CM-specific, as translation of ihCD25 was observed in non-CM but not in CMs. In contrast, modRNAs with or without miR-199 recognition element was found not to be CMs specific, in vitro and in vivo. Next, we designed a L7AE modRNA that carries both miR-1 and miR-208 recognition elements (L7AE miR-1+miR-208). We have also generated a nuclear GFP modRNA (nGFP–k-motif) and a destabilized Cre recombinase (DD-Cre–k motif) modRNAs that includes the k-motif (L7AE recognition site). Using our adult mouse MI model, we show that transfection of nGFP–k motif resulted in the translation of nGFP in both CMs and non-CMs (FIG. 7). However, when nGFP–k motif was co-transfected with L7AE miR-1+miR-208 only CMs translated the nGFP. In addition, co-transfecting L7AE miR-1+miR-208 with a DD-Cre–k motif in a MI model using Rosa26$^{Tdtomato}$ resulted in gene activation (Tomato fluorescence) strictly in CMs. The combination of these two methods allows us to elegantly express our gene/genes of interest exclusively in CMs, and to allow for linage tracing over longer time periods after the gene of interest modRNA is no longer expressed.

To test the functionality of our CMs-specific modRNA, we directly inject Luc control modRNA or Lin28-K and PKM2-k motif modRNA alone or together with L7AE miR-1+miR-208 (Lin28/PKM2 CMs specific modRNA) using our MI model. Seven days post transfection we measured the proliferation (using hallmark proliferation markers, BrdU, Ki67, H3P and Aurora B) of both CMs and non-CMs. As depicted in FIG. 8 Lin28-k or PKM2-k motif modRNA alone significantly increased proliferation of both CMs and non-CMs (P<0.001) in comparison to Luc modRNA. However, Lin28 and PKM2 CMs-specific modRNA significantly reactivated the proliferation of only CMs (P<0.001), with no significant influence on the proliferation of non-CMs. Importantly, since L7AE is not a mammalian protein, to test the immunogenicity of L7AE after MI we have injected Luc control modRNA or L7AE modRNA with or without miR-1, miR-208 or both in adult mouse MI model. As can be seen in FIG. 8 we did not witness significant elevations in immune response and increased apoptosis with all L7AE modRNAs after 7 day post MI. We concluded that the use of L7AE in mice is immunologically safe.

Plasmids pTEMPLZ is a cloning vector into which an ORF of interest can be inserted between the UTRs. In one embodiment, plasmids for use in the disclosed method include those shown in Table 1.

TABLE 1

```
1  No miR-L7AE
   TTGGACCCTCGTACAGAAGCTAATACGACTCACTATAGGGAAATAAGAGAGAAAAG
   AAGAGTAAGAAGAAATATAAGAGCCACCatgtacgtgagatttgaggttcctgaggacatgcagaacg
   aagctctgagtctgctggagaaggttagggagagcggtaaggtaaagaaaggtaccaacgagacgacaaaggctgtg
   gagaggggactggcaaagctcgtttacatcgcagaggatgttgacccgcctgagatcgttgctcatctgccctcctctgc
   gaggagaagaatgtgccgtacatttacgttaaaagcaagaacgaccttggaagggctgtgggcattgaggtgccatgcg
   cttcggcagcgataatcaacgagggagagctgagaaaggagcttggaagccttgtggagaagattaaaggccttcaga
   agtaaGCTGCCTTCTGCGGGGCTTGCCTTCTGGCCATGCCCTTCTTCTCTCCCTTGC
   ACCTGTACCTCTTGGTCTTTGAATAAAGCCTGAGTAGGAA (SEQ ID NO: 1)

2  miR 1-L7AE
   TTGGACCCTCGTACAGAAGCTAATACGACTCACTATAGGGAAATAAGAGAGAAAAG
   AAGAGTAAGAAGAAATATAAGAGCCACCatgtacgtgagatttgaggttcctgaggacatgcagaacg
   aagctctgagtctgctggagaaggttagggagagcggtaaggtaaagaaaggtaccaacgagacgacaaaggctgtg
   gagaggggactggcaaagctcgtttacatcgcagaggatgttgacccgcctgagatcgttgctcatctgccctcctctgc
   gaggagaagaatgtgccgtacatttacgttaaaagcaagaacgaccttggaagggctgtgggcattgaggtgccatgcg
   cttcggcagcgataatcaacgagggagagctgagaaaggagcttggaagccttgtggagaagattaaaggccttcaga
   agtaaTACATACTTCTTTACATTCCATACATACTTCTTTACATTCCATACATACTTCTTT
   ACATTCCATACATACTTCTTTACATTCCAGCTGCCTTCTGCGGGGCTTGCCTTCTG
   GCCATGCCCTTCTTCTCTCCCTTGCACCTGTACCTCTTGGTCTTTGAATAAAGCCT
   GAGTAGGAA (SEQ ID NO: 2)

3  miR 208a-L7AE
   TTGGACCCTCGTACAGAAGCTAATACGACTCACTATAGGGAAATAAGAGAGAAAAG
   AAGAGTAAGAAGAAATATAAGAGCCACCatgtacgtgagatttgaggttcctgaggacatgcagaacg
   aagctctgagtctgctggagaaggttagggagagcggtaaggtaaagaaaggtaccaacgagacgacaaaggctgtg
   gagaggggactggcaaagctcgtttacatcgcagaggatgttgacccgcctgagatcgttgctcatctgccctcctctgc
   gaggagaagaatgtgccgtacatttacgttaaaagcaagaacgaccttggaagggctgtgggcattgaggtgccatgcg
   cttcggcagcgataatcaacgagggagagctgagaaaggagcttggaagccttgtggagaagattaaaggccttcaga
   agtaaACAAGCTTTTTGCTCGTCTTATACAAGCTTTTTGCTCGTCTTATACAAGCTTTT
   TGCTCGTCTTATACAAGCTTTTTGCTCGTCTTATGCTGCCTTCTGCGGGGCTTGCC
   TTCTGGCCATGCCCTTCTTCTCTCCCTTGCACCTGTACCTCTTGGTCTTTGAATAAA
   GCCTGAGTAGGAA (SEQ ID NO: 3)

4  miR 1-miR 208a-L7AE
   TTGGACCCTCGTACAGAAGCTAATACGACTCACTATAGGGAAATAAGAGAGAAAAG
   AAGAGTAAGAAGAAATATAAGAGCCACCatgtacgtgagatttgaggttcctgaggacatgcagaacg
   aagctctgagtctgctggagaaggttagggagagcggtaaggtaaagaaaggtaccaacgagacgacaaaggctgtg
   gagaggggactggcaaagctcgtttacatcgcagaggatgttgacccgcctgagatcgttgctcatctgccctcctctgc
   gaggagaagaatgtgccgtacatttacgttaaaagcaagaacgaccttggaagggctgtgggcattgaggtgccatgcg
   cttcggcagcgataatcaacgagggagagctgagaaaggagcttggaagccttgtggagaagattaaaggccttcaga
   agtaaTACATACTTCTTTACATTCCATACATACTTCTTTACATTCCATACATACTTCTTT
   ACATTCCATACATACTTCTTTACATTCCAACAAGCTTTTTGCTCGTCTTATACAAGCT
   TTTTGCTCGTCTTATACAAGCTTTTTGCTCGTCTTATACAAGCTTTTTGCTCGTCTTA
   TGCTGCCTTCTGCGGGGCTTGCCTTCTGGCCATGCCCTTCTTCTCTCCCTTGCACC
   TGTACCTCTTGGTCTTTGAATAAAGCCTGAGTAGGAA (SEQ ID NO: 4)

5  Lin28-K motif
   TTGGACCCTCGTACAGAAGCTAATACGACTCACTATAGGGAAAGGTGGGCGTGAT
   CCGAAAGGTGACCCGGATCTGGGGCGTGATCCGAAAGGTGACCCGGAAAGCCAC
   Catgggctcggtgtccaaccagcagtttgcaggtggctgcgccaaggcagcggagaaggcgccagaggaggcgccg
   cctgacgcggcccgagcggcagacgagccgcagctgctgcacggggccggcatctgtaagtggttcaacgtgcgcat
   ggggttcggcttcctgtctatgaccgcccgcgctggggtcgcgctcgaccccccggtggacgtcttttgtgcaccagagcaa
   gctgcacatggaagggttccgaagcctcaaggaggtgaggcggtggagttcaccttttaagaagtctgccaagggtctg
   gaatccatccgtgtcactggccctggtggtgtgttctgtattgggagtgagcggcggccaaaagggaagaacatgcagaa
   gcgaagatccaaaggagacaggtgctacaactgcggtgggctagaccatcatgccaaggaatgcaagctgccaccc
   agcccaagaagtgccacttttgccaaagcatcaaccatatggtggcctcgtgtccactgaaggcccagcagggcccag
   ttctcagggaaagcctgcctacttccgggaggaagaggaagagatccacagccctgccctgctcccagaagcccaga
   attgaGCTGCCTTCTGCGGGGCTTGCCTTCTGGCCATGCCCTTCTTCTCTCCCTTGC
   ACCTGTACCTCTTGGTCTTTGAATAAAGCCTGAGTAGGAA (SEQ ID NO: 5)

6  Pkm2-K motif
   TTGGACCCTCGTACAGAAGCTAATACGACTCACTATAGGGAAAGGTGGGCGTGAT
   CCGAAAGGTGACCCGGATCTGGGGCGTGATCCGAAAGGTGACCCGGAAAGCCAC
   Catgccgaagccacacagtgaagcagggactgccttcattcagacccagcagctccatgcagccatggctgacacctt
   cctggaacacatgtgccgcctggacattgactctgcccccatcacggcccgcaacactggcatcatttgtaccattgggcct
   gcttcccgatctgtgggagatgctgaaggagatgattaagtctggaatgaatgtggctcggctgaatttctctcatggaaccca
```

TABLE 1-continued

```
tgagtaccatgcagagaccatcaagaatgtccgtgaagccacagaaagctttgcatctgatcccattctctaccgtcctgtt
gcggtggctctggatacaaagggacctgagatccggactggactcatcaagggcagcggcaccgctgaggtggagct
gaagaagggagccactctgaagatcaccctggacaacgcttacatggagaagtgtgacgagaacatcctgtggctgga
ctacaagaacatctgcaaggtggtggaggtgggcagcaagatctacgtggacgatgggctcatctcactgcaggtgaag
gagaaaggcgctgacttcctggtgacggaggtggagaatggtggctccttgggcagcaagaagggcgtgaacctgccg
ggcgctgctgtggatctcccgctgtgtcggaaaaggacatccaggacctgaagtttggggtggagcaggatgtggacat
ggtgtttgcatctttcatccgcaaggcagccgacgtgcatgaagtcaggaaggtgctgggagagaagggcaagaacatc
aagatcatcagcaaaatcgagaaccatgaaggcgtccgcaggtttgatgagatcttggaggccagtgatgggatcatgg
tggctcgtggtgacctgggcattggagattcctgcagagaagtcttcctggctcagaagatgatgatcgggcgatgcaacc
gagctgggaagcctgtcatctgtgccacacagatgctggagagcatgatcaagaagccacgccccaccgtgctgaag
gcagtgatgtggccaatgcagtcctggatggagcagactgcatcatgctgtctggagaaacagccaaggggactacc
ctctggaggctgttcgcatgcagcacctgattgcccgagaggcagaggctgccatctaccatttgcagctattcgaggaa
ctccgccgcctggcgcccattaccagcgacccccacagaagctgccgccgtgggtgccgtggaggcctccttcaagtgct
gcagtgggccattatcgtgctcaccaagtctggcaggagtgctccaccaagtggccaggtaccgccctcgggctcctatc
attgccgtgactcgaaatccccagactgctcgccaggcccatctgtaccgtggcatcttccctgtgctgtgtaaggatgccgt
gctgaatgcctgggctgaggatgtcgaccttcgtgtaaacttggccatggatgttggcaaggcccgaggcttcttcaagaa
gggagatgtggtcattgtgctgaccgggtggcgccctggctctggattcaacaaccatgcgtgtagtgcctgtaccttga
```
<ins>GCTGCCTTCTGCGGGGCTTGCCTTCTGGCCATGCCCTTCTTCTCTCCCTTGCACCT</ins>
<ins>GTACCTCTTGGTCTTTGAATAAAGCCTGAGTAGGAA</ins> (SEQ ID NO: 6)

7 nucGFP-K motif
TTGGACCCTCGTACAGAAGCTAATACGACTCACTATAGGGAAAGGTGGGCGTGAT
CCGAAAGGTGACCCGGATCTGGGGCGTGATCCGAAAGGTGACCCGGAAAGCCAC
```
Catggtgagcaagggcgaggagctgttcaccggggtggtgcccatcctggtcgagctggacggcgacgtaaacggcc
acaagttcagcgtgtccggcgagggcgagggcgatgccacctacggcaagctgaccctgaagttcatctgcaccaccg
gcaagctgcccgtgccctggcccaccctcgtgaccaccctgacctacggcgtgcagtgcttcagccgctaccccgacca
catgaagcagcacgacttcttcaagtccgccatgcccgaaggctacgtccaggagcgcaccatcttcttcaaggacgac
ggcaactacaagacccgcgccgaggtgaagttcgagggcgacaccctggtgaaccgcatcgagctgaagggcatcg
acttcaaggaggacggcaacatcctggggcacaagctggagtacaactacaacagccacaacgtctatatcatggccg
acaagcagaagaacggcatcaaggtgaacttcaagatccgccacaacatcgaggacggcagcgtgcagctcgccga
ccactaccagcagaacacccccatcggcgacggccccgtgctgctgcccgacaaccactacctgagcacccagtccg
ccctgagcaaagaccccaacgagaagcgcgatcacatggtcctgctggagttcgtgaccgccgccgggatcactctcg
gcatggacgagctgtacaaggagatccaaaaaagaagagaaaggtaggcgatccaaaaaagaagagaaaggta
ggtgatccaaaaaagaagagaaaggtataa
```
<ins>GCTGCCTTCTGCGGGGCTTGCCTTCTGGCCATG</ins>
<ins>CCCTTCTTCTCTCCCTTGCACCTGTACCTCT</ins>TGGTCTTTGAATAAAGCCTGAGTAG
GAA (SEQ ID NO: 7)

8 ihCD25 K motif-non modified
TTGGACCCTCGTACAGAAGCTAATACGACTCACTATAGGGAAAGGTGGGCGTGAT
CCGAAAGGTGACCCGGATCTGGGGCGTGATCCGAAAGGTGACCCGGAAAGCCAC
```
Catggattcatacctgctgatgtggggactgctcacgttcatcatggtgcctggctgccaggcagagctctgtgacgatgac
ccgccagagatcccacacgccacattcaaagccatggcctacaaggaaggaaccatgttgaactgtgaatgcaagag
aggtttccgcagaataaaaagcgggtcactctatatgctctgtacaggaaactctagccactcgtcctgggacaaccaatg
tcaatgcacaagctctgccactcggaacacaacgaaacaagtgacacctcaacctgaagaacagaaagaaaggaa
aaccacagaaatgcaaagtccaatgcagccagtggaccaagcgagccttccaggtcactgcagggaacctccaccat
gggaaaatgaagccacagagagaatttatcatttcgtggtggggcagatggtttattatcagtgcgtccagggatacaggg
ctctacacagaggtcctgctgagagcgtctgcaaaatgacccacgggaagacaaggtggaccagccccagctcatat
gcacaggtgaaatggagaccagtcagtttccaggtgaagagaagcctcaggcaagccccgaaggccgtcctgagagt
gagacttcctgcctcgtcacaacaacagattttcaaatacagacagaaatggctgcaaccatggagacgtccatatttaca
acagatctccaggtagcagtggccggctgtgttttcctgctgatcagcgtcctcctcctgagtgggctcacctggcagcgga
gacagaggaagagtagaagaacaatctag
```
<ins>GCTGCCTTCTGCGGGGCTTGCCTTCTGGCCATG</ins>
<ins>CCCTTCTTCTCTCCCTTGCACCTGTACCTCTTGGTCTTTGAATAAAGCCTGAGTAG</ins>
<ins>GAA</ins> (SEQ ID NO: 8)

SEQ ID NO:
5' UTR
Open Reading Frame (ORF)
3' UTR ihCD25 modRNA-Based CM-Specific Cell Sorting

To test whether our novel CMs-specific modRNA-based design that allows a transient gene expression of our genes of interest exclusively in CMs can be used to isolate only transfected CMs with innovative inactive (only extracellular domain) human CD25 (ihCD25)-based sorting (magnetic beads) system we injected nGFP k-motif with ihCD25 k-motif modRNA in heart after MI, cells were Isolated and sorted out with CD25-specific magnetic beads. Both nGFP-positive CM's and non-CM's were observed. When nGFP k-motif, ihCD25 k-motif with L7AE miR1-miR208 were co-transfected and without magnetic separation, CM specific nGFP expression was seen. The culture also contains nGFP-negative CMs and non-CMs. When magnetic separation was applied, only pure nGFP-positive CMs were observed (FIG. 9).

In one embodiment, production of exogenous genes is driven by expression of anti-miRs from a first replicon that also encodes a repressor protein. Expressed anti-miRs bind miRs that occur naturally in human and primate cardiomyocytes and transcription of the repressor protein is prevented. In the absence of repressor protein, expression of a gene of interest from a second replicon encoding the gene and containing the repressor protein recognition site can proceed.

Cell Cycle Inducer Genes

Expression of a gene of interest, for example, a proliferation-inducing gene can be made cardiomyocyte-specific by placing transcription/translation of the gene under the control of a transcription/translational regulatory system in which one of a pair of nucleic acids encodes an antimicroRNA (anti-miR) that binds specifically to a target cardiomyocyte-specific miR. A second nucleic acid translation suppressor protein and a second nucleic acid that comprises a suppressor protein interaction motif that binds the translation suppressor protein and a gene that encodes a protein of interest.

Using the method described herein, the expression is transient, avoiding the problems associated with unlimited expression, such as hypertrophy.

Repressor/suppressor protein that binds a specific RNA motif inserted in the 5'-untranslated region of an mRNA modulates the translation of that message in mammalian cells. The expression specificity to human and primate cardiomyocytes is achieved by the inclusion in the repressor/suppressor oligonucleotide of a sequence that encodes a recognition element specific to endogenous miRNAs found in mouse, pig, human and non-human primate cardiomyocytes.

The synthesis of modRNA for in vivo use involves four stages: DNA template creation containing the desired transcript, in vitro transcription (IVT), 5' phosphate removal with Antarctic phosphatase, and precipitation with 5M ammonium acetate salt. Investigation into the use of modRNA for experimental and clinical purposes is growing rapidly. Daily transfection with modRNA encoding reprograming factors OCT4, SOX2, MYC, and KLF4 were successful at reprogramming human fibroblasts back to pluripotency (5,8). Additionally, modRNA has been shown to be capable of directing cell fate in vitro by using MyoD modRNA that resulted in the conversion of fibroblasts to skeletal muscle cells (2). ModRNA has also shown promise in directing cell fate in vivo. The expanding use of modRNA technology in vivo and its potential use in the field of cardiac gene therapy motivated us to generate a step-wise, streamlined protocol for the effective synthesis of modRNA for in vivo use.

Cardiomyocytes

In one embodiment, the present disclosure relates to a method of treating a subject following myocardial infarction (MI) or heart failure (HF) in a subject comprising administering an effective amount of a composition comprising at least two synthetic modRNAs to a subject in need thereof.

Protein expression lasts for from 5 to 20 days, in some embodiments from 7 to 14 days, and results in a low immunological response as compared to non-modified RNA.

Inter alia, the present disclosure describes a new set of candidate cell cycle inducer genes: Lin28, Pkm2, and Cyclin D2, which when delivered as modRNA, can reactivate mammalian cardiomyocyte (CM) proliferation in vivo (without increasing CM size or nuclei number), reduce CM apoptosis and increase overall left ventricle vascularization post myocardial infarction (MI). When expression of the cell cycle inducer genes is placed under the control of a transcriptional/translational regulatory (an expression regulatory) system for cardiomyocyte-specific transcription (expression), the result is a tool for cardiomyocyte specific expression of the cell cycle inducer gene-driven proliferation following injury, for example, as the result of myocardial infarction (MI) or heart failure (HF).

Modified mRNA (modRNA) is a safe, efficient, transient, and non-immunogenic gene delivery system that allows one to investigate the effect of cell cycle inducer genes on CMs following MI or HF. Kariko et al. discovered that the substitution of uridine and cytidine with pseudouridine and 5-methylcytidine, respectively, drastically reduced the immune response elicited from exogenous RNA (11,12). Investigation into the mechanism revealed that the nucleoside substitutions resulted in a conformational change in the RNA that caused reduced response by toll-like receptors 3, 7, and 8 (TLR3, TLR7, TLR 8), and retinoic acid-inducible gene 1 (RIG-1) (13). A further decrease in RIG-1 response from modRNA was seen upon removal of the 5' triphosphates (4,10). In order to increase stability and translational efficiency, a 3'-O-Me-m7G(5')ppp(5')G Anti Reverse Cap Analog (ARCA) cap is substituted at the 5' end of the RNA molecule (4,5,10).

Cell Selection by Anti-hCD25 Affinity

Cell selection of cardiomyocytes by traditional FACS cell sorting can be problematic due to the size of the cells. An alternative approach to cell selection was devised. In one embodiment, using the transcription regulatory system of the disclosure, a nucleic acid that encodes the hCD25 extracellular domain (ECD) is included in the construct that contains the nucleic acid that encodes the gene of interest. To isolate CMs that transiently express either control or candidate gene modRNA, cells that co-express the hCD25 ECD plus the gene of interest are selected using an anti-CD25 ECD antibody in an affinity chromatography column or using a panning method. These cells are used to generate gene expression profiles using RNA-seq technique, and identify differentially expressed genes

EXAMPLES

Example 1: Materials

The following materials are used in conjunction with the disclosed method.

All solutions should be made in Nuclease Free water unless otherwise specified. All materials used in this protocol should be nuclease free.

Equipment used includes the following:
1. PCR thermocycler
2. Microfuge
3. Vortex mixer
4. Thermomixer(EPPENDORF™)
5. Nano-Drop
6. Nuclease-free water
7. 15 ml Nuclease Free conical tubes
8. Nuclease free strip PCR tubes
9. Ethanol (100% and 70%)
10. 2 ml Ambion Elution Tubes Primers used for tail PCR are as follows:

Forward Primer:
(SEQ ID NO: 9)
5'-TTG GAC CCT CGT ACA GAA GCT AAT ACG-3'

Reverse Primer:
(SEQ ID NO: 10)
5'-TTT TTT TTT TTT TTT TTT TTT TTT TTT TTT TTT TTT TTT TTT TTT TTT TTT TTT TTT TTT TTT TTT TTT TTT TTT TTT TTT TTT TTT TTT TTT TCT TCC TAC TCA GGC TTT ATT CAA AGA CCA-3'

Construction of DNA template for in vitro transcription using pTEMPLZ plasmid is as follows:
1. T4 Polynucleotide kinase enzyme
2. 100 mM ATP
3. 2× KAPA HiFi HotStart ReadyMix PCR master mix 4. AleI enzyme
5. AfeI enzyme
6. Antarctic phosphatase enzyme
7. T4 DNA ligase enzyme
8. One Shot® ccdB Survival™ 2 T1 Phage-Resistant (T1R) cells
9. QIAquick® gel extraction kit
10. QIAquick® PCR purification kit
11. One shot chemically competent E. coli
12. QIAprep® spin Miniprep kit
13. 10× Phosphorylation Buffer Synthesis of Linear DNA Template with a Poly T Tail for IVT Reaction
1. 2× KAPA HiFi HotStart ReadyMix PCR master mix
2. Primer Solution: 1 µM each of forward and reverse primer
3. DpnI enzyme
4. QIAquick® PCR purification kit In Vitro Transcription Reaction
1. Ambion T7 Megascript® Kit (life technologies Cat #: am1334-5)
2. GTP 75 mM solution (provided in Megascript® kit)
3. ATP 75 mM solution (provided in Megascript® kit)
4. CTP 75 mM solution (provided in Megascript® kit)
5. 5-Methylpseudouridine-5'-Triphosphate (Trilink)
6. Trilink Biotechnologies Anti Reverse Cap Analog, 3'-O-Me-m7G(5')ppp(5')G 10 µmoles (Cat #: N-7003)
7. T7 TURBO DNase enzyme (provided in Megascript® kit)
8. Ambion MEGAclear™ Transcription Clean-Up kit. (life technologies; cat #: AM1908).

RNA Phosphatase Treatment
1. Antarctic phosphatase enzyme

RNA Precipitation
1. 5M Ammonium Acetate Salt solution (Provided in AmbionMEGAclear™ Kit)
2. Elution Buffer (Provided in AmbionMEGAclear™ Kit)

Preparation for modRNA Injection
1. Lipofectamine® RNAiMAXtransfection reagent (Thermofisher Cat #: 13778150)
2. OptiMEM Reduced Serum Medium, no phenol red
3. Ultra-Fine insulin syringe needle 31 g 8 mm Methods The following methods are used in conjunction with the disclosed method. All procedures were carried out at room temperature, in a non-sterile environment unless otherwise specified. All materials used should be nuclease free.

Synthesis of modRNA

ModRNAs were transcribed in vitro from a plasmid templates using a custom ribonucleotide blend of anti-reverse cap analog, 3'-O-Me-m7G(5')ppp(5')G (6 mM, Tri-Link Biotechnologies), guanosine triphosphate (1.5 mM, Life Technology), adenosine triphosphate (7.5 mM, Life Technology), cytidine triphosphate (7.5 mM, Life Technology) and N1-Methylpseudouridine-5'-Triphosphate (7.5 mM, TriLink Biotechnologies) as described previously.[48-50] mRNA was purified using megaclear kit (Life Technology) and was treated with antarctic phosphatase (New England Biolabs), followed by re-purification using Megaclear kit. mRNA was quantitated by Nanodrop (Thermo Scientific), precipitated with ethanol and ammonium acetate, and resuspended in 10 mM TrisHCl, 1 mM EDTA. For a detailed protocol please see our recent publication.[48] modRNA transfection. In vivo transfection of modRNA was done using sucrose citrate buffer containing 20 µl of sucrose in nuclease-free water (0.3 g/ml), 20 µl of citrate (0.1M pH=7; Sigma) mixed with 20 µl of different concentrations of modRNA in saline to a total volume of 60 µl. The transfection mixture was directly injected (3 individual injections, 20 µl each) into the myocardium. For in vitro transfection, we used RNAiMAX transfection reagent (Life Technologies) that was used according to manufacturer's recommendation.

Construction of DNA Template for In Vitro Transcription Using pTEMPLZ Plasmid Carrying k Motif.

pTEMPLZ is a cloning vector into which an ORF of interest can be inserted between the UTR's (FIG. 1). The 5'- and 3'-UTRs are synthesized de novo by synthetic oligos. The synthesized UTR's are annealed together and amplified using forward and reverse primers. To provide an entry site for the ORF, AleI and AfeI restriction sites are introduced in between 5' and 3' UTRs. (The adenine nucleotide (A) of the $1^{st}$ codon (ATG) can be omitted from forward primer sequence as it is provided by the AleI site.) The PCR-amplified fragment and pZErO-2 vector with ampicillin resistance are digested with HindIII and NotI, and ligated together to create pTEMPLZ. (pTEMPLZ plasmid and derivatives should be propagated in bacterial strain resistant to the ccdB gene product such as One Shot® ccdB Survival™ 2 T1 Phage-Resistant (T1R) cells.)

Before insertion into pTEMPLZ, the ORF is amplified by using phosphorylated forward and reverse primer pair for the gene of interest. Phosphorylation of the primers is done using the T4 polynucleotide kinase enzyme according to reaction below:

| | |
|---|---|
| 10× Phosphorylation Buffer | 5 µl |
| Forward primer (100 µM) | 3 µl |
| Reverse Primer (100 µM) | 3 µl |
| 100 mM ATP | 0.5 µl |
| T4 polynucleotide kinase | 10 U |
| Nuclease free Water | 50 µl |

Incubate reaction at 37° C. for 1 hour.

To inactivate enzyme, the reaction is incubated at 65° C. for 20 min. The reaction is diluted to 300 µl by adding 250 µl of water giving final 1 µM primer mixture.

Amplification of the ORF of interest is done using the PCR reaction below:

| | |
|---|---|
| Primer mix (1 µM) from above | 10 µl |
| Template DNA | 1-100 ng |
| Water | 50 µl |
| HiFi HotStart ready mix (2×) | 25 µl |

The mixture is run in Thermocycler with settings according to FIG. 2. The amplified target is isolated using QIAquick gel extraction kit. Before insertion of ORF, pTEMPlz is linearized and dephosphorylated. To linearize plasmid, pTEMPlz is digested with AleI and AfeI according to the reaction below:

| | |
|---|---|
| pTEMPLZ Plasmid DNA | 2 µg |
| Nuclease Free Water | 30 µl |
| 10× Buffer 4 | 3 µl |
| AleI | 5 U |
| AfeI | 5 U |

Incubate in thermomixer for 1 hour at 37° C. Digest was purified using QIAquick® PCR purification kit and eluted in 30 µl of elution buffer.

Linearized pTEMPLZ is dephosphorylated according to reaction below:

| | |
|---|---|
| Linearized plasmid from step 1 | 30 µl |
| 10× antarctic phosphatase buffer | 5 µl |
| Antarctic phosphatase | 5 U |
| Nuclease Free Water | 50 µl |

The reaction is incubated at 37° C. for 1 hour. Enzyme is inactivated by incubating at 65° C. for 15 min.

Linearized and dephosphorylated plasmid is isolated using QIAquick® gel extraction kit and the quantity of pTEMPLZ product is determined using nanodrop. Plasmid can be stored in −20° C. for future use.

Blunt end ligation of ORF of interest is performed into pTEMPLZ according to the reaction below:

| | |
|---|---|
| Linearized dephosphorylated TEMPlz plasmid | 50 ng |
| Amplified ORF | 3-fold molar excess |
| 10× T4 DNA ligase buffer | 2 µl |
| T4 DNA ligase | 4 U |
| Nuclease Free Water | 20 µl |

Mix reagents and incubate overnight on melting ice at room temp or at 16° C. Negative control ligation reaction might be necessary to monitor self-ligation of plasmid. Transformation of plasmid is performed with competent cells and grow on an ampicillin agar plate.

To isolate positive clones with the correct orientation colony PCR is performed. Between 8-10 colonies are extracted from ampicillin agar plates with a pipette tip. Individual tips are stabbed in 200 µl of Luria Broth (LB) and rinsed several times in 75 µl of TE buffer under pH 8.0, tips are incubated in 37° C. in a shaker. Tubes are then boiled for 5 min to lyse bacteria and spun to pellet debris. Colony PCR is performed with 2 µl of supernatant using forward primer and gene specific reverse primer. PCR sample is run on 1% agarose gel to identify clones with positive orientation. 200 µl of LB is cultured with correct orientation clones in larger volume of LB overnight in a 37° C. shaker and extracted using QIAprep® spin Miniprep kit. The quantity of plasmid product is determined using NANODROP™ (Thermo Fisher Scientific) and diluted to a concentration between 1-5 ng/ul.

Synthesis of Tailed DNA Template

A 1600 µl PCR master solution was prepared according to the reaction below:

| | |
|---|---|
| Plasmid solution (1-5 ng/µl) (see Note 3) | 400 µl |
| Primer solution (1 µM primers) | 400 µl |
| 2× KAPA HiFi HotStart ReadyMix. | 800 µl |

50 µl of PCR master solution was aliquoted into 32 separate PCR tubes. PCR is run using the thermo cycler (setting listed in FIG. 2). The length of elongation step may vary depending on DNA polymerase used and ORF length (If using 2× KAPA HiFi HotStart ReadyMix, for example, elongation step of Thermocycler should be set at a ratio of 30 sec per Kb of ORF length).

To digest methylated plasmid DNA, product is combined into one EPPENDORF™ tube and digested with 30 µl of Dpnl. The PCR product is purified using QIAquick PCR Purification Kit (Qiagen cat #: 28106) and the final product eluted in nuclease free water. The concentration of tailed product is measured using nanodrop machine and concentration is adjusted using nuclease free water to 100-200 ng/µl.

For quality control analysis, purity of Tailed DNA template product is checked on a 1% agarose gel together with the original DNA plasmid (FIG. 3a).

In Vitro Transcription (IVT) Reaction (1 ml Reaction Volume)

A custom NTP mixture is prepared in one EPPENDORF™ tube according to Table 2. Reagents for IVT reaction are mixed in the following order into one EPPENDORF™ tube:

a. 400 µl of custom NTP's from table 2.

b. 400 µl of the DNA tailed template (200 ng/µl).

c. Vortex 10× Reaction Buffer from the T7 megascript kit to dissolve any precipitate and add 100 µl.

d. Add 100 µl of T7 Enzyme. This will give you a 1 ml IVT reaction e. Mix thoroughly and Incubate in thermomixer at 37° C. for 4-6 hours. 30 µl of T7 Turbo DNase was added and mixed gently and then incubated at 37° C. in Thermomixer for 15-20 min to halt the reaction (see Note 5).

Purify reaction using Ambion MEGAclear™ Transcription Clean-Up kit and elute each tube three times with 50 µl of 95° C. elution buffer to obtain 150 µl of RNA product in each tube. Combine the RNA mixture from each tube into one EPPENDORF™ tube.

RNA Phosphatase Treatment

Nuclease-free water is added to the RNA to obtain a 1.5 ml solution. 150 µl of Antarctic Phosphatase Buffer (10×) and 150 µl of Antarctic Phosphatase enzyme is added, mixed thoroughly and incubated in thermomixer at 37° C. for 1 hour.

RNA Precipitation Using Ammonium Acetate

The 1800 µl RNA solution is transferred to a 15 ml conical tube. 180 µl of 5M ammonium acetate is added and mixed thoroughly. 5200 µl of cold (−20° C.) 100% ethanol is added to solution and aliquoted into 3-4 2 ml EPPENDORF™ tubes. Let tubes stand in −20° C. overnight. The tubes are centrifuged at 10,000 rpm for 30 min at 4° C. The supernatant is then carefully discarded. Each pellet is dissolved in 500 µl of 70% ethanol. modRNA ethanol solutions from each tube are consolidated into 1 EPPENDORF™ tube. The tube is centrifuged at 10,000 rpm for 30 min at 4° C. The supernatant is gently poured out and discarded, and using a kimwipe, the inside of the tube is gently cleaned. Care is taken not to disturb the pellet. The tube is inverted and let stand for no more than 2 min to air-dry pellet. Using a pipette, any small drops of ethanol left around the pellet are gently removed. The pellet is resuspended using 45-50 µl of elution buffer. modRNA is left in elution buffer for 5 min then gently pipetted until the pellet is dissolved. RNA solution can now be used in vivo, stored in −20° C. for up to 6 months, or −80° C. for 5 years.

ModRNA Yield

Figure 3B:
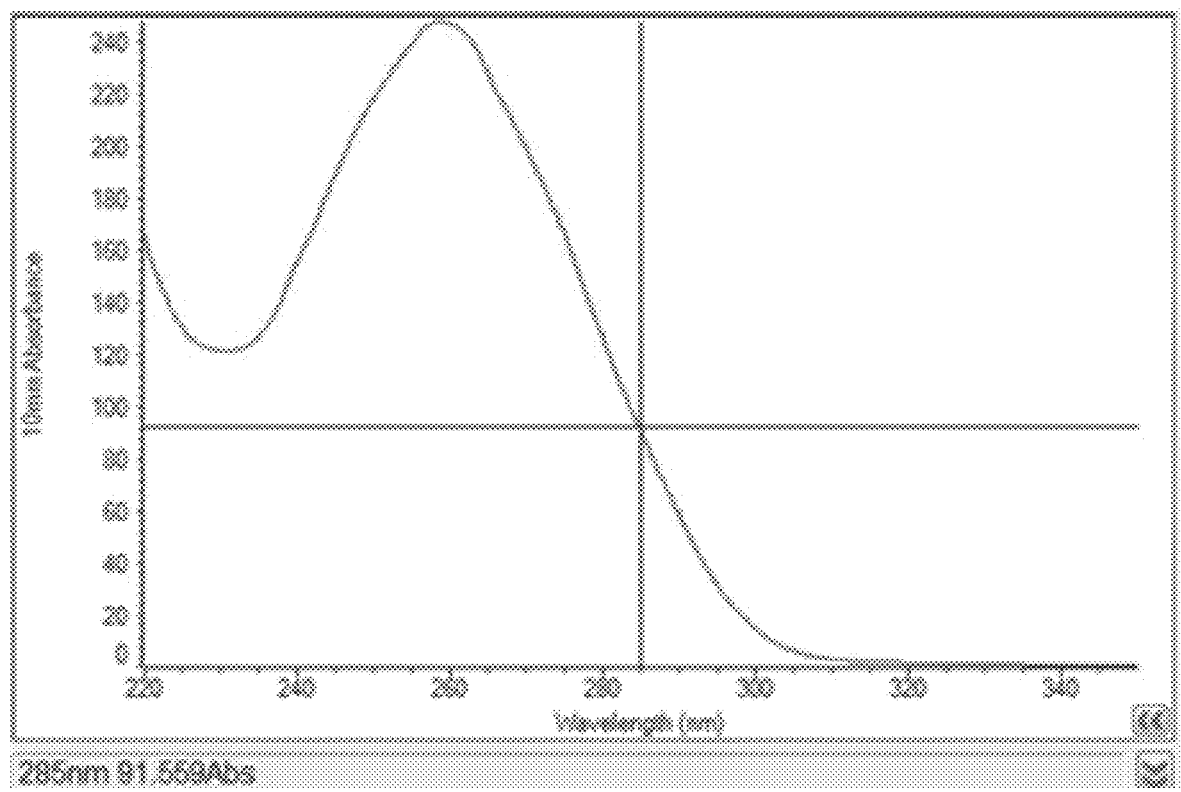
Figure 3C:
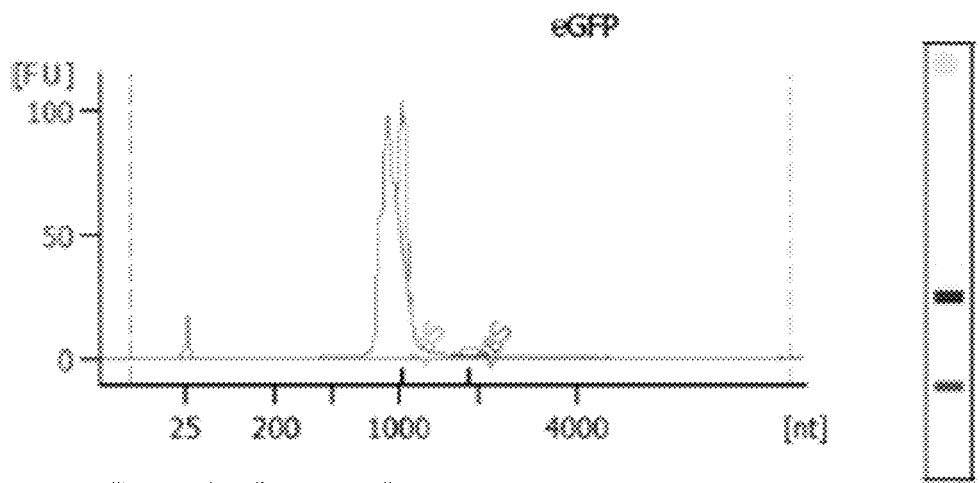
Figure 4A:
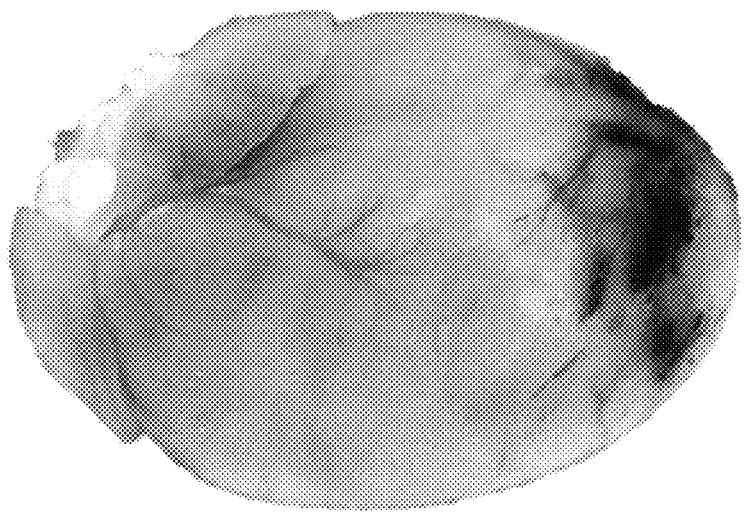
FIGS. 4A-4C A Whole heart view of mouse heart injected in vivo with modRNA encoded with LacZ gene. 24 hours after injection, mouse was sacrificed, the heart was fixed with 4% PFA, and stained with x-gal. B immunostaining of mouse heart injected in vivo with modRNA encoded with nuclear GFP. (left) Cardiomyocytes (TropT: Red), Endothelial cells (Pecam1: Red) and smooth muscle cells (smMHC: Red) positive for nuclear GFP (Green). (DAPI: Blue). C cross section of Rosa26 LacZ mouse heart injected with modRNA encoded with Cre Recombinase. Transfected cells with Cre Recombinase can be stained with x-gal resulting in dark blue color.
Figure 4B:
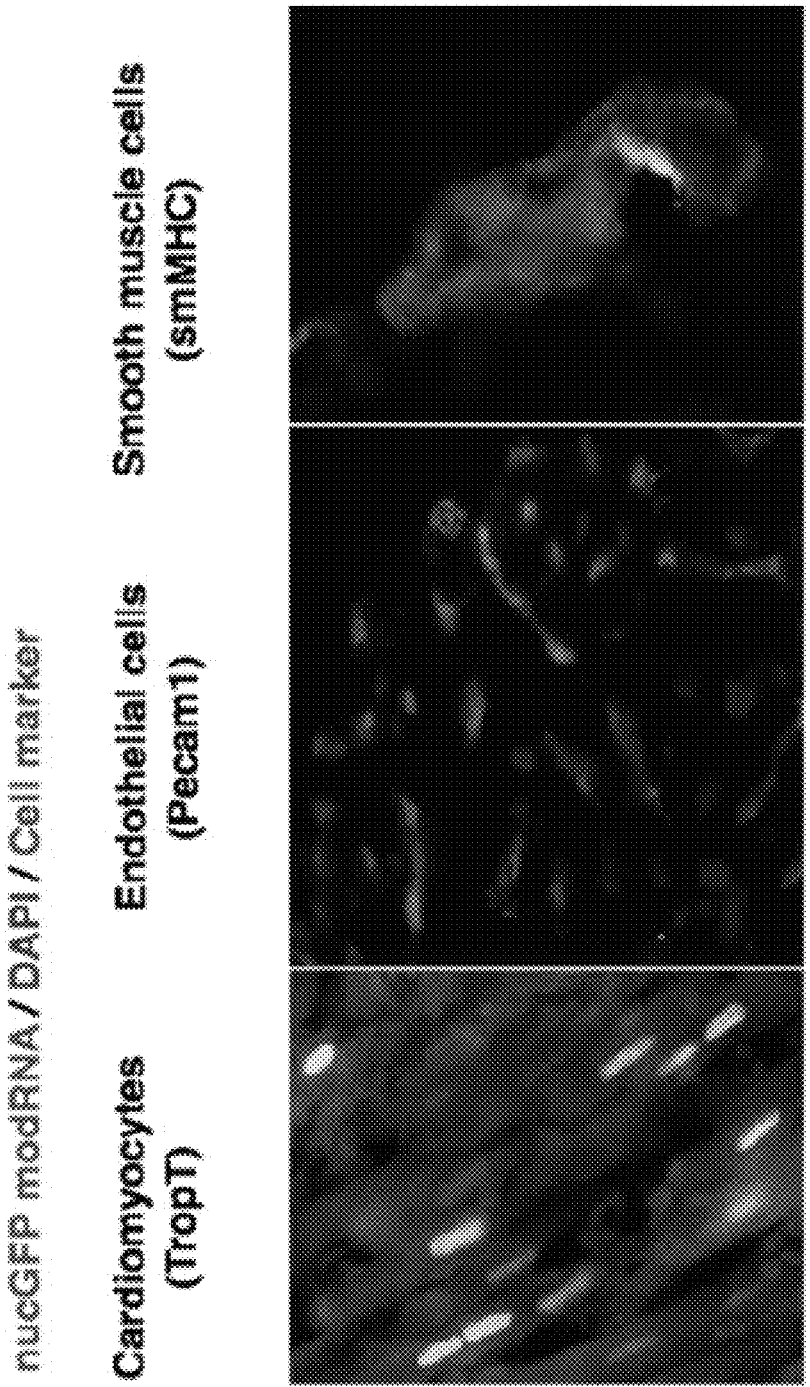
Figure 4C:
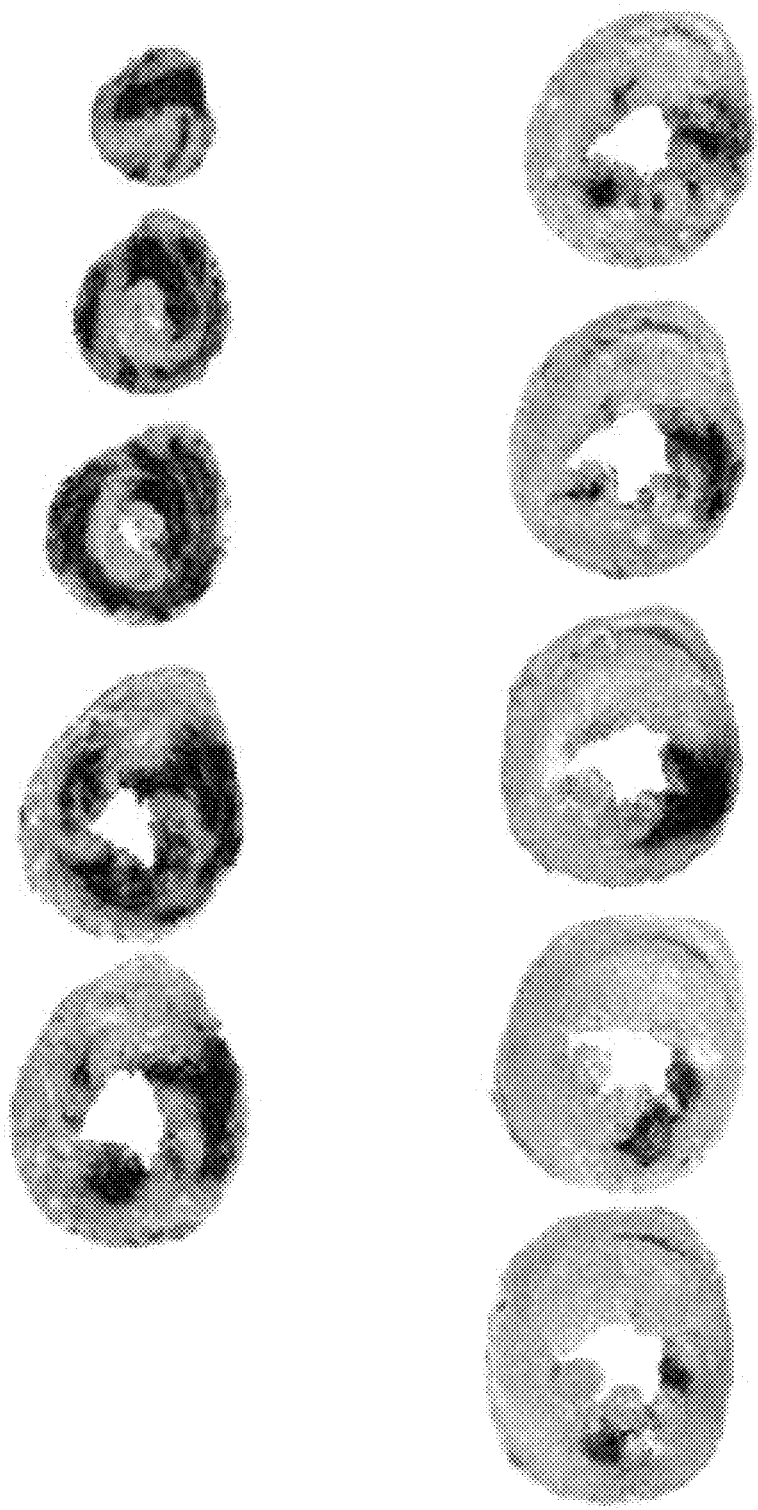

Concentration is measured using nanodrop machine (FIG. 3b). The ratio of A260/A280 should be greater than 1.8 with values closer to 2.0 indicating higher purity. Depending on yield, concentration should be close to 20 µg/ul. For better quality control analysis a 1 µl sample from the final modRNA solution is diluted in 100 µl of nuclease free water. The sample is analyzed using a bioanalyzer machine (FIG. 3c).

Preparation of modRNA for Myocardial Injection in Mice

40 µl of RNAiMax is combined with 5 µl of OptiMEM in an EPPENDORF™ tube and vortexed. The mixture is allowed to sit for 10 min at room temperature. In another EPPENDORF™ tube 150-200 ug of modRNA is combined with 5 µl of OptiMEM. The tube is spun down to eliminate liquid on the sides of the tube. After letting the RNAiMAX and OptiMEM mixture sit for 10 min at room temperature, the liquid from the tube with the modRNA mixture is added to the tube with the RNAiMAX mixture. (In some embodiments, it is important to add the modRNA mixture to the RNAiMAX mixture and not the other way around.) The combined mixture is allowed to stand for 15 min at room temperature. The mixture is extracted into a 31 gauge insulin syringe and injected into mouse myocardium. (Example of result shown in FIG. 4).

Mice

All animal procedures were performed under protocols approved by the Icahn School of Medicine at Mount Sinai Institutional Care and Use Committee. CFW (Swiss Webster) mice or Rosa26$^{mTmG}$ mice, male and female, were used. ModRNAs are synthesized by in vitro transcription as described above. Modified nucleotides (Trident) are pseudouridine, 5-methyl-cytidine, and cap analog. A total of 100-200 µg modified RNA complexed with RNAiMax transfection reagent is injected into the peri-infarct region of the myocardium in an open chest surgery post induction of MI. MRI is performed under light anesthesia (titrated to heart rate and sedation level). LAD ligation and histological analysis is performed as described previously (46). Three to eight animals used for each experiment. For long-term survival, CFW (8-10-week-old) treated with CM-specific Luc or Pkm2 modRNAs (n=10) post induction of MI, and were left to recover for 6 months in the animal facility. Deaths were monitored and documented over time.

Isolation of Cells from Adult Mice Heart

Hearts are excised and perfused using the Langendorff technique, the cells are processed further by using CD25 specific magnetic beads (dynabeads CD25, Thermo Fisher Scientific) and RNA is isolated from cells using a RNeasy mini kit (Qiagen). The RNA is further used for RNA-seq and RT-PCR analysis.

Adult Mouse Myocardial Infarction and Heart Failure Models

The MI model described in FIG. 5 was used to test the therapeutic effect after treatments with CMs-specific Lin28, Pkm2 in CFW or Rosa26$^{CD25}$ mice. The experimental design includes 4 control groups treated with a) vehicle only, b) 100 µg/heart Luc carrying a K-motif modRNA, c) 100 µg/heart L7AE modRNA that carry both miR-1 and miR-208 recognition elements (L7AE miR1+miR208) and d) Luc CMs specific modRNA contain a mixture of Luc carrying a K-motif modRNA and L7AE miR1+miR208, 100 µg/heart from each modRNA (total 200 µg/heart). Controls groups will serve to assess any unspecific effect of reduction of miR-1 and miR-208 in the heart that is not directly related to cell cycle inducer CMs-specific modRNAs. Applicants compared the control groups with 4 experimental groups using 100 µg/heart of a) Lin28 and b) Pkm2, carrying a K-motif modRNA and mixture of d) Lin28, and e) Pkm2, carrying a K-motif modRNA with L7AE miR1+miR208 (cell cycle inducer CMs specific modRNA, 100 µg/heart from each modRNA with (total modRNA 200 pg/heart). We will analyze improved cardiac function after 28 days post MI using MRI and reduced scar formation, and increased capillary density into higher rates of long term survival in comparison to control modRNA. We will also use the Rosa26Tdtomato mice for lineage tracing model of the transfected CMs in MI model. Our experimental design includes 1 control group treated with CMs-specific Luc (50 pg/heart) and DD-Cre (50 pg/heart) mixed together with 100 pg/heart L7AE miR1+miR208. We will compare the control groups with 3 experimental groups treated with CMs-specific cell cycle inducer modRNAs. We will use a mixture containing DD-Cre (50 pg/heart) and cell cycle inducer gene (Lin28 and Pkm2 50 pg/heart) carrying a K-motif modRNA mixed together with 100 pg/heart of L7AE miR-1+miR-208 (total modRNA 200 pg/heart). The heart of Rosa26$^{Tdtomto}$ mice, will be directed intramuscular injected with total of 100 or 200 pg modRNA. Using CMs lineage tracing model we will test 28 days post injection transfect CMs size using CMs cross-section area evaluation with anti wheat germ agglutinin (WGA) antibody in immunofluorescence analysis. We will count the number of transfected CMs per left ventricle and evaluate the number of nuclei per CMs in each of the treatments. These testing using Rosa26$^{Tdtomato}$ mice will allow us to evaluate the changes in CMs function after different treatments with CMs specific modRNAs over time.

The MI model described in FIG. 5 was also used for testing gene expression changes in transfected CMs and non-transfected cells of the left ventricle. Our experimental design includes 3 control groups treated with different CMs-specific Luc (50 µg/heart) and inactivate (only extracellular domain) human CD25 (ihCD25, see FIGS. 1 and 8, 50 µg/heart) mixed together with 100 µg/heart L7AE miR1+miR208 (total modRNA 200 µg/heart). Control groups are compared with 3 experimental groups treated with CMs-specific cell cycle inducer modRNAs. Applicants used a mixture containing ihCD25, (50 µg/heart) and cell cycle inducer gene (Lin28 and Pkm2, 50 µg/heart) carrying a K-motif modRNA mixed together with 100 pg/heart of L7AE miR-1+miR-208 (total modRNA 200 µg/heart). Three days' post treatment with 200 µg CMs-specific of different Luc controls or cell cycle inducer, Lin28 or Pkm2 in CFW mice (n=10), mice will be sacrificed and hearts will be dissociated with collagenase. Transfected CMs will be isolated from cardiac cell suspension using our CMs-specific modRNA sorting approach. This sorting approach is based on the use of CMs-specific modRNA ihCD25 and commercially available anti hCD25 magnetic beads (Thermo Fisher). Magnetic beads isolation is been used for variety of application, including cell sorting, for over 30 years. The magnetic beads that been used for cell sorting are pre-coupled with antibody that can recognize cell surface gene. As transfected CMs usually don't carry a specific cell surface genes, we use the truncated hCD25 to mark the transfected CMs and allow anti hCD25 magnetic beads to recognize and to attach exclusively to transfected CMs. Using a magnet and elution of residual beads and un-transfected cells will result in pure isolated transfected CMs cell population. Immediately after isolation RNA is extracted from the sorted transfected CMs and from the eluted fraction of cells (non-transfected cells) and sent for RNA-seq using HIseq2500 system in the Mount Sinai Genomics Core Facility. Some RNA is used for validation of RNA-seq measurements using Quantitative reverse transcription polymerase chain reaction (qRT-PCR). Downstream targets selection is based on: a) differentially expressed genes in control Luc vs. modRNA specifically in CMs; b) overlapping candidates between the different cell cycle inducer modRNAs treatments; c) Differentially expressed genes in CMs that may influence the gene expression observed in non-transfected cells. For example, up regulation of a relevant receptor in the non-transfected population indicates the secretion of its ligand from CMs. d) data mining of the literature. 3-5 targets are selected for validation using above approach. To test the hypothesis, we injected with CMs-specific nGFP k motif, inactivate (only extracellular domain) human CD25 (ihCD25) mixed together with L7AE miR1-miR208 after MI and we successfully sorted out nGFP and ihCD25 expressing CMs after 24 hrs post injection FIG. 19.

Magnetic Resonance Imaging (MRI) and Echocardiography (Echo).

CFW mice (8-weeks old) treated with Luc k motif, Luc k motif+miR1-208, miR1-208, Pkm2 k motif and Pkm2 k motif+miR1-208 modRNA were subjected to MRI assessment on day 28 post LAD ligation.[11] We obtained delayed-enhancement CINE images on a 7-T Bruker Pharmascan with cardiac and respiratory gating (SA Instruments, Inc, Stony Brook, N.Y.). Mice were anesthetized with 1-2% isoflurane/air mixture. ECG, respiratory, and temperature probes were placed on the mouse, which was kept warm during scans. Imaging was performed 10 to 20 min after IV injection of 0.3 mmol/kg gadolinium-diethylene triamine pentaacetic acid. A stack of eight to ten short-axis slices of the heart spanning the apex to the base were acquired with an ECG-triggered and respiratory-gated FLASH sequence with the following parameters: echo time (TE) 2.7 msec with resolution of 200 µm×200 µm; slice thickness of 1 mm; 16 frames per R-R interval; 4 excitations with flip angle at 60°. Ejection fraction was calculated as the difference in end-diastolic and end-systolic volumes, divided by the end-diastolic volume. MRI acquisition and analyses were performed blinded to treatment groups. For Echo evaluation of left ventricular systolic function a GE cares in site (V7R5049) equipped with a 40 MHz mouse ultrasound probe were used. Fractional shortening was calculated based on end diastolic and end systolic dimensions obtained from M-mode ultrasound. Echocardiograms were performed on 6-8 hearts/treatment groups.

RNA Isolation and Gene Expression Profiling Using Real-Time PCR

Total RNA was isolated using the RNeasy mini kit (Qiagen) and reverse transcribed using Superscript III reverse transcriptase (Invitrogen), according to the manufacturer's instructions. Real-time qPCR analyses were performed on a Mastercycler realplex 4 Sequence Detector (Eppendorf) using SYBR Green (Quantitect™ SYBR Green PCR Kit, Qiagen). Data were normalized to 18s expression, where appropriate (endogenous controls). Fold-changes in gene expression were determined by the ∂∂cT method and were presented relative to an internal control. PCR primer sequences are shown in Supplemental Table 3.

TABLE 3

| Gene | Forward (SEQ ID NO:) | Reverse (SEQ ID NO:) |
|---|---|---|
| Pkm2 | gtctggagaaacagccaagg (11) | cggagttcctcgaatagctg (12) |
| Tnnt2 | ctgagacagaggaggccaac (13) | ttccgctctgtcttctggat (14) |
| Mhy6 | cagaacaccagcctcatcaa (15) | cccagtacctccgaaagtca (16) |
| Pecam1 | ctgccagtccgaaaatggaac (17) | cttcatccaccggggctatc (18) |
| Cdh5 | attgagacagaccccaaacg (19) | ttctggttttctggcagctt (20) |
| αSMA | aagctgcggctagaggtca (21) | ccctcccttttgatggctgag (22) |

TABLE 3-continued

| Gene | Forward (SEQ ID NO:) | Reverse (SEQ ID NO:) |
|---|---|---|
| WT1 | agacacacaggtgtgaaacca (23) | atgagtcctggtgtgggtct (24) |
| Myc | aggcagctctggagtgagag (25) | cctggctcgcagattgtaag (26) |
| Hif1a | gggtacaagaaaccacccat (27) | gaggctgtgtcgactgagaa (28) |
| Pdk1 | accaggacagccaatacaag (29) | cctcggtcactcatcttcac (30) |
| Cdc20 | ttcgtgttcgagagcgatttg (31) | accttggaactagatttgccag (32) |
| Cdk1 | tttcggccttgccagagcgtt (33) | gtggagtagcgagccgagcc (34) |
| Ccnd2 | gtcacccctcacgacttcat (35) | ttccagttgcaatcatcgac (36) |
| Ccnb1 | aaggtgcctgtgtgtgaacc (37) | gtcagcccatcatctgcg (38) |
| 18s | agtccctgccctttgtacaca (39) | cgatccgagggcctcacta (40) |
| HDac4 | aaccttagtggggtgctgtg (41) | aaggcacaaactcgcatctt (42) |
| Hand2 | ccagctacatcgcctacctc (43) | tggttttcttgtcgttgctg (44) |
| Meox2 | cacagtgcctgaaatcacca (45) | ctggctgtgtttgtcaatgg (46) |
| Gata4 | tccagcctgaacatctaccc (47) | ccatagtcaccaaggctgct (48) |
| Mstn | tggctcctactggacctctc (49) | tgccttttaagatgcagcag (50) |
| MYHC | cagaacaccagcctcatcaa (51) | gctccttcttcagctcctca (52) |

Lineage Tracing in R26$^{mTmG}$ Mice

Rosa26$^{mTmG}$ mice were obtained from the Jackson Laboratory. All experiments were performed on age- and sex-matched mice with equal ratio of male and female mice. Healthy mice were chosen randomly from the expansion colony for each experiment. In this mice line, membrane-targeted tdTomato is expressed under the control of ubiquitous promoter on Rosa26 locus, whereas membrane-targeted eGFP becomes active after Cre-mediated excision of floxed tdTomato. CM-specific Cre modRNA (Cre K-motif+miR1-miR208) was used to exclusively express Cre in transfected CMs. This allowed for lineage tracing of the transfected CMs and their progeny long after the modRNA expression was diminished (>10 days). Rosa26$^{mTmG}$ mice were genotyped by PCR with tail DNA as described in the Jackson Laboratory Genotyping Protocols. Primer sequences are as follows: Rosa26mT/mG, wild type forward, 5' CTCTGCTGCCTCCTGGCTTCT-3' (SEQ ID NO: 53), wild type reverse, 5'-CGAGGCGGATCACAAGCAATA-3' (SEQ ID NO:54), and mutant reverse, 5'-TCAATGGGCGGGGGTCGTT-3' (SEQ ID NO: 55). In this model, we measured the transfection level of CM-specific Cre modRNA, CMs size and number, and the number of nuclei in CMs post transfection with CM-specific Luc or Pkm2 modRNAs.

Neonatal Rat and Adult Mouse CMs Isolation

CMs from 3-4 day old neonatal rat's heart were isolated as previously described.[1] Neonatal rats' ventricular CMs were isolated from 4 day-old Sprague Dawley rats (Jackson). We used multiple rounds of digestion with 0.14-mg/mL collagenase II (Invitrogen). After each digestion, the supernatant was collected in Horse serum (Invitrogen). Total cell suspension was centrifuged at 1500 rpm for 5 min. Supernatants were discarded and cells were resuspended in DMEM (GIBCO) medium with 0.1 mM ascorbic acid (Sigma), 0.5% Insulin-Transferrin-Selenium (100×), penicillin (100 U/mL) and streptomycin (100 μg/mL). Cells were plated in plastic culture dishes for 90 min until most of the non-myocytes attached to the dish and myocytes remained in suspension. Myocytes were then seeded at $1 \times 10^5$ cells/well in a 24well plate. Neonatal rat CMs were incubated for 48 hours in DMEM medium containing 5% horse serum plus Ara c. After incubation, cells were transfected with different doses of different modRNAs as described in the text. Adult CMs were isolated from CFW mice after 28 days post MI and modRNA injection using Langendorff's method as previously described.[2] For CMs count, we averaged 3 different counts/sample and 3 hearts/group using a hemocytometer. The total number of CMs counted was approximately 150-200 CMs/aliquot (10 ul aliquots samples using a wide-bore pipette from the total volume of CMs obtained following digestion). The cultured CMs were stained with α-actinin (CMs, Red) antibody (abcam) and Hoechst 33342 for nuclei counts. For nuclei count, approximately $1 \times 10^3$ CMs were counted per sample, using 3-4 independent samples per group. nuclei count was plotted as percentage of counted CMs. For isolation of transfected adult CMs and RNA isolation please see FIGS. 17A-17C.

Mouse MI Model and Histology

All surgical and experimental procedures with mice were performed in accordance with protocols approved by Institutional Animal Care and Use Committees at Icahn School of Medicine at Mount Sinai Institutional Animal Care and Use Committee (IACUC) and the MSSM Center for Comparative Medicine and Surgery (CCMS). CFW, $R26^{mTmG}$ mice (6-8 weeks old) were anesthetized with isoflurane. MI was induced by permanent ligation of the LAD, as previously described[3]. Briefly, the left thoracic region was shaved and sterilized. After intubation, the heart was exposed through a left thoracotomy. A suture was placed to ligate the LAD. The thoracotomy and skin were sutured closed in layers. Excess air was removed from the thoracic cavity, and the mouse was removed from ventilation when normal breathing was established. In order to determine the effect of modRNA on cardiovascular outcome after MI, modRNAs (100-150 μg/heart) were injected into the infarct zone immediately after LAD ligation. The peri-infarct zone near the apex was either snap-frozen for RNA isolation and subsequent real-time qPCR studies, or fixed in 4% PFA for cryo-sectioning and immunostaining. In all experiments, the surgeon was blinded to the treatment group. For assessment of heart histology, hearts were collected at the end of each study. The hearts were excised, briefly washed in PBS, perfused with perfusion buffer, weighted and fixed in 4% PFA at 4° C. overnight. On the next day hearts were washed with PBS and incubated overnight in 30% sucrose. Next, hearts were put in OCT, were frozen and stored at −80° C. The heart blocks were transverse sectioned at 8-9 μm using cryostat. The slides were further processed for evaluation using immunostaining (see below) or histological scar staining using Masson's trichrome staining kit (Sigma) and were performed according to standard procedures. Measuring ratio of heart-weight to body-weight was done using a scale. The ratio was measured at the end point of each experiment. This ratio was calculated as the heart tissue weight relative to the mouse total body-weight in grams (g).

Immunostaining of Heart Sections Following modRNA Treatment

The mouse hearts were harvested and perfused using perfusion buffer and 4% paraformaldehyde (PFA). Hearts were fixed in 4% PFA/PBS overnight on shaker and then washed with PBS for 1 hr and incubated in 30% sucrose/PBS at 4° C. overnight. The next day, hearts were fixed in OCT and frozen at −80° C. Tansverse heart sections (8-10 μM) were made by cryostat. Frozen sections were rehydrated in PBS for 5 min followed by permeabilization with PBS with 0.1% triton X100 (PBST) for 7 min. Slides were then treated with 3% $H_2O_2$ for 5 min. After 3 washes with PBST for 5 minutes each, the samples were blocked with PBS+5% Donkey normal serum+0.1% Triton X100 (PBSST) for 2 hours at room temperature and primary antibodies diluted in PBSST were added. Slides were then incubated overnight at 4° C. Slides were washed with PBST (5 times for 4 minutes each) followed by incubation with a secondary antibody (Invitrogen, 1:200) diluted in PBST for 2 hours at room temperature. The samples were further washed with PBST (3 times for 5 min each) and stained with Hoechst 33342 (1 μg/ml) diluted in PBST for 7 min. After 5 washes with PBST for 4 minutes each, and one time with tap water (for 4 minutes), slides were mounted with mounting medium (VECTASHIELD) for imaging. Stained slides were stored at 4° C. All staining were performed on 3-8 hearts/group, with 2-3 sections/heart. In the case of immunostaining with wheat germ agglutinin (WGA) for CMs size quantification, images at 20× magnification were captured and ImageJ was used to determine the area of each cell. Quantitative analyses involved counting of multiple fields from 3-6 independent hearts per group, and 3 sections/heart (~50 cells per field assessed, to a total ~250 cells per sample). For BrdU immunostaining, BrdU (1 mg/ml, Sigma) was added to the drinking water of adult mice (2-3-month-old) for 7-10 days before harvesting the hearts. Quantitative analyses involved counting BrdU positive CMs in multiple fields from three independent samples per group, and 3 sections/heart. The total number of CMs counted was ~1-2× $10^3$ CMs per section. TUNEL immunostaining, was performed according to manufacturer's recommendations (In-Situ Cell Death Detection Kit, Fluorescein, Cat #11684795910, Roche). For Immunostaining of neonatal CMs following modRNA treatment, modRNA-transfected neonatal CMs were fixed on coverslips with 3.7% PFA for 15 min at room temperature. Following permeabilization with 0.5% Triton X in PBS for 10 min at room temperature, cells were blocked with 5% normal goat/Donkey serum+ 0.5% Tween 20 for 30 minutes. Coverslips were incubated with primary antibodies (see supplemental Table 1) in humid chamber for 1 hour at room temperature followed by incubation with corresponding secondary antibodies conjugated to Alexa Fluor 488, Alexa Fluor 647 and Alexa Fluor 555, and Hoechst 33342 staining for nuclei visualization (all from Invitrogene). The fluorescent images were taken on Zeiss fluorescent microscopy at 10×, 20× and 40× magnification.

Live Cell Imaging of Isolated Rat Neonatal Cardiomyocytes

The time-lapse images of isolated rat neonatal cardiomyocytes post transfection with nGFP CMs specific modRNA or co-transfected with nGFP and CM-specific Pkm2 modRNAs were acquired with a 10× objective lens every 10 sec with a confocal spinning disk microscope (Zeiss) following 24 hours of time-lapse acquisition.

Statistical Analysis

Statistical significance was determined by paired t-test for the MRI results, Log-rank (Mantel-Cox) test for survival curves or Student's t-test or One-way ANOVA, Bonferroni post hoc test for other experiments as detailed in the respective figure legends, with *p<0.05 or lower considered significant. All graphs represent average values, and values were reported as mean±standard error of the mean. Two-sided Student's t-test was based on assumed normal distributions. For the quantification of the number of CD31 luminal structure, WGA, CD45, CD3, TUNEL, BrdU$^+$, ki67$^+$, pH3$^+$ or Aurora B$^+$ CMs, the results acquired from at least 3 heart sections.

TABLE 2

| Nucleotide | Stock concentration (mM)/stock amount (µmoles) | How much to add (µl) | Final concentration (mM) |
| --- | --- | --- | --- |
| ARCA | 10 µmoles | Use entire Trilink vial | 6 |
| GTP | 75 mM | 36 µl from Ambion kit | 1.5 |
| ATP | 75 mM | 183 µl from Ambion kit | 7.5 |
| CTP | 75 mM | 183 µl from Ambion kit | 7.5 |
| 1.1-methyl pseudouridine | 100 mM | 138 µl from Trilink vial | 7.5 |
| Nuclease Free Water | N/A | 205 µl from Ambion kit | — |

REFERENCES

1 Dargie, H. Heart failure post-myocardial infarction: a review of the issues. *Heart* 91 Suppl 2, ii3-6; discussion ii31, ii43-38, doi:10.1136/hrt.2005.062018 (2005).

2 Lin, Z. & Pu, W. T. Strategies for cardiac regeneration and repair. *Science translational medicine* 6, 239rv231, doi: 10.1126/scitranslmed.3006681 (2014).

3 Bader, D. & Oberpriller, J. O. Repair and reorganization of minced cardiac muscle in the adult newt (*Notophthalmus viridescens*). *Journal of morphology* 155, 349-357, doi: 10.1002/jmor.1051550307 (1978).

4 Engel, F. B. Cardiomyocyte proliferation: a platform for mammalian cardiac repair. *Cell cycle* 4, 1360-1363, doi: 10.4161/cc.4.10.2081 (2005).

5 Major, R. J. & Poss, K. D. Zebrafish Heart Regeneration as a Model for Cardiac Tissue Repair. *Drug discovery today. Disease models* 4, 219-225, doi:10.1016/j.ddmod.2007.09.002 (2007).

6 Poss, K. D. Getting to the heart of regeneration in zebrafish. *Seminars in cell & developmental biology* 18, 36-45, doi:10.1016/j.semcdb.2006.11.009 (2007).

7 Poss, K. D., Wilson, L. G. & Keating, M. T. Heart regeneration in zebrafish. *Science* 298, 2188-2190, doi: 10.1126/science.1077857 (2002).

8 Singh, B. N., Koyano-Nakagawa, N., Garry, J. P. & Weaver, C. V. Heart of newt: a recipe for regeneration. *Journal of cardiovascular translational research* 3, 397-409, doi:10.1007/s12265-010-9191-9 (2010).

9 Leone, M., Magadum, A. & Engel, F. B. Cardiomyocyte proliferation in cardiac development and regeneration: a guide to methodologies and interpretations. *American journal of physiology. Heart and circulatory physiology* 309, H1237-1250, doi:10.1152/ajpheart.00559.2015 (2015).

10 Turnbull, I. C. et al. Myocardial Delivery of Lipidoid Nanoparticle Carrying modRNA Induces Rapid and Transient Expression. *Molecular therapy: the journal of the American Society of Gene Therapy* 24, 66-75, doi: 10.1038/mt.2015.193 (2016).

11 Chien, K. R., Zangi, L. & Lui, K. O. Synthetic chemically modified mRNA (modRNA): toward a new technology platform for cardiovascular biology and medicine. *Cold Spring Harbor perspectives in medicine* 5, a014035, doi:10.1101/cshperspect.a014035 (2015).

12 Huang, C. L. et al. Synthetic chemically modified mrna-based delivery of cytoprotective factor promotes early cardiomyocyte survival post-acute myocardial infarction. *Molecular pharmaceutics* 12, 991-996, doi:10.1021/mp5006239 (2015).

13 Kondrat, J., Sultana, N. & Zangi, L. Synthesis of Modified mRNA for Myocardial Delivery. *Methods in molecular biology* 1521, 127-138, doi: 10.1007/978-1-4939-6588-5_8 (2017).

14 Zangi, L. et al. Modified mRNA directs the fate of heart progenitor cells and induces vascular regeneration after myocardial infarction. *Nature biotechnology* 31, 898-907, doi:10.1038/nbt.2682 (2013).

15 Zangi, L. et al. Insulin-Like Growth Factor 1 Receptor-Dependent Pathway Drives Epicardial Adipose Tissue Formation After Myocardial Injury. *Circulation* 135, 59-72, doi:10.1161/CIRCULATIONAHA.116.022064 (2017).

16 Israelsen, W. J. et al. PKM2 isoform-specific deletion reveals a differential requirement for pyruvate kinase in tumor cells. *Cell* 155, 397-409, doi:10.1016/j.cell.2013.09.025 (2013).

17 Zheng, X. et al. Metabolic reprogramming during neuronal differentiation from aerobic glycolysis to neuronal oxidative phosphorylation. *eLife* 5, doi:10.7554/eLife.13374 (2016).

18 Dong, G. et al. PKM2 and cancer: The function of PKM2 beyond glycolysis. *Oncology letters* 11, 1980-1986, doi: 10.3892/ol.2016.4168 (2016).

19 Riganti, C., Gazzano, E., Polimeni, M., Aldieri, E. & Ghigo, D. The pentose phosphate pathway: an antioxidant defense and a crossroad in tumor cell fate. *Free radical biology & medicine* 53, 421-436, doi:10.1016/j.freeradbiomed.2012.05.006 (2012).

20 Luo, W. et al. Pyruvate kinase M2 is a PHD3-stimulated coactivator for hypoxia-inducible factor 1. *Cell* 145, 732-744, doi:10.1016/j.cell.2011.03.054 (2011).

21 Azoitei, N. et al. PKM2 promotes tumor angiogenesis by regulating HIF-1alpha through NF-kappaB activation. *Molecular cancer* 15, 3, doi:10.1186/s12943-015-0490-2 (2016).

22 Heo, J. S. & Lee, J. C. beta-Catenin mediates cyclic strain-stimulated cardiomyogenesis in mouse embryonic stem cells through ROS-dependent and integrin-mediated PI3K/Akt pathways. *Journal of cellular biochemistry* 112, 1880-1889, doi:10.1002/jcb.23108 (2011).

23 Beigi, F. et al. C3orf58, a novel paracrine protein, stimulates cardiomyocyte cell-cycle progression through the PI3K-AKT-CDK7 pathway. *Circulation research* 113, 372-380, doi:10.1161/CIRCRESAHA.113.301075 (2013).

24 Bersell, K., Arab, S., Haring, B. & Kuhn, B. Neuregulinl/ErbB4 signaling induces cardiomyocyte proliferation and repair of heart injury. *Cell* 138, 257-270, doi:10.1016/j.cell.2009.04.060 (2009).

25 D'Uva, G. et al. ERBB2 triggers mammalian heart regeneration by promoting cardiomyocyte dedifferentiation and proliferation. *Nature cell biology* 17, 627-638, doi:10.1038/ncb3149 (2015).

26 Engel, F. B. et al. p38 MAP kinase inhibition enables proliferation of adult mammalian cardiomyocytes. *Genes & development* 19, 1175-1187, doi:10.1101/gad.1306705 (2005).

27 Lee, H. G. et al. Cell cycle re-entry and mitochondrial defects in myc-mediated hypertrophic cardiomyopathy and heart failure. *PloS one* 4, e7172, doi:10.1371/journal.pone.0007172 (2009).

28 Liao, H. S. et al. Cardiac-specific overexpression of cyclin-dependent kinase 2 increases smaller mononuclear cardiomyocytes. *Circulation research* 88, 443-450 (2001).

29 Ozhan, G. & Weidinger, G. Wnt/beta-catenin signaling in heart regeneration. *Cell regeneration* 4, 3, doi:10.1186/s13619-015-0017-8 (2015).

30 Kuhn, B. et al. Periostin induces proliferation of differentiated cardiomyocytes and promotes cardiac repair. *Nature medicine* 13, 962-969, doi:10.1038/nm1619 (2007).

31 Lin, Z. et al. Cardiac-specific YAP activation improves cardiac function and survival in an experimental murine MI model. *Circulation research* 115, 354-363, doi:10.1161/CIRCRESAHA.115.303632 (2014).

32 Heallen, T. et al. Hippo signaling impedes adult heart regeneration. *Development* 140, 4683-4690, doi:10.1242/dev.102798 (2013).

33 Heallen, T. et al. Hippo pathway inhibits Wnt signaling to restrain cardiomyocyte proliferation and heart size. *Science* 332, 458-461, doi:10.1126/science.1199010 (2011).

34 Wei, K. et al. Epicardial FSTL1 reconstitution regenerates the adult mammalian heart. *Nature* 525, 479-485, doi:10.1038/nature15372 (2015).

35 Ebelt, H. et al. Directed expression of dominant-negative p73 enables proliferation of cardiomyocytes in mice. *Journal of molecular and cellular cardiology* 45, 411-419, doi:10.1016/j.yjmcc.2008.06.006 (2008).

36 Gao, X., Wang, H., Yang, J. J., Liu, X. & Liu, Z. R. Pyruvate kinase M2 regulates gene transcription by acting as a protein kinase. *Molecular cell* 45, 598-609, doi:10.1016/j.molcel.2012.01.001 (2012).

37 Gupta, V. & Bamezai, R. N. Human pyruvate kinase M2: a multifunctional protein. *Protein science: a publication of the Protein Society* 19, 2031-2044, doi:10.1002/pro.505 (2010).

38 Luo, W. & Semenza, G. L. Pyruvate kinase M2 regulates glucose metabolism by functioning as a coactivator for hypoxia-inducible factor 1 in cancer cells. *Oncotarget* 2, 551-556, doi:10.18632/oncotarget.299 (2011).

39 Mazurek, S. Pyruvate kinase type M2: a key regulator of the metabolic budget system in tumor cells. *The international journal of biochemistry & cell biology* 43, 969-980, doi:10.1016/j.biocel.2010.02.005 (2011).

40 Spoden, G. A. et al. Pyruvate kinase isoenzyme M2 is a glycolytic sensor differentially regulating cell proliferation, cell size and apoptotic cell death dependent on glucose supply. *Experimental cell research* 315, 2765-2774, doi:10.1016/j.yexcr.2009.06.024 (2009).

41 Vander Heiden, M. G., Cantley, L. C. & Thompson, C. B. Understanding the Warburg effect: the metabolic requirements of cell proliferation. *Science* 324, 1029-1033, doi:10.1126/science.1160809 (2009).

42 Wu, S. & Le, H. Dual roles of PKM2 in cancer metabolism. *Acta biochimica et biophysica Sinica* 45, 27-35, doi:10.1093/abbs/gms106 (2013).

43 Kumar, B. & Bamezai, R. N. Moderate DNA damage promotes metabolic flux into PPP via PKM2 Y-105 phosphorylation: a feature that favours cancer cells. *Molecular biology reports* 42, 1317-1321, doi:10.1007/s11033-015-3876-8 (2015).

44 Salani, B. et al. IGF1 regulates PKM2 function through Akt phosphorylation. *Cell cycle* 14, 1559-1567, doi:10.1080/15384101.2015.1026490 (2015).

45 Wong, N., De Melo, J. & Tang, D. PKM2, a Central Point of Regulation in Cancer Metabolism. *International journal of cell biology* 2013, 242513, doi:10.1155/2013/242513 (2013).

46 Luo, N. et al. Induction of Apoptosis in Human Leukemic Cell Lines by Diallyl Disulfide via Modulation of EGFR/ERK/PKM2 Signaling Pathways. *Asian Pacific journal of cancer prevention: APJCP* 16, 3509-3515 (2015).

47 Zhang, J. et al. Nuclear translocation of PKM2 modulates astrocyte proliferation via p27 and—catenin pathway after spinal cord injury. *Cell cycle* 14, 2609-2618, doi:10.1080/15384101.2015.1064203 (2015).

48 David, C. J., Chen, M., Assanah, M., Canoll, P. & Manley, J. L. HnRNP proteins controlled by c-Myc deregulate pyruvate kinase mRNA splicing in cancer. *Nature* 463, 364-368, doi:10.1038/nature08697 (2010).

49 Haubner, B. J. et al. Complete cardiac regeneration in a mouse model of myocardial infarction. *Aging* 4, 966-977, doi:10.18632/aging.100526 (2012).

50 Hamma, T. & Ferre-D'Amare, A. R. Structure of protein L7Ae bound to a K-turn derived from an archaeal box H/ACA sRNA at 1.8 A resolution. *Structure* 12, 893-903, doi: 10.1016/j.str.2004.03.015 (2004).

51 Wroblewska, L. et al. Mammalian synthetic circuits with RNA binding proteins for RNA-only delivery. *Nature biotechnology* 33, 839-841, doi:10.1038/nbt.3301 (2015).

52 van Rooij, E. & Olson, E. N. MicroRNA therapeutics for cardiovascular disease: opportunities and obstacles. *Nature reviews. Drug discovery* 11, 860-872, doi: 10.1038/nrd3864 (2012).

53 Williams, A. H., Liu, N., van Rooij, E. & Olson, E. N. MicroRNA control of muscle development and disease. *Current opinion in cell biology* 21, 461-469, doi:10.1016/j.ceb.2009.01.029 (2009).

54 Ye, Y., Perez-Polo, J. R., Qian, J. & Birnbaum, Y. The role of microRNA in modulating myocardial ischemia-reperfusion injury. *Physiological genomics* 43, 534-542, doi:10.1152/physiolgenomics.00130.2010 (2011).

55 Porrello, E. R. et al. Transient regenerative potential of the neonatal mouse heart. *Science* 331, 1078-1080, doi:10.1126/science.1200708 (2011).

56 Lesizza, P. et al. Single-Dose Intracardiac Injection of Pro-Regenerative MicroRNAs Improves Cardiac Function After Myocardial Infarction. *Circulation research*, doi:10.1161/CIRCRESAHA.116.309589 (2017).

The invention claimed is:

1. An expression regulatory system for cell-specific expression of a gene of interest (GOI) comprising:
   a first nucleic acid that encodes a microRNA (miR) recognition element near its 3'UTR that specifically binds a target cell-specific miR, and a translation suppressor protein; and
   a second nucleic acid that comprises a suppressor protein interaction motif that binds the translation suppressor protein, and a gene that encodes a protein of interest, wherein the protein of interest is a cell cycle inducer protein; wherein
   (a) said first nucleic acid comprises the nucleotide sequence of SEQ ID NO: 2, SEQ ID NO: 3, or SEQ ID NO: 4,
   (b) said second nucleic acid comprises the nucleotide sequence of SEQ ID NO: 5, SEQ ID NO: 6, SEQ ID NO: 7 or SEQ ID NO: 8,
   or both (a) and (b).

2. The system of claim 1, wherein said first and second nucleic acids are modified RNA (modRNA).

3. The system of claim 1, wherein the target cell is a cardiomyocyte and the target cell miR is selected from the group consisting of miR1, miR208 and miR1 plus miR208.

4. The system of claim 1, wherein the translation suppressor protein is L7Ae and the suppressor protein interaction motif is a k-motif.

5. The system of claim 1, wherein the gene further encodes a reporter protein or selection marker.

6. The system of claim 5, wherein the reporter protein or selection marker is a fluorescent protein or antibiotic resistance marker.

7. The system of claim 5, wherein the reporter protein or selection marker is selected from the group consisting of green fluorescence protein (GFP), nuclear GFP (nGFP), inactive human CD25, (ihCD25) and inactive mouse CD25 (imCD25).

8. The system of claim 1, wherein the cell cycle inducer protein is selected from the group consisting of Lin28 and Pkm2.

9. The system of claim 1, wherein said first nucleic acid comprises the nucleotide sequence of SEQ ID NO: 2, SEQ ID NO: 3, or SEQ ID NO: 4.

10. The system of claim 1, wherein said second nucleic acid comprises the nucleotide sequence of SEQ ID NO: 5, SEQ ID NO: 6, SEQ ID NO: 7 or SEQ ID NO: 8.

11. A composition comprising first and second nucleic acids of claim 1.

12. The composition of claim 11, wherein said nucleic acids are obtained by in vitro transcription.

13. The composition of claim 11, wherein a first vector comprises the first nucleic acid and a second vector comprises the second nucleic acid.

14. A vector comprising first and second nucleic acids of claim 1.

15. A method for expressing a protein in a cell of interest, the method comprising contacting said cell with a modRNA encoding an anti-miR specific for a miR target of said cell of interest, wherein said protein of interest is a cell cycle inducer protein, said cell of interest is a cardiomyocyte (CM), and said modRNA encoding an anti-miR specific for a cardiomyocyte miR target comprises the nucleotide sequence of SEQ ID NO: 2, SEQ ID NO: 3, or SEQ ID NO: 4.

16. A method for inducing/reactivating proliferation of neonatal or adult cardiomyocytes in vitro or in vivo following myocardial infarction (MI), the method comprising contacting a portion of said cardiomyocytes with a first modRNA that encodes a recognition element for a cardiomyocyte-specific miR and a translation suppressor protein and a second modRNA that encodes a k-motif to bind the translation suppressor protein and a cell cycle inducer gene, wherein said miR is miR1, miR208, or a combination of miR1 and miR208.

17. The method of claim 16, wherein the cell cycle inducer gene is selected from the group consisting of Lin28 and Pkm2 and Cyclin D2.

18. The method of claim 16, wherein the inducing/reactivating proliferation comprises inducing/reactivating proliferation of adult cardiomyocytes in vivo following myocardial infarction (MI).

* * * * *